(12) United States Patent
Liu et al.

(10) Patent No.: US 12,281,116 B2
(45) Date of Patent: Apr. 22, 2025

(54) HTT MODULATORS FOR TREATING HUNTINGTON'S DISEASE

(71) Applicant: CHDI Foundation, Inc., New York, NY (US)

(72) Inventors: Longbin Liu, Thousand Oaks, CA (US); Celia Dominguez, Los Angeles, CA (US); Nikolay V. Plotnikov, Los Angeles, CA (US); Alan Haughan, Saffron Walden (GB); Andrew Stott, Saffron Walden (GB); Brett Cosgrove, Saffron Walden (GB); Cole Clissold, Saffron Walden (GB); Huw Vater, Saffron Walden (GB); Jonathan Spencer, Saffron Walden (GB); William Esmieu, Saffron Walden (GB); Karine Malagu, Saffron Walden (GB); Mark Chambers, Saffron Walden (GB)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 17/988,340

(22) Filed: Nov. 16, 2022

(65) Prior Publication Data

US 2023/0159531 A1    May 25, 2023

Related U.S. Application Data

(60) Provisional application No. 63/280,551, filed on Nov. 17, 2021.

(51) Int. Cl.
| | | |
|---|---|---|
| *C07D 471/10* | (2006.01) | |
| *A61K 45/06* | (2006.01) | |
| *C07D 403/14* | (2006.01) | |
| *C07D 405/14* | (2006.01) | |
| *C07D 413/14* | (2006.01) | |
| *C07D 471/04* | (2006.01) | |

(52) U.S. Cl.
CPC ............ *C07D 471/10* (2013.01); *A61K 45/06* (2013.01); *C07D 403/14* (2013.01); *C07D 405/14* (2013.01); *C07D 413/14* (2013.01); *C07D 471/04* (2013.01)

(58) Field of Classification Search
CPC .. C07D 471/10; C07D 471/04; C07D 403/14; C07D 405/14; C07D 413/14; A61K 45/06
See application file for complete search history.

(56) References Cited

U.S. PATENT DOCUMENTS

| | | |
|---|---|---|
| 7,504,412 B2 | 3/2009 | Kishino et al. |
| 8,168,630 B2 | 5/2012 | Tamura et al. |
| 9,604,957 B2 | 3/2017 | Chang et al. |
| 9,975,900 B2 | 5/2018 | Pinard et al. |
| 10,501,482 B2 | 12/2019 | Dakka et al. |
| 10,874,672 B2 | 12/2020 | Babu et al. |
| 10,881,658 B2 | 1/2021 | Babu et al. |
| 11,806,346 B2 | 11/2023 | Dominguez et al. |
| 2005/0165028 A1 | 7/2005 | Norman et al. |
| 2019/0330159 A1 | 10/2019 | Kitano et al. |

FOREIGN PATENT DOCUMENTS

| | | |
|---|---|---|
| EP | 1657242 A1 | 5/2006 |
| EP | 3386511 B1 | 5/2021 |
| JP | 2007051121 A | 3/2007 |
| WO | WO2004/072069 A1 | 8/2004 |
| WO | WO2004/078163 A2 | 9/2004 |
| WO | WO2007/041634 A1 | 4/2007 |
| WO | WO2014/028459 A1 | 2/2014 |
| WO | WO2014/209841 A2 | 12/2014 |
| WO | WO2015/197503 A1 | 12/2015 |
| WO | WO2016/187544 A1 | 11/2016 |
| WO | WO2017/100726 A1 | 6/2017 |
| WO | WO2018/098446 A1 | 5/2018 |
| WO | WO2018/226622 A1 | 12/2018 |
| WO | WO2018/232039 A1 | 12/2018 |
| WO | WO2019/005980 A1 | 1/2019 |
| WO | WO2019/005993 A1 | 1/2019 |
| WO | WO2019/028440 A1 | 2/2019 |
| WO | WO2019/191092 A1 | 10/2019 |
| WO | WO2019/191229 A1 | 10/2019 |
| WO | WO2020/005873 A1 | 1/2020 |
| WO | WO2020/005877 A1 | 1/2020 |
| WO | WO2020/005882 A1 | 1/2020 |
| WO | WO2020/163248 A1 | 8/2020 |
| WO | WO2020/163323 A1 | 8/2020 |
| WO | WO2020/163375 A1 | 8/2020 |
| WO | WO2020/163382 A1 | 8/2020 |
| WO | WO2020/163401 A1 | 8/2020 |
| WO | WO2020/163405 A1 | 8/2020 |
| WO | WO2020/163406 A1 | 8/2020 |
| WO | WO2020/163409 A1 | 8/2020 |
| WO | WO2020/163541 A1 | 8/2020 |
| WO | WO2020/163544 A1 | 8/2020 |
| WO | WO2020/163647 A1 | 8/2020 |
| WO | WO2020/167624 A1 | 8/2020 |
| WO | WO2020/167628 A1 | 8/2020 |
| WO | WO2020/231977 A1 | 11/2020 |
| WO | WO2021/007378 A1 | 1/2021 |
| WO | WO2021/084495 A1 | 5/2021 |
| WO | WO2021/174163 A1 | 9/2021 |
| WO | WO2021/174164 A1 | 9/2021 |
| WO | WO2021/174165 A1 | 9/2021 |

(Continued)

OTHER PUBLICATIONS

International Search Report and Written Opinion for PCT/US2021/031988, Jul. 20, 2021, 13 pages.
International Search Report and Written Opinion for PCT/US2022/050058, Nov. 16, 2022, 14 pages.

(Continued)

*Primary Examiner* — Matthew P Coughlin
*Assistant Examiner* — Quincy McKoy
(74) *Attorney, Agent, or Firm* — Sheppard Mullin & Hampton LLP

(57) ABSTRACT

Provided herein are certain compounds useful as HTT modulators. Such compound are useful in the treatment of Huntington's disease.

19 Claims, No Drawings

(56) References Cited

FOREIGN PATENT DOCUMENTS

| WO | WO2021/174167 A1 | 9/2021 |
| WO | WO2021/174170 A1 | 9/2021 |
| WO | WO2021/174174 A1 | 9/2021 |
| WO | WO2021/174176 A1 | 9/2021 |
| WO | WO2021/207453 A1 | 10/2021 |
| WO | WO2021/207530 A1 | 10/2021 |
| WO | WO2021/207532 A1 | 10/2021 |
| WO | WO2021/207550 A1 | 10/2021 |
| WO | WO2021/207554 A1 | 10/2021 |
| WO | WO2021/231571 A1 | 11/2021 |

OTHER PUBLICATIONS

Database Registry [Online] Chemical Abstracts Service, Columbus, Ohio, Mar. 25, 2010, Asinex, "5-Pyrimidinecarboxamide, N-(2-methyl-6-benzothiazolyl)-2-(4-methyll-piperidinyl)-", retrieved from STN Database accession No. 1214424-22-2 abstract, XP055821964.

Database Registry [Online] Chemical Abstracts Service, Columbus, Ohio, Jul. 29, 2015, Enamine LLC, "3-Pyridazinecarboxamide, N-(5-methyl-IH-indazol-6-yl)-6-(1-pyrrolidinyl)-", retrieved from STN Database accession No. 1808451-86-6 abstract, XP055821949.

Database Registry [Online] Chemical Abstracts Service, Columbus, Ohio, US; Sep. 27, 2012, Life Chemical et al., "3-Pyridazinecarboxamide,N—IH-indazol-6-yl-6-(4-morpholinyl)-", retrieved from STN Database accession No. 1396882-20-4 abstract, XP055821536.

Hintermann et al., "Synthesis and Biological Evaluation of New Triazolo- and Imidazolaoyridine ROR [gamma] t Inverse Agonists", Chemmedchem Communication, Dec. 16, 2016, vol. 11, No. 24, pp. 2640-2468.

Kargbo, "Modulation of RNA Splicing for the Treatment of Cancer", ACS Medicinal Chemistry Letters, 2020, vol. 11, No. 1, pp. 7-8.

Cheung et al., Discovery of Small Molecule Splicing Modulators of Survival Motor Neuron-2 (SMN2) for the Treatment of Spinal Muscular Atrophy (SMA), Journal of Medicinal Chemistry, 2018, vol. 61, pp. 11021-11036.

Westaway S M et al. "N-Tetrahydroquinolinyl, N-quinolinyl and N-isoquinolinyl biaryl carboxamides as antagonists of TRPV1", Bioorganic & Medicinal Chemistry Letters, Elsevier, Amsterdam NL, vol. 16, No. 17, Sep. 2006, pp. 4533-4536.

Wu et al., "Regulatory perspectives of Type II prodrug development and time-dependent toxicity management: Nonclinical Pharm/Tox analysis and the role of cmparitive toxicology" Toxicology, vol. 236, pp. 1-6 (Year: 2007).

Gamo F J et al, "Thousands of chemical starting points for antimalarial lead identification", Nature, Nature Publishing Group UK, London, vol. 465, May 20, 2010, pp. 305-310.

HTT MODULATORS FOR TREATING HUNTINGTON'S DISEASE

CROSS-REFERENCE TO RELATED APPLICATIONS

This application claims the benefit under 35 U.S.C. § 119(e) of U.S. Provisional Application Ser. No. 63/280,551, filed Nov. 17, 2021, the contents of which are hereby incorporated by reference in their entirety.

FIELD

The present disclosure relates to modulators of HTT and methods of preventing and/or treating a neurodegenerative disease or condition.

BACKGROUND

Huntington's disease (HD) is a dominant inherited progressive neurodegenerative disorder, characterized by motor, cognitive, and psychiatric deficits as well as neurodegeneration and brain atrophy beginning in the striatum and the cortex and extending to other subcortical brain regions. HD has a prevalence of 5-10 cases per 100,000 worldwide, which makes it the most common inherited monogenetic neurodegenerative disease.

Neurodegenerative diseases and conditions, such as Huntington's disease, have a profound negative impact on the lives of those effected. Current treatments for Huntington's disease are palliative, aimed at lessening the severity of symptoms. There is no disease modifying treatment available.

Huntington's disease is caused by the expansion of a CAG repeat domain in Exon 1 of the huntingtin gene (HTT), which is expressed as mutant huntingtin protein (mHTT), containing an expanded polyglutamine tract in the amino terminal domain of the protein. The molecular route of pathogenesis is not entirely understood even though HD is monogenic and autosomal dominant. Therefore, mHTT lowering is a clear therapeutic strategy targeting the gene products of the causative gene. In fact, several therapeutic strategies targeting mHTT lowering via antisense oligionucleotide (ASO) or AAV-miR mediated HTT RNA degradation are advancing through clinical trials in HD and have demonstrated lowering of mHTT levels in the CSF of treated patients.

While these modalities show great promise, they are invasive (involving repeated intrathecal injections); their distribution throughout the brain to all affected regions is not certain; and they do not address any peripheral dysfunction the ubiquitously distributed mHTT may be responsible for. Therefore, small molecule HTT lowering agents that can be delivered systemically and non-invasively would be an attractive HTT lowering therapy to pursue. Thus, there is a need for small molecule modulators of HTT protein. Such molecules may find use in treating the symptoms and/or delaying the disease progression of Huntington's disease.

SUMMARY

The present disclosure relates generally to small molecule modulators of HTT, and use thereof as therapeutic agents, for example, in treating diseases such as Huntington's disease.

Thus, provided herein are compounds, or an isotopically enriched analog, pharmaceutically acceptable salt, prodrug, tautomer, stereoisomer, or a mixture of stereoisomers of the compounds, that are useful in treating Huntington's disease.

In certain embodiments, provided are compounds that modulate a protein or a protein fragment implicated in neurodegenerative disease, for example, HTT protein.

In certain embodiments, provided is a pharmaceutical composition comprising a compound described herein, or an isotopically enriched analog, pharmaceutically acceptable salt, prodrug, tautomer, stereoisomer, or a mixture of stereoisomers thereof, and a pharmaceutically acceptable excipient.

The disclosure also provides compositions, including pharmaceutical compositions, kits that include the compounds, and methods of using (or administering) and making the compounds. The disclosure further provides compounds or compositions thereof for use in a method of treating a disease or condition that is mediated, at least in part, by a protein, or a protein fragment, implicated in neurodegenerative disease. Moreover, the disclosure provides uses of the compounds or compositions thereof in the manufacture of a medicament for the treatment of a disease or condition that is mediated, at least in part, by a protein, or a protein fragment, implicated in neurodegenerative disease.

DETAILED DESCRIPTION

The following description sets forth exemplary embodiments of the present technology. It should be recognized, however, that such description is not intended as a limitation on the scope of the present disclosure but is instead provided as a description of exemplary embodiments.

Definitions

As used in the present specification, the following words, phrases and symbols are generally intended to have the meanings as set forth below, except to the extent that the context in which they are used indicates otherwise.

A compound described herein refers to a compound, or an isotopically labeled analog, pharmaceutically acceptable salt, solvate, prodrug, stereoisomer, or mixture of stereoisomers thereof, of any formula described herein, including those of Formula I, Formula Ia, Formula Ib, Formula Ic, Formula IIa, Formula IIb, Formula IIIa, Formula IIIb, Formula IIIc, or a compound described anywhere herein including the Examples, or a compound of Table 1, Table 2, or Table 2A.

A dash ("-") that is not between two letters or symbols is used to indicate a point of attachment to a parent structure for a substituent. For example, —C(O)NH$_2$ is attached to a parent structure through the carbon atom. A dash at the front or end of a chemical group is a matter of convenience; chemical groups may be depicted with or without one or more dashes without losing their ordinary meaning. A wavy line or a dashed line drawn through a bond in a structure indicates a specified point of attachment. Unless chemically or structurally required, no directionality or stereochemistry is indicated or implied by the order in which a chemical group is written or named.

The prefix "$C_{u-v}$" indicates that the following group has from u to v carbon atoms, exclusive of further substitution. For example, "$C_{1-6}$ alkyl" indicates an alkyl group having from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 9 carbon atoms (i.e., $C_{1-9}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —CH($CH_3$)$CH_2CH_3$), isobutyl (i.e., —$CH_2CH(CH_3)_2$), and tert-butyl (i.e., —$C(CH_3)_3$); and "propyl" includes n-propyl (i.e., —$(CH_2)_2CH_3$) and isopropyl (i.e., —$CH(CH_3)_2$).

Alternative chemical names known to those of skill in the art may be used in lieu of the terms provided herein. For example, a divalent group such as a divalent "alkyl" group or a divalent "aryl" group, etc., may also be referred to as an "alkylene" or an "arylene" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-6}$ alkenyl), 2 to 6 carbon atoms (i.e., $C_{2-6}$ alkenyl) or 2 to 4 carbon atoms (i.e., $C_{24}$ alkenyl). Examples of alkenyl groups include, e.g., ethenyl, propenyl, butadienyl (including 1,2-butadienyl and 1,3-butadienyl), and isoprenyl.

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-6}$ alkynyl), 2 to 6 carbon atoms (i.e., $C_{2-6}$ alkynyl) or 2 to 4 carbon atoms (i.e., $C_{24}$ alkynyl). The term "alkynyl" also includes those groups having one triple bond and one double bond.

"Alkoxy" refers to a group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy, and 1,2-dimethylbutoxy.

"Alkylamino" refers to a group "alkyl-NH—". Examples of alkylamino groups include, e.g., methylamino, ethylamino, iso-propylamino, tert-butylamino, and n-hexylamino. "Dialkylamino" refers to a group "(alkyl)$_2$N—". Examples of dialkylamino groups include, e.g., dimethylamino, diethylamino, (iso-propyl)(methyl)amino, (n-pentyl)(tert-butyl)amino, and di-n-hexylamino.

"Alkylthio" refers to a group "alkyl-S—". "Alkylsulfinyl" refers to a group "alkyl-S(O)—". "Alkylsulfonyl" refers to a group "alkyl-S(O)$_2$—".

"Acyl" refers to a group —C(O)$R^y$, wherein $R^y$ is hydrogen, alkyl, alkenyl, alkynyl, cycloalkyl, heterocyclyl, aryl, heteroalkyl, or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to a group —C(O)$NR^yR^z$ and an "N-amido" group which refers to a group —$NR^yC(O)R^z$, wherein $R^y$ and $R^z$ are independently hydrogen, alkyl, alkenyl, alkynyl, haloalkyl, cycloalkyl, heterocyclyl, aryl, heteroalkyl, or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to a group —$NR^yR^z$ wherein $R^y$ and $R^z$ are independently hydrogen, alkyl, alkenyl, alkynyl, haloalkyl, cycloalkyl, heterocyclyl, aryl, heteroalkyl, or heteroaryl; each of which may be optionally substituted, as defined herein. In some embodiments, "amino" refers to a group $NH_2$.

"Amidino" refers to a group —C($NR^y$)($NR^z_2$), wherein $R^y$ and $R^z$ are independently hydrogen, alkyl, alkenyl, alkynyl, haloalkyl, cycloalkyl, heterocyclyl, aryl, heteroalkyl, or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl) or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to a group "aryl-alkyl-".

"Carbamoyl" refers to both an "O-carbamoyl" group which refers to a group —O—C(O)$NR^yR^z$ and an "N-carbamoyl" group which refers to a group —$NR^yC(O)OR^z$, wherein $R^y$ and $R^z$ are independently hydrogen, alkyl, alkenyl, alkynyl, haloalkyl, cycloalkyl, heterocyclyl, aryl, heteroalkyl, or heteroaryl; each of which may be optionally substituted, as defined herein.

"Carboxyl ester" or "ester" refer to both —OC(O)$R^x$ and —C(O)$OR^x$, wherein $R^x$ is alkyl, alkenyl, alkynyl, haloalkyl, cycloalkyl, heterocyclyl, aryl, heteroalkyl, or heteroaryl; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond) and carbocyclic fused ring systems having at least one $sp^3$ ring carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cyclohexenyl, cycloheptyl and cyclooctyl. Polycyclic groups include, for example, bicyclo[2.2.1]heptanyl, bicyclo[2.2.2]octanyl, adamantyl, norbornyl, norbornenyl, decalinyl, 7,7-dimethyl-bicyclo[2.2.1]heptanyl, and the like. Further, the term cycloalkyl is intended to encompass any non-aromatic ring system which may include a fused aryl ring, regardless of the attachment to the remainder of the molecule. Still further, cycloalkyl also includes "spirocycloalkyl," for example spiro[2.5]octanyl, spiro[4.5]decanyl, or spiro[5.5]undecanyl. When there are two positions for substitution on a carbon atom in a parent structure, cycloalkyl as a substituent group may include spirocycloalkyl. A cycloalkyl may be substituted at its carbon atom of attachment to a parent structure.

"Cycloalkoxy" refers to a group "—O-cycloalkyl."

"Cycloalkylalkyl" refers to a group "cycloalkyl-alkyl-".

"Guanidino" refers to —NR$^y$C(=NR$^z$)(NR$^y$R$^z$), wherein each R$^y$ and R$^z$ are independently hydrogen, alkyl, alkenyl, alkynyl, haloalkyl, cycloalkyl, heterocyclyl, aryl, heteroalkyl, or heteroaryl; each of which may be optionally substituted, as defined herein.

"Imino" refers to a group —C(NR$^y$)R$^z$, wherein R$^y$ and R$^z$ are each independently hydrogen, alkyl, alkenyl, alkynyl, haloalkyl, cycloalkyl, heterocyclyl, aryl, heteroalkyl, or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, haloalkyl, cycloalkyl, heterocyclyl, aryl, heteroalkyl, or heteroaryl; each of which may be optionally substituted, as defined herein.

"Halogen" or "halo" refers to a substituent atom of group VIIA of the periodic table, such as fluoro, chloro, bromo, or iodo.

"Haloalkyl" refers to an unbranched or branched alkyl group as defined above, wherein one or more (e.g., 1 to 6 or 1 to 3) hydrogen atoms, up to and including all hydrogen atoms, are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. A perhaloalkyl group is a haloalkyl group in which every hydrogen substituent is replaced by halo. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Haloalkoxy" refers to an alkoxy group as defined above, wherein one or more (e.g., 1 to 6 or 1 to 3) hydrogen atoms, up to and including all hydrogen atoms, are replaced by a halogen.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms of the alkyl chain (and any associated hydrogen atoms) are each independently replaced with the same or different heteroatomic group, provided the point of attachment to the remainder of the molecule is through a carbon atom. The term "heteroalkyl" includes unbranched or branched saturated chains having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, haloalkyl, cycloalkyl, heterocyclyl, aryl, heteroalkyl. or heteroaryl; each of which may be optionally substituted, as defined herein. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.), and aminoalkyls (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, haloalkyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring or multiple fused rings, with one or more ring heteroatoms independently selected from nitrogen, oxygen, and sulfur, and may comprise one or more (e.g., 1 to 3) N-oxide (—O—) moieties. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring system, having a single or multiple fused rings containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to a group "heteroaryl-alkyl-".

"Heterocyclyl" refers to a saturated or partially unsaturated cyclic alkyl group, with one or more ring heteroatoms independently selected from nitrogen, oxygen, and sulfur, wherein the nitrogen or sulfur atoms are optionally oxidized to form an N-oxide, a sulfinyl (—S(O)—), or a sulfoxide (—S(O)$_2$—). The term "heterocyclyl" includes heterocycloalkenyl groups (i.e., a heterocyclyl group having at least one endocyclic or exocyclic double bond), bridged-heterocyclyl groups, fused-heterocyclyl groups, oxo-heterocyclyl (i.e., a heterocyclyl including at least one oxo), and spiro-heterocyclyl groups. A heterocyclyl may be a single ring or multiple rings wherein the multiple rings may be fused, bridged or spiro. Regardless of substituent groups listed, a heterocyclyl may comprise one or more (e.g., 1 to 3) oxo (=O) or N-oxide (—O—) moieties unless stated otherwise. A heterocyclyl can be bound through a carbon atom or a heteroatom as valency permits. Further, the term heterocyclyl encompasses any ring system including a non-aromatic ring containing at least one heteroatom, which ring may be fused to an aryl or heteroaryl ring, regardless of the attachment to the remainder of the molecule. A heterocyclyl may have a charged resonance structure that is aromatic (e.g., pyridin-2(1H)-on-1-yl). As used herein, a heterocyclyl may include 3 to 14 ring atoms, 3 to 10 ring atoms, 3 to 6 ring atoms, or 5 to 6 ring atoms, and/or 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl.". Examples of the spiroheterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of bridged-heterocyclyl rings include, but are not limited to, 2,5-diazabicyclo[2.2.1]heptane, 2-oxa-5-azabicyclo[2.2.1]heptanyl. When there are two positions for substitution on a carbon atom in a parent structure, heterocyclyl as a substituent group may include spiroheterocyclyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to a group "heterocyclylalkyl-."

"Heterocyclyloxy" refers to a group "heterocyclyl-O—."

"Oxime" refers to a group —$CR^y$(=NOH) wherein $R^y$ is hydrogen, alkyl, alkenyl, alkynyl, haloalkyl, cycloalkyl, heterocyclyl, aryl, heteroalkyl, or heteroaryl; each of which may be optionally substituted, as defined herein.

"Sulfonyl" refers to a group —$S(O)_2R^y$, where $R^y$ is hydrogen, alkyl, alkenyl, alkynyl, haloalkyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl and toluenesulfonyl.

"Sulfinyl" refers to a group —$S(O)R^y$, where $R^y$ is hydrogen, alkyl, alkenyl, alkynyl, haloalkyl, cycloalkyl, heterocyclyl, aryl, heteroalkyl, or heteroaryl; each of which may be optionally substituted, as defined herein. Examples of sulfinyl are methylsulfinyl, ethylsulfinyl, phenylsulfinyl, and toluenesulfinyl.

"Sulfonamido" refers to the groups —$SO_2NR^yR^z$ and —$NR^ySO_2R^z$, where $R^y$ and $R^z$ are each independently hydrogen, alkyl, alkenyl, alkynyl, haloalkyl, cycloalkyl, heterocyclyl, aryl, heteroalkyl, or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to a group which is unsubstituted or substituted.

The term "substituted" used herein refers to a group in which any one or more (e.g., 1 to 5 or 1 to 3) hydrogen atoms is replaced by a non-hydrogen group such as, but not limited to alkyl, alkenyl, alkynyl, alkoxy, alkylthio, acyl, amido, amino, amidino, aryl, arylalkyl, azido, carbamoyl, carboxyl, carboxyl ester, cyano, cycloalkyl, cycloalkoxy, cycloalkylalkyl, guanidino, halo, haloalkyl, haloalkoxy, hydroxyalkyl, heteroalkyl, heteroaryl, heteroarylalkyl, heterocyclyl, heterocyclylalkyl, —$NHNH_2$, =$NNH_2$, imino, imido, hydroxy, oxo, oxime, nitro, sulfonyl, sulfinyl, alkylsulfonyl, alkylsulfinyl, thiocyanate, —$S(O)OH$, —$S(O)_2OH$, sulfonamido, thiol, thioxo, N-oxide or —$Si(R^y)_3$, wherein each $R^y$ is independently hydrogen, alkyl, alkenyl, alkynyl, haloalkyl, heteroalkyl, cycloalkyl, aryl, heteroaryl, or heterocyclyl.

In certain embodiments, "substituted" refers to a group in which one or more (e.g., 1 to 5 or 1 to 3) hydrogen atoms are independently replaced with deuterium, halo, cyano, hydroxyl, imino, nitro, azido, oxo, thioxo, alkyl, alkenyl, alkynyl, haloalkyl, alkoxy, thioalkyl, haloalkoxy, cycloalkyl, heterocyclyl, N-heterocyclyl, heterocyclylalkyl, aryl, arylalkyl, heteroaryl, heteroarylalkyl, —$NR^gR^h$, —$NR^gC(=O)R^h$, —$NR^gC(=O)NR^gR^h$, —$NR^gC(=O)OR^h$, —$NR^gS(=O)_{1-2}R^h$, —$C(=O)R^g$, —$C(=O)OR^g$, —$OC(=O)OR^g$, —$OC(=O)R^g$, —$C(=O)NR^gR^h$, —$OC(=O)NR^gR^h$, —$OR^g$, —$SR^g$, —$S(=O)R^g$, —$S(=O)_2R^g$, —$OS(=O)_{1-2}R^g$, —$S(=O)_{1-2}OR^g$, —$NR^gS(=O)_{1-2}NR^gR^h$, =$NSO_2R^g$, =$NOR^g$, —$S(=O)_{1-2}NR^gR^h$, —$SF_5$, or —$SCF_3$. In certain embodiments, "substituted" also means a group in which one or more (e.g., 1 to 5 or 1 to 3) hydrogen atoms are replaced with —$C(=O)R^g$, —$C(=O)OR^g$, —$C(=O)NR^gR^h$, —$CH_2SO_2R^g$, or —$CH_2SO_2NR^gR^h$. In the foregoing, $R^g$ and $R^h$ are the same or different and independently hydrogen, alkyl, alkenyl, alkynyl, alkoxy, thioalkyl, aryl, arylalkyl, cycloalkyl, cycloalkylalkyl, haloalkyl, heterocyclyl, heterocyclylalkyl, heteroaryl, and/or heteroarylalkyl, or two of $R^g$ and $R^h$ are taken together with the atoms to which they are attached to form a heterocyclyl ring optionally substituted with oxo, halo, or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended to arise from the above definitions. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to encompass compounds having chemically unfeasable or unisolable substitution patterns (e.g., methyl substituted with 5 fluorines or heteroaryl groups having three consecutive oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein is intended to represent unlabeled forms as well as "isotopically enriched analogs" of the compounds. Isotopically enriched forms of compounds may also be referred to as "labeled." Isotopically enriched analogs have structures depicted herein, except that one or more atoms are enriched in an isotope having a selected atomic mass or mass number. Examples of isotopes that can be incorporated into the compounds described herein include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Generally, an isotopically enriched analog includes compounds having any isotopic enrichment above the natural abundance of the isotope (e.g., at Earth's surface). Various isotopically labeled compounds are included in the present disclosure, for example, those into which radioactive isotopes such as $^3$H, $^{18}$F, $^{11}$C, $^{13}$C, and $^{14}$C are incorporated. Compounds labeled with $^{18}$F, $^3$H, or $^{11}$C may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds may exhibit increased resistance to metabolism and thus may be useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example, by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example, increased in vivo half-life, reduced dosage requirements, and/or an improvement in therapeutic index. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Where a compound is described as a deuterated analog, the compound may be drawn with deuterium as a substituent.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen and its isotopes at their natural abundances.

In many cases, the compounds of this disclosure are capable of forming acid and/or base salts by virtue of the presence of amino and/or carboxyl groups or groups similar thereto.

Provided also are isotopically enriched analogs, pharmaceutically acceptable salts, prodrugs, tautomers, stereoisomers, and mixtures of stereoisomers of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a compound described herein refers to salts that retain the biological effectiveness and properties of the given compound and which are not biologically or otherwise undesirable. "Pharmaceutically acceptable salts" or "physiologically acceptable salts" of compounds described herein include, for example, acid addition salts obtained by interacting a compound with a basic functional group with an acid, and base addition salts obtained by interacting a compound with an acidic functional group with a base. If the compound is obtained as an acid addition salt, the free base can be obtained by basifying a solution of the acid salt. Conversely, if the compound is a free base (e.g., of an amine), an addition salt may be produced by dissolving the free base in a suitable organic solvent and treating the solution with an acid. Those skilled in the art will recognize various synthetic methodologies that may be used to prepare nontoxic pharmaceutically acceptable addition salts. Pharmaceutically acceptable acid addition salts of compounds described herein may be prepared from inorganic and organic acids. Suitable inorganic acids include, e.g., hydrochloric acid, hydrobromic acid, sulfuric acid, nitric acid, phosphoric acid, and the like. Suitable organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, aluminum, ammonium, calcium, and magnesium salts. Salts derived from organic bases include, but are not limited to, salts of primary, secondary, and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$), mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$), cyclic amines (e.g., piperidine, piperazine, 1,4-diazabicyclo[2.2.2]octane), aromatic amines (e.g., pyridine, quinoline), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Some compounds described herein may exist as tautomers. For example, where a compound is drawn as including an amide, the compound may exist as an imidic acid tautomer, and where a compound is drawn as including a ketone, the compound may also exist as an enol tautomer. Regardless of which tautomer is shown and regardless of the nature of the equilibrium among tautomers, the compounds are understood by one of ordinary skill in the art to comprise both tautomers. Thus, for example, the amide containing compounds are understood to include their imidic acid tautomers, and the imidic acid containing compounds are understood to include their amide tautomers.

The compounds described herein may include an asymmetric center and may thus give rise to enantiomers, diastereomers, and other stereoisomeric forms that may be defined, in terms of absolute stereochemistry, as (R)- or (S)-, or as (D)- or (L)- for amino acids. Compounds described herein are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain double bonds or other centers of geometric asymmetry, and unless specified otherwise, it is intended that the compounds include both cis- and trans- or E- and Z-geometric isomers.

A "stereoisomer" refers to one of a set of compounds made up of the same atoms bonded by the same bonds but having different three-dimensional structures. Various stereoisomers and mixtures thereof are contemplated including "enantiomers," which refers to stereoisomeric compounds that are non-superimposable mirror images of one another.

A "diastereomer" is one of a set of stereoisomers that have at least two asymmetric atoms that are not mirror-images of each other.

A "prodrug" is any molecule which releases a putatively active parent drug according to a compound described herein in vivo when such prodrug is administered to a mammalian subject. A prodrug may be a form of a compound described herein modified in such a way that the modifications may be cleaved in vivo to release the parent compound. Prodrugs may be prepared by modifying functional groups present in the compound described herein in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to, esters (e.g., acetate, formate, and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein, the terms "group," "moiety," "radical," "substituent," and "fragment" are synonymous and are intended to indicate portions of molecules attachable to other portions of molecules, e.g., through an indicated attachment point or bond.

The term "active agent" is used to indicate a compound which has biological activity in the treatment, amelioration, or prevention of a disease or condition. In some embodiments, an "active agent" is a compound or an isotopically labeled analog, pharmaceutically acceptable salt, solvate, prodrug, stereoisomer, or mixture of stereoisomers thereof, having pharmaceutical utility. For example, an active agent may be an anti-neurodegenerative therapeutic.

The term "effective amount" means an amount, for example, of a compound described herein, sufficient to bring about a desired response in an individual or patient. The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease described herein. The (therapeutically) effective amount may vary depending on the subject, the disease or condition being treated, the weight and age of the subject, the severity of the disease or condition, and the manner of administering, which can be determined by one of ordinary skill in the art.

The term "huntingtin protein" or "HTT protein" as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "protein aggregate," as used herein, refers to an aggregation of protein which may be, for example, an insoluble fibrous amyloid comprising mis-folded HTT protein molecules ("HTT protein aggregate") or mis-folded β-amyloid protein molecules ("β-amyloid aggregate"). A "protein implicated in neurodegenerative disease" may be a protein that is capable of forming such aggregates, in its wild type or in a mutated form, or may be a protein that participates in a pathological process related to a neurodegenerative disease.

In some embodiments, the term "neurodegenerative disease" refers to a disease or condition in which the function of a subject's nervous system becomes impaired. Examples of neurodegenerative diseases include those described herein.

"Treatment" or "treating" means any treatment of a disease state in a patient, including
  a) inhibiting the disease (e.g., decreasing one or more symptoms resulting from the disease or condition, and/or diminishing the extent of the disease or condition);
  b) slowing or arresting the development of clinical symptoms associated with the disease or condition (e.g., stabilizing the disease or condition, preventing or delaying the worsening or progression of the disease or condition, and/or preventing or delaying the spread (e.g., metastasis) of the disease or condition); and/or
  c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival).

"Prevention" or "preventing" means any treatment of a disease or condition that causes the clinical symptoms of the disease or condition not to develop. Compounds may, in some embodiments, be administered to a subject (including a human) who is at risk (e.g., carries a genetic or epigenetic marker, has engaged in an activity, or has been exposed to an environmental condition, associated with the disease or condition) or has a family history of the disease or condition.

"Subject" or "patient" refers to an animal, such as a mammal, that has been or will be the object of treatment, observation or experiment. The methods described herein may be useful in both human therapy and veterinary applications. In some embodiments, the subject or patient is a mammal. In some embodiments the subject or patient is human.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I are specifically embraced herein just as if each and every combination was individually and explicitly recited, to the extent that such combinations result in stable compounds (i.e., compounds that can be isolated, characterized, and tested for biological activity). In addition, all subcombinations of the chemical groups listed in the embodiments describing such variables, as well as all subcombinations of uses and medical indications described herein, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

Compounds

Provided herein are compounds for modulating HTT. In certain embodiments, provided is a compound of Formula I:

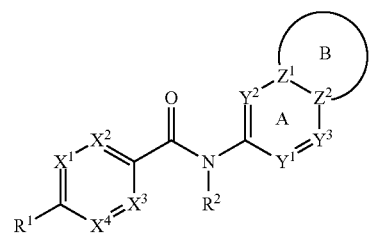

or an isotopically enriched analog, pharmaceutically acceptable salt, prodrug, tautomer, stereoisomer, or a mixture of stereoisomers thereof, wherein:

$X^1$, $X^2$, $X^3$, and $X^4$ are $CR^4$ or N, wherein at least two but no more than three of $X^1$, $X^2$, $X^3$, and $X^4$ are N;

each $R^4$ is independently hydrogen, halo, hydroxy, $C_{1-6}$alkyl, $C_{1-6}$haloalkyl, or $C_{1-6}$alkoxy;

$Y^1$ is $CR^5$ or N;

$R^5$ is hydrogen, heterocyclyloxy, or $C_{1-6}$alkoxy substituted with $C_{2-6}$alkynyl, aryl, $C_{1-6}$alkoxy, heteroaryl, heterocyclyl, or cyano;

$Y^2$ is absent, $CR^6$, or N;

$R^6$ is hydrogen, cyano, halo, hydroxy, $C_{1-6}$alkyl, $C_{1-6}$haloalkyl, $C_{1-6}$alkylthio, $C_{1-6}$alkoxy, $C_{1-6}$haloalkoxy, heterocyclyl, —$NH_2$, —$NHR^{17}$, or —$N(R^{17})_2$, and optionally substituted on an available nitrogen atom with $C_{1-6}$alkyl or $C_{1-6}$haloalkyl; and $Y^3$ is $CR^3$ or N;

$R^3$ is hydrogen, cyano, halo, hydroxy, $C_{1-6}$alkyl, $C_{1-6}$haloalkyl, $C_{1-6}$alkylthio, $C_{1-6}$alkoxy, $C_{1-6}$haloalkoxy, heterocyclyl, —$NH_2$, —$NHR^{17}$, or —$N(R^{17})_2$, and optionally substituted on an available nitrogen atom with $C_{1-6}$alkyl or $C_{1-6}$haloalkyl;

each $R^{17}$ is independently $C_{1-4}$alkyl, or two $R^{17}$ join, with any intervening atoms, to form a 3- to 6-membered heterocyclyl;

each of $Z^1$ and $Z^2$ is C or N;

Ring A and Ring B together form a 9- or 10-membered bicyclic heteroaryl containing 1 to 3 ring nitrogen atoms;

Ring B contains 1 to 3 heteroatoms independently selected from N, O, and S, and is optionally substituted on available carbon atom(s) with 1 to 3 substituents independently selected from halo, hydroxy, $C_{1-6}$alkyl, $C_{1-6}$haloalkyl, $C_{1-6}$alkoxy, and $C_{1-6}$haloalkoxy, and optionally substituted on an available nitrogen atom with $C_{1-6}$alkyl or $C_{1-6}$haloalkyl;

$R^1$ is -$L^1$-$R^{11}$, wherein $L^1$ is —O—, —S—, —S(O)—, —S(O)$_2$—, —N($R^{12}$)—, —$C_{1-3}$alkylene-, —O—$C_{1-3}$alkylene-, —N($R^{12}$)—$C_{1-3}$alkylene-, or absent, and $R^{11}$ is $C_{2-6}$alkynyl, $C_{3-10}$cycloalkyl, $C_{6-10}$aryl, heteroaryl, or heterocyclyl, wherein $R^{11}$ is optionally substituted with 1 to 4 $R^{13}$ groups;

$R^{12}$ is hydrogen or $C_{1-6}$alkyl;

each $R^{13}$ is independently selected from halo, cyano, hydroxy, $C_{1-6}$alkyl optionally substituted with $R^{16}$, $C_{1-6}$haloalkyl, $C_{1-6}$hydroxyalkyl, $C_{3-10}$cycloalkyl optionally substituted with $R^{16}$, $C_{3-10}$cycloalkyl-$C_{1-6}$ alkyl optionally substituted with $R^{16}$, $C_{6-10}$aryl optionally substituted with $R^{16}$, $C_{6-10}$aryl-$C_{1-6}$alkyl optionally substituted with $R^{16}$, heteroaryl optionally substituted with $R^{16}$, heteroaryl-$C_{1-6}$alkyl optionally substituted with $R^{16}$, heterocyclyl optionally substituted with $R^{16}$, heterocyclyl-$C_{1-6}$alkyl optionally substituted with $R^{16}$, $OR^{14}$, —$NH_2$, —$NHR^{14}$, —$N(R^{14})_2$, —$C_{1-6}$ alkylene-$NH_2$, —$C_{1-6}$alkylene-$NHR^{14}$, —$C_{1-6}$alkylene-$N(R^{14})_2$, —$C(O)R^{15}$, —$C(O)OR^{15}$, —$C(O)NHR^{15}$, —$C(O)N(C_{1-4}$alkyl)$R^{15}$, —$S(O)_2R^{15}$, —$S(O)R^{15}$, —$NHC(O)R^{15}$, —$N(C_{1-4}$alkyl)$C(O)R^{15}$, —$NHS(O)R^{15}$, —$N(C_{1-4}$alkyl)$S(O)R^{15}$, —$NHS(O)_2R^{15}$, and —$N(C_{1-4}$alkyl)$S(O)_2R^{15}$;

each $R^{14}$ is independently selected from $C_{1-6}$alkyl, $C_{3-10}$cycloalkyl, $C_{6-10}$aryl, heteroaryl, and heterocyclyl; and each $R^{14}$ is optionally substituted with one to six halo, $C_{1-3}$alkyl, $C_{1-3}$alkoxy, $C_{3-10}$cycloalkyl, or —$NHSO_2$-aryl-$N(CH_3)_2$;

each $R^{15}$ is independently hydrogen, —OH, $C_{1-6}$alkyl, $C_{1-6}$haloalkyl, $C_{3-10}$cycloalkyl, $C_{6-10}$aryl, heteroaryl, or heterocyclyl;

each $R^{16}$ is independently halo, cyano, hydroxy, —$NH_2$, —$NHR^{21}$, —$N(R^{21})_2$, $C_{1-6}$alkyl, $C_{1-6}$haloalkyl, $OR^{21}$, or $C_{3-10}$cycloalkyl;

each $R^{21}$ is independently selected from $C_{1-6}$alkyl, $C_{3-10}$cycloalkyl, $C_{6-10}$aryl, heteroaryl, heterocyclyl, and —$CH_2C(O)NHR^{22}$; and each $R^{21}$ is optionally substituted with one to six halo or $C_{1-3}$alkoxy and $R^{22}$ is $C_{1-6}$alkyl substituted with heterocyclyl and $N_3$; and $R^2$ is hydrogen or $C_{1-6}$alkyl;

provided that when $R^5$ is hydrogen, $R^1$ is heterocyclyl substituted with heterocyclyl-$C_{1-6}$alkyl substituted with —$OCH_2C(O)NHR^{22}$.

In certain embodiments, provided is a compound of Formula Ia:

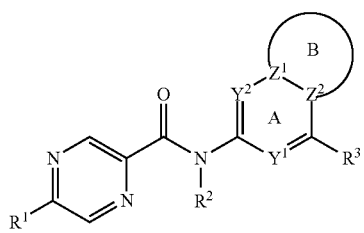

Ia or an isotopically enriched analog, pharmaceutically acceptable salt, prodrug, tautomer, stereoisomer, or a mixture of stereoisomers thereof, wherein Ring A, Ring B, $R^1$, $R^2$, $R^3$, $Y^1$, $Y^2$, $Z^1$, and $Z^2$ are as defined herein.

In certain embodiments, provided is a compound of Formula Ib:

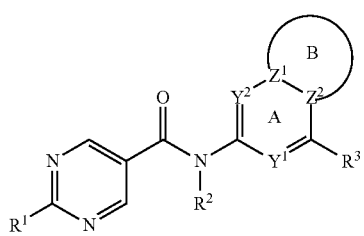

Ib or an isotopically enriched analog, pharmaceutically acceptable salt, prodrug, tautomer, stereoisomer, or a mixture of stereoisomers thereof, wherein Ring A, Ring B, $R^1$, $R^2$, $R^3$, $Y^1$, $Y^2$, $Z^1$, and $Z^2$ are as defined herein.

In certain embodiments, provided is a compound of Formula Ic:

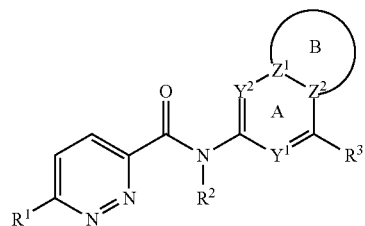

Ic or an isotopically enriched analog, pharmaceutically acceptable salt, prodrug, tautomer, stereoisomer, or a mixture of stereoisomers thereof, wherein Ring A, Ring B, $R^1$, $R^2$, $R^3$, $Y^1$, $Y^2$, $Z^1$, and $Z^2$ are as defined herein.

In certain embodiments, provided is a compound of Formula IIa:

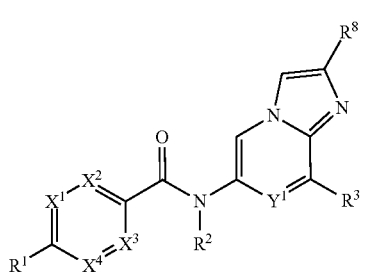

IIa or an isotopically enriched analog, pharmaceutically acceptable salt, prodrug, tautomer, stereoisomer, or a mixture of stereoisomers thereof, wherein $R^1$, $R^2$, $R^3$, $X^1$, $X^2$, $X^3$, $X^4$, and $Y^1$ are as defined herein, and wherein $R^8$ is hydrogen, halo, hydroxy, $C_{1-6}$alkyl, $C_{1-6}$haloalkyl, $C_{1-6}$alkoxy, or $C_{1-6}$haloalkoxy.

In certain embodiments, provided is a compound of Formula IIa, wherein $R^1$, $R^2$, $R^3$, $X^1$, $X^2$, $X^3$, and $X^4$ are as defined herein, $Y^1$ is $CR^5$; $R^5$ is as defined herein; and $R^8$ is hydrogen, halo, hydroxy, $C_{1-6}$ alkyl, $C_{1-6}$haloalkyl, $C_{1-6}$alkoxy, or $C_{1-6}$haloalkoxy.

In certain embodiments, provided is a compound of Formula IIb:

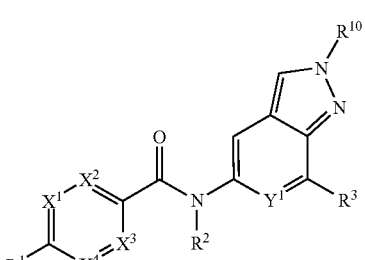

IIb or an isotopically enriched analog, pharmaceutically acceptable salt, prodrug, tautomer, stereoisomer, or a mixture of stereoisomers thereof, wherein $R^1$, $R^2$, $R^3$, $X^1$, $X^2$, $X^3$, $X^4$, and $Y^1$ are as defined herein, and wherein $R^{10}$ is hydrogen, $C_{1-6}$alkyl, or $C_{1-6}$haloalkyl.

In certain embodiments, provided is a compound of Formula IIb, wherein $R^1$, $R^2$, $R^3$, $X^1$, $X^2$, $X^3$, and $X^4$ are as defined herein, $Y^1$ is $CR^5$; $R^5$ is heterocyclyloxy or $C_{1-6}$alkoxy substituted with $C_{2-6}$alkynyl, aryl, $C_{1-6}$alkoxy, heteroaryl, heterocyclyl, or cyano; and $R^{10}$ is hydrogen, $C_{1-6}$alkyl, or $C_{1-6}$haloalkyl.

In certain embodiments, provided is a compound of Formula IIIa:

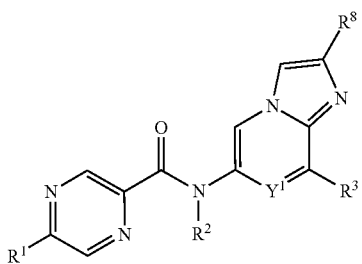

IIIa or an isotopically enriched analog, pharmaceutically acceptable salt, prodrug, tautomer, stereoisomer, or a mixture of stereoisomers thereof, wherein $R^1$, $R^2$, $R^3$, and $Y^1$ are as defined herein, and wherein $R^8$ is hydrogen, halo, hydroxy, $C_{1-6}$alkyl, $C_{1-6}$haloalkyl, $C_{1-6}$alkoxy, or $C_{1-6}$haloalkoxy.

In certain embodiments, provided is a compound of Formula IIIb:

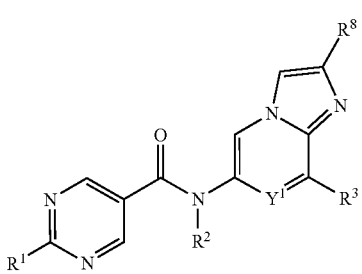

IIIb or an isotopically enriched analog, pharmaceutically acceptable salt, prodrug, tautomer, stereoisomer, or a mixture of stereoisomers thereof, wherein $R^1$, $R^2$, $R^3$, and $Y^1$ are as defined herein, and wherein $R^8$ is hydrogen, halo, hydroxy, $C_{1-6}$alkyl, $C_{1-6}$haloalkyl, $C_{1-6}$alkoxy, or $C_{1-6}$haloalkoxy.

In certain embodiments, provided is a compound of Formula IIIc:

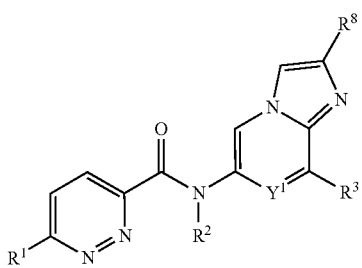

IIIc or an isotopically enriched analog, pharmaceutically acceptable salt, prodrug, tautomer, stereoisomer, or a mixture of stereoisomers thereof, wherein $R^1$, $R^2$, $R^3$, and $Y^1$ are as defined herein, and wherein $R^8$ is hydrogen, halo, hydroxy, $C_{1-6}$alkyl, $C_{1-6}$haloalkyl, $C_{1-6}$alkoxy, or $C_{1-6}$haloalkoxy.

In certain embodiments, $R^{11}$ is heterocyclyl optionally substituted with 1 to 4 groups independently selected from halo, $C_{1-6}$alkyl, $C_{1-6}$haloalkyl, $C_{3-10}$cycloalkyl, heteroaryl, heterocyclyl, heterocyclyl-$C_{1-6}$alkyl, —NH$_2$, —NHR$^{14}$, —N(R$^{14}$)$_2$, —C$_{1-6}$alkylene-NH$_2$, —C$_{1-6}$alkylene-NHR$^{14}$, —C$_{1-6}$alkylene-N(R$^{14}$)$_2$, and —C(O)OR$^{15}$; wherein each $R^{14}$ is independently selected from $C_{1-6}$alkyl, $C_{3-10}$cycloalkyl, and heterocyclyl, and each $R^{14}$ is optionally substituted with one to three halo; and wherein $R^{15}$ is $C_{1-6}$alkyl.

In certain embodiments, $R^{11}$ is heterocyclyl optionally substituted with 1 to 4 groups independently selected from $C_{1-6}$alkyl, heterocyclyl-$C_{1-6}$alkyl optionally substituted with $R^{16}$, and —NHR$^{14}$; wherein each $R^{14}$ is independently selected from $C_{1-6}$alkyl and $C_{3-10}$cycloalkyl.

In certain embodiments, $R^{11}$ is optionally substituted with 1 to 4 groups independently selected from cyclopropylamino, methyl, (3-(2-((2-(3-(2-azidoethyl)-3H-diazirin-3-yl)ethyl)amino)-2-oxoethoxy)azetidin-1-yl)methyl, and methylamino.

In certain embodiments, $R^{11}$ is

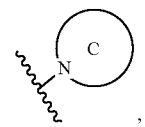

wherein Ring C is a 3- to 10-membered heterocyclyl containing 0, 1 or 2 additional ring nitrogen atoms optionally substituted with 1 to 4 $R^{13}$ groups.

In certain embodiments, Ring C is a 5- to 10-membered bicyclic heterocyclyl containing one additional ring nitrogen atom optionally substituted with 1 to 4 $R^{13}$ groups.

In certain embodiments, Ring C is a 5- to 10-membered spirobicyclic heterocyclyl containing one additional ring nitrogen atom optionally substituted with 1 to 4 $R^{13}$ groups.

In certain embodiments, Ring C is a 5- to 10-membered fused bicyclic heterocyclyl containing one additional ring nitrogen atom optionally substituted with 1 to 4 $R^{13}$ groups.

In certain embodiments $R^1$ is selected from

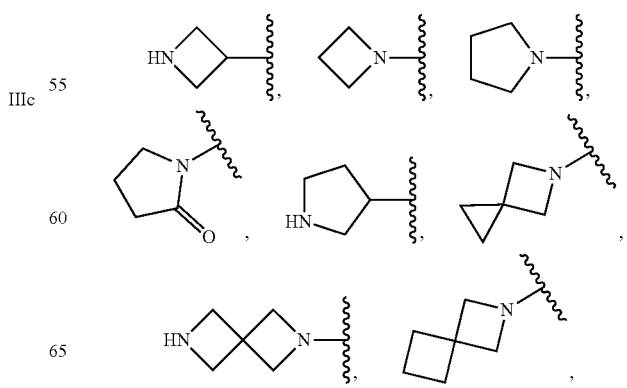

-continued

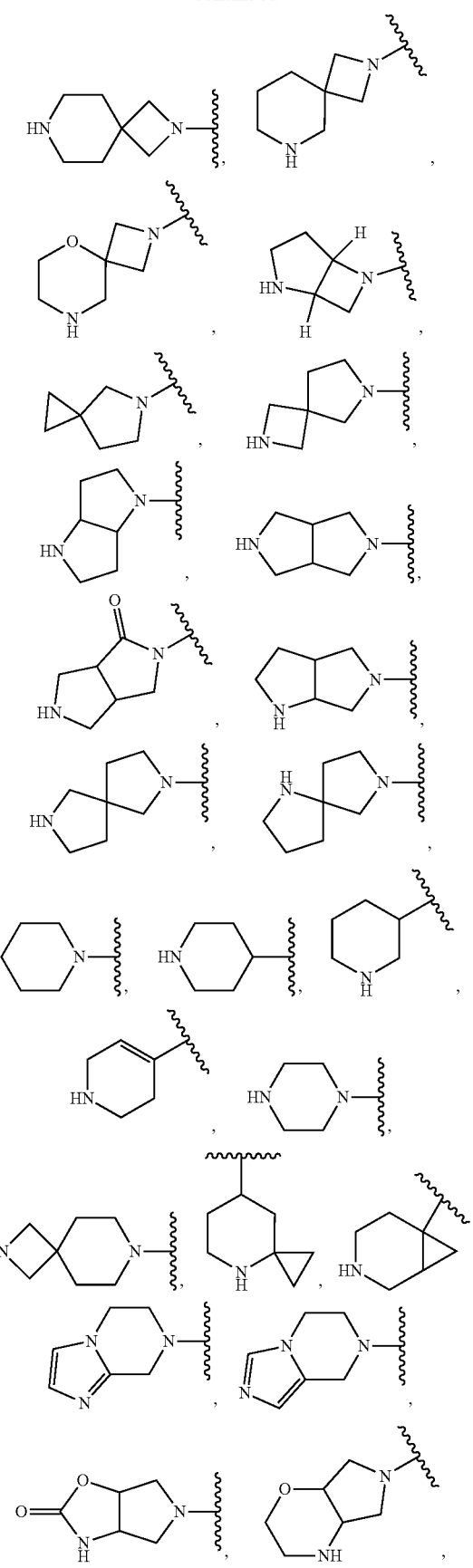

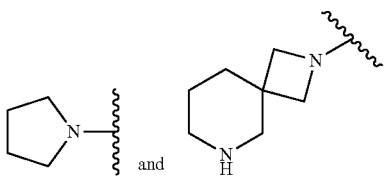

each of which is optionally substituted with 1 to 4 $R^{13}$ groups.

In certain embodiments, $R^{11}$ is selected from

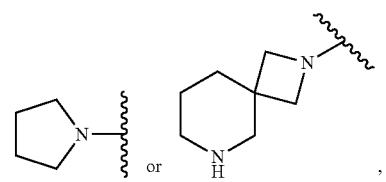

each of which is optionally substituted with 1 to 4 $R^{13}$ groups.

In certain embodiments, $R^3$ is halo. In certain embodiments, $R^3$ is hydrogen.

In certain embodiments, each $R^4$ is hydrogen.

In certain embodiments, $R^{11}$ is each of which is optionally substituted with 1 to 4 $R^{13}$ groups; and $R^5$ is heterocyclyloxy, or $C_{1-6}$alkoxy substituted with $C_{2-6}$alkynyl, aryl, $C_{1-6}$alkoxy, heteroaryl, heterocyclyl, or cyano.

In certain embodiments, $R^5$ is heterocyclyloxy or $C_{1-6}$alkoxy substituted with $C_{2-6}$alkynyl, aryl, $C_{1-6}$alkoxy, heteroaryl, heterocyclyl, or cyano In certain embodiments, $R^5$ is heterocyclyloxy.

In certain embodiments, $R^5$ is $C_{1-6}$alkoxy substituted with $C_{2-6}$alkynyl, aryl, $C_{1-6}$alkoxy, heteroaryl, heterocyclyl, or cyano.

In certain embodiments, $R^5$ is hydrogen.

In certain embodiments, $R^2$ is hydrogen.

In certain embodiments, $L^1$ is absent.

In certain embodiments, $Y^1$ is $CR^5$. In certain embodiments, $Y^1$ is N.

In certain embodiments, $Y^2$ is $CR^6$.

In certain embodiments, $Y^3$ is $CR^3$.

In certain embodiments, Ring B is a 5-membered heteroaryl containing 1 to 3 nitrogen atoms.

In certain embodiments, Ring B is

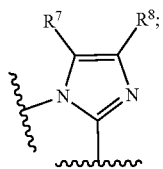

$R^7$ is hydrogen; and $R^8$ is $C_{1-6}$alkyl. In certain embodiments, Ring B is

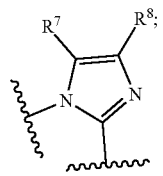

$R^7$ is hydrogen; and $R^8$ is $C_{1-3}$alkyl.
In certain embodiments, Ring B is

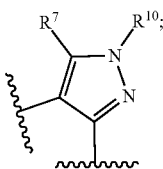

$R^7$ is hydrogen; and $R^{10}$ is $C_{1-6}$alkyl. In certain embodiments, Ring B is

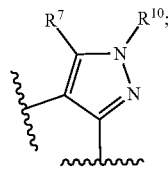

$R^7$ is hydrogen; and $R^{10}$ is $C_{1-3}$alkyl.

In certain embodiments, provided is a pharmaceutical composition comprising a compound described herein, or an isotopically enriched analog, pharmaceutically acceptable salt, prodrug, tautomer, stereoisomer, or a mixture of stereoisomers thereof, and a pharmaceutically acceptable excipient.

In certain embodiments, provided is a method for treating Huntington's disease in a patient in need thereof, comprising administering to the patient a therapeutically effective amount of a compound or a pharmaceutical composition described herein.

In certain embodiments, provided is a method for treating Huntington's disease in a patient in need thereof, comprising administering to the patient a therapeutically effective amount of a compound or pharmaceutical composition described herein in combination with a second active agent.

Also is provided a compound, or an isotopically enriched analog, pharmaceutically acceptable salt, prodrug, tautomer, stereoisomer, or a mixture of stereoisomers thereof, selected from Table 1:

TABLE 1

| Ex. | Structure | MS Detected |
|---|---|---|
| 1 | 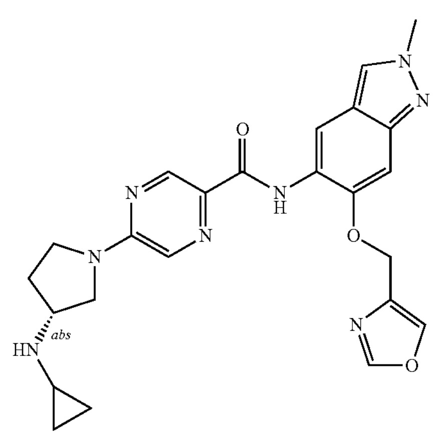 [SMILES: Cn1cc2cc(NC(=O)c3cnc(N4CC[C@@H](NC5CC5)C4)cn3)c(OCc3cocn3)cc2n1] | 475.2 |

TABLE 1-continued

| Ex. | Structure | MS Detected |
|---|---|---|
| 2 | 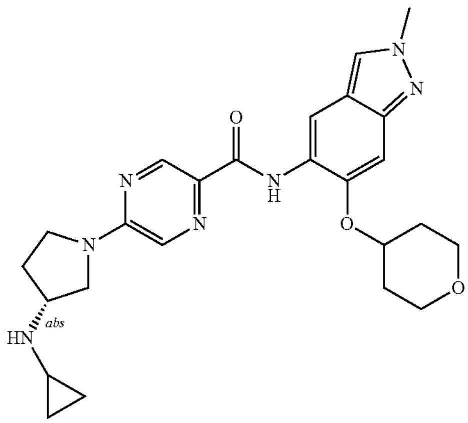 [SMILES: Cn1cc2cc(NC(=O)c3cnc(N4CC[C@@H](NC5CC5)C4)cn3)c(OC3CCOCC3)cc2n1] | 478.2 |
| 3 | 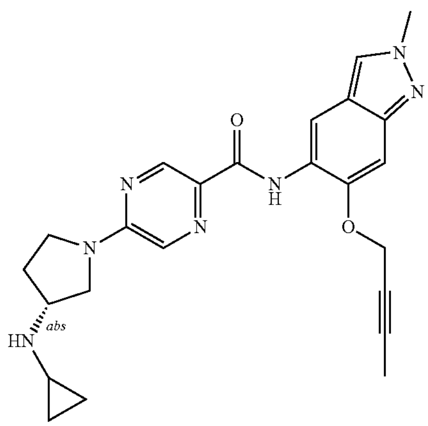 [SMILES: CC#CCOc1cc2nn(C)cc2cc1NC(=O)c1cnc(N2CC[C@@H](NC3CC3)C2)cn1] | 446.2 |
| 4 | 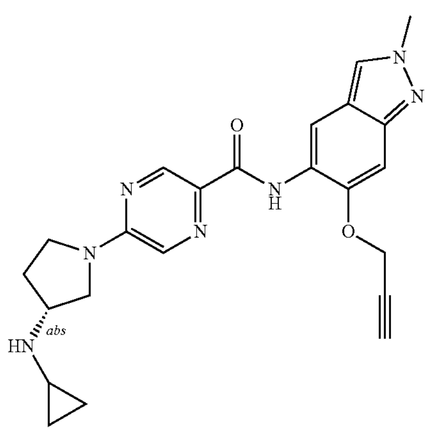 [SMILES: C#CCOc1cc2nn(C)cc2cc1NC(=O)c1cnc(N2CC[C@@H](NC3CC3)C2)cn1] | 406.2 |

TABLE 1-continued
| Ex. | Structure | MS Detected |
|---|---|---|
| 5 | 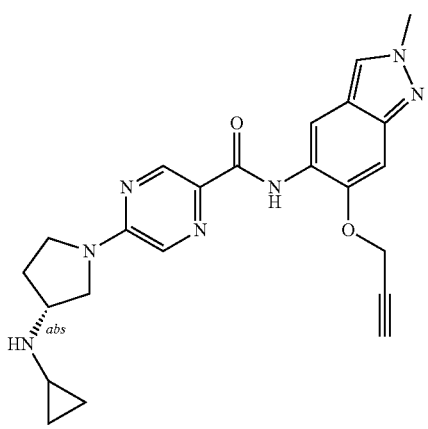 [SMILES: C#CCOc1cc2nn(C)cc2cc1NC(=O)c1cnc(N2CC[C@@H](NC3CC3)C2)cn1] | 432.2 |
| 6 | 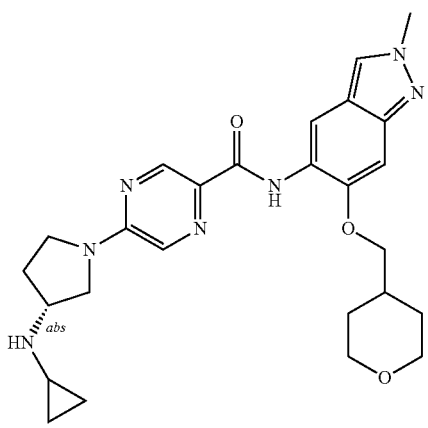 [SMILES: Cn1cc2cc(NC(=O)c3cnc(N4CC[C@@H](NC5CC5)C4)cn3)c(OCC3CCOCC3)cc2n1] | 492.5 |
| 7 | 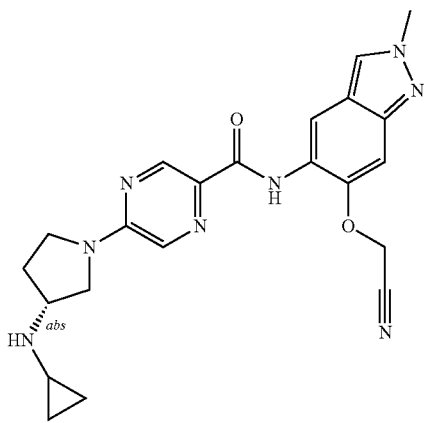 [SMILES: Cn1cc2cc(NC(=O)c3cnc(N4CC[C@@H](NC5CC5)C4)cn3)c(OCC#N)cc2n1] | 433.5 |

TABLE 1-continued

| Ex. | Structure | MS Detected |
|---|---|---|
| 8 | 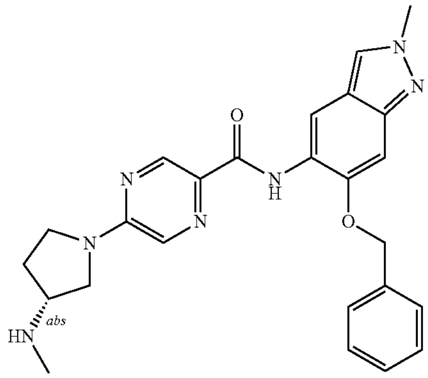 [SMILES: CN[C@@H]1CCN(c2cnc(C(=O)Nc3cc4cn(C)nc4cc3OCc3ccccc3)cn2)C1] | 458.2 |
| 9 | 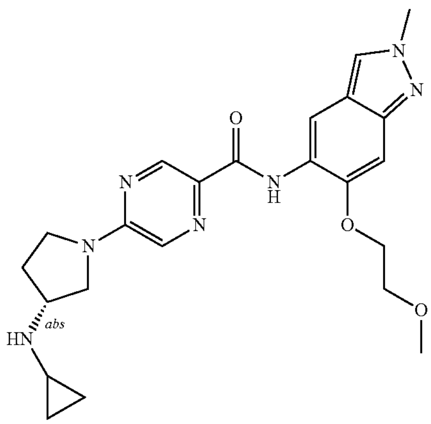 [SMILES: COCCOc1cc2nn(C)cc2cc1NC(=O)c1cnc(N2CC[C@@H](NC3CC3)C2)cn1] | 452.5 |
| 10 | 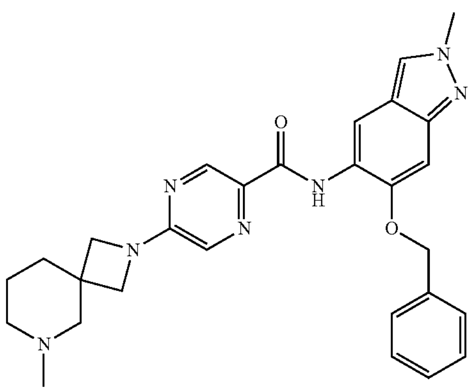 [SMILES: CN1CCCC2(C1)CN(c1cnc(C(=O)Nc3cc4cn(C)nc4cc3OCc3ccccc3)cn1)C2] | 498.2 |
| 11 | 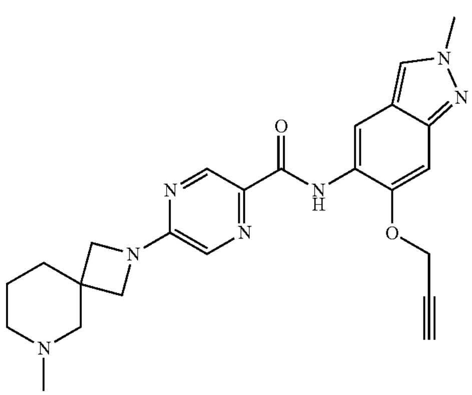 [SMILES: C#CCOc1cc2nn(C)cc2cc1NC(=O)c1cnc(N2CC3(CCCN(C)C3)C2)cn1] | 446.2 |

TABLE 1-continued
| Ex. | Structure | MS Detected |
|---|---|---|
| 45 | 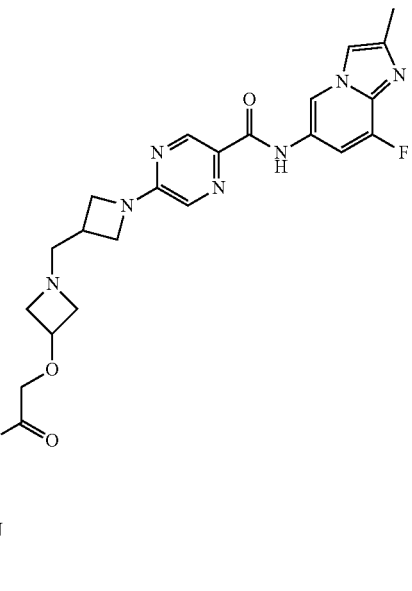 | 606.2 |
Also is provided a compound, or an isotopically enriched analog, pharmaceutically acceptable salt, prodrug, tautomer, stereoisomer, or a mixture of stereoisomers thereof, selected from Table 2:
TABLE 2
| Ex. | Structure | MS Detected |
|---|---|---|
| 12 | 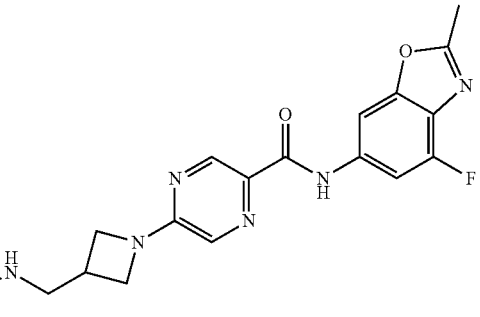 | 399.5 |
| 13 | 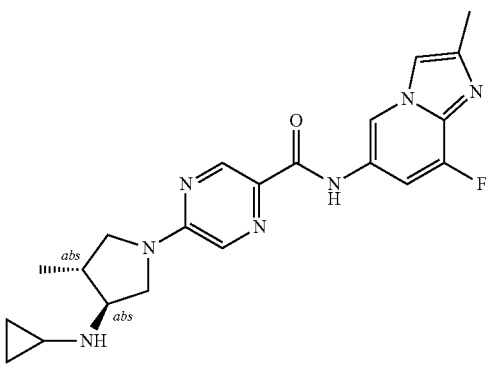 [SMILES: Cc1cn2cc(NC(=O)c3cnc(N4C[C@@H](C)[C@H](NC5CC5)C4)cn3)cc(F)c2n1] | 410.4 |

TABLE 2-continued

| Ex. | Structure | MS Detected |
|---|---|---|
| 14 | 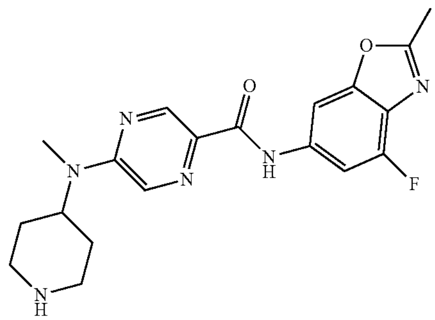 [SMILES: Cc1nc2c(F)cc(NC(=O)c3cnc(N(C)C4CCNCC4)cn3)cc2o1] | 385.4 |
| 15 | 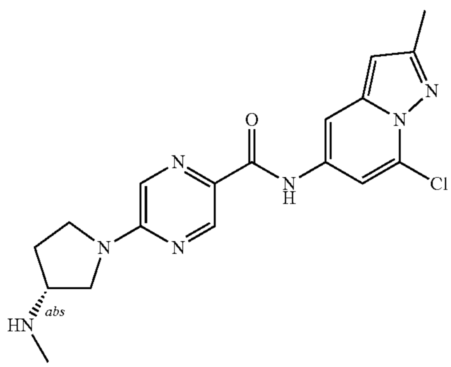 [SMILES: CN[C@@H]1CCN(c2cnc(C(=O)Nc3cc(Cl)n4nc(C)cc4c3)cn2)C1] | 386.2 |
| 16 | 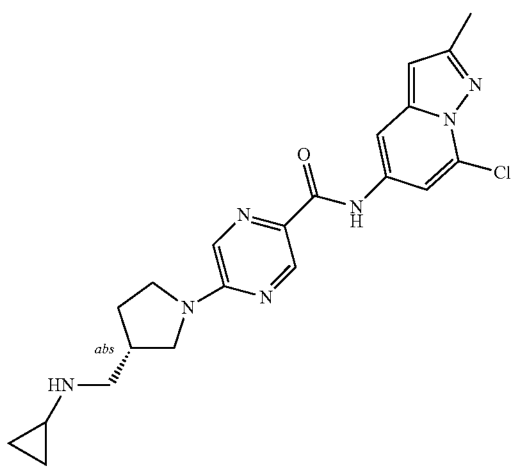 [SMILES: Cc1cc2cc(NC(=O)c3cnc(N4CC[C@@H](CNC5CC5)C4)cn3)cc(Cl)n2n1] | 426.2 |
| 17 | 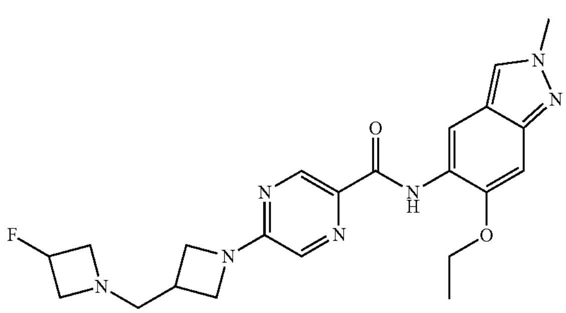 [SMILES: CCOc1cc2nn(C)cc2cc1NC(=O)c1cnc(N2CC(CN3CC(F)C3)C2)cn1] | 440.2 |

TABLE 2-continued
| Ex. | Structure | MS Detected |
|---|---|---|
| 18 | 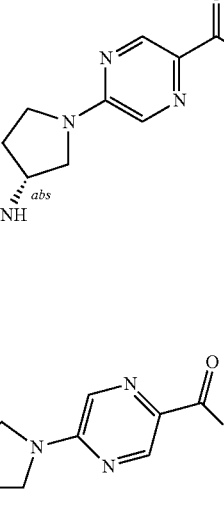 | 444.2 |
| 19 | 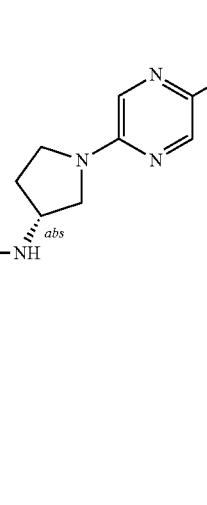 | 371.4 |
| 20 | 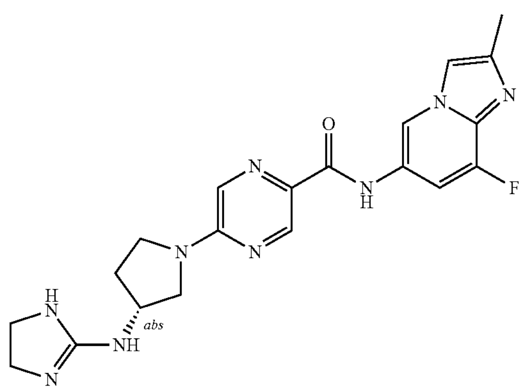 [SMILES: Cc1cn2cc(NC(=O)c3cnc(N4CC[C@@H](NC5=NCCN5)C4)cn3)cc(F)c2n1] | 424.5 |
| 21 | 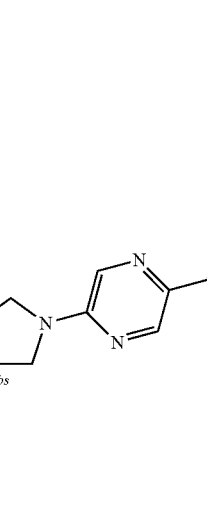 | 384.2 |

TABLE 2-continued

| Ex. | Structure | MS Detected |
|---|---|---|
| 22 | 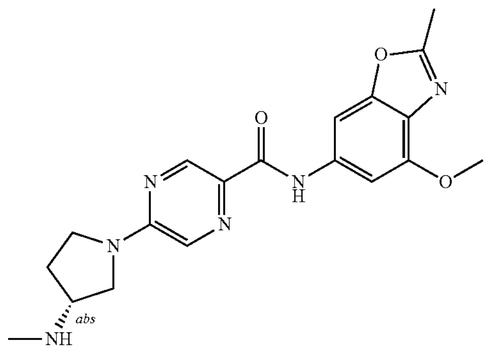 | 383.2 |
| 23 | 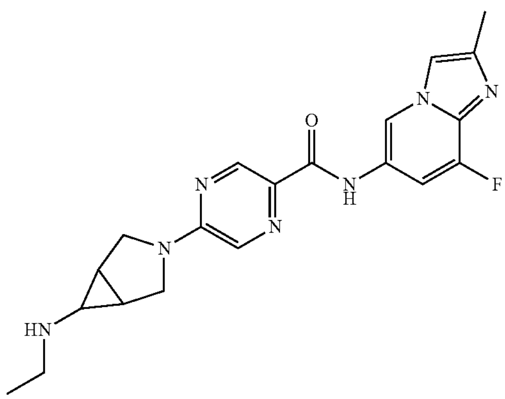 [SMILES: CCNC1C2CN(c3cnc(C(=O)Nc4cc(F)c5nc(C)cn5c4)cn3)CC21] | 396.2 |
| 24 | 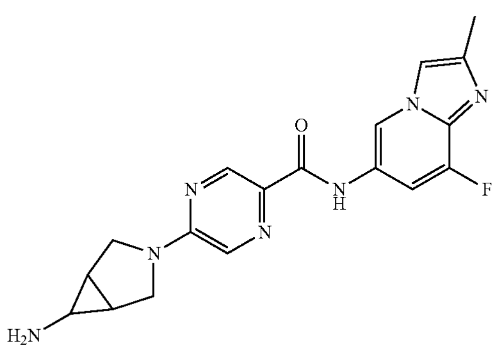 [SMILES: Cc1cn2cc(NC(=O)c3cnc(N4CC5C(N)C5C4)cn3)cc(F)c2n1] | 368.2 |
| 25 | 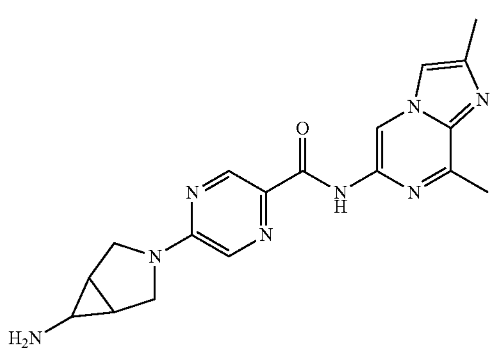 [SMILES: Cc1cn2cc(NC(=O)c3cnc(N4CC5C(N)C5C4)cn3)nc(C)c2n1] | 365.4 |

TABLE 2-continued

| Ex. | Structure | MS Detected |
|---|---|---|
| 26 | 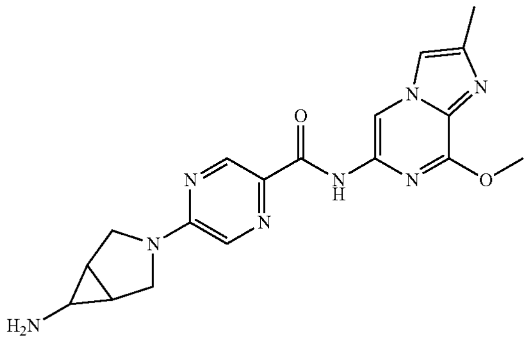 [SMILES: COc1nc(NC(=O)c2cnc(N3CC4C(N)C4C3)cn2)cn2cc(C)nc12] | 381 |
| 27 | 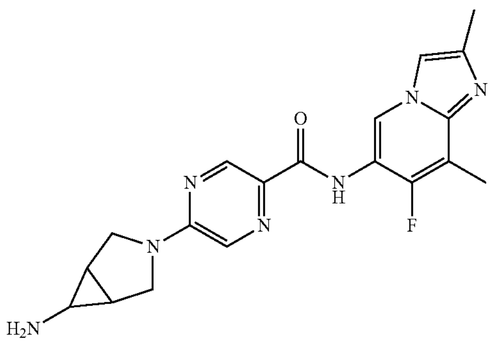 [SMILES: Cc1cn2cc(NC(=O)c3cnc(N4CC5C(N)C5C4)cn3)c(F)c(C)c2n1] | 382.2 |
| 28 | (Enantiomer 1 + Enantiomer 2) | 368 |
| 29 | 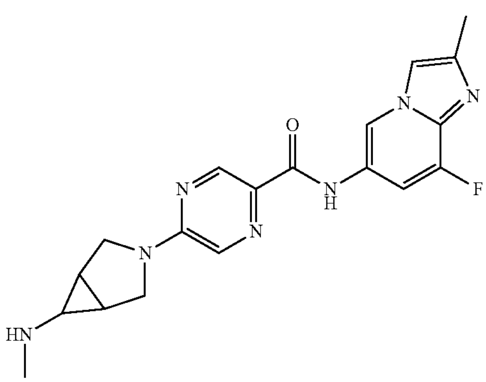 [SMILES: CNC1C2CN(c3cnc(C(=O)Nc4cc(F)c5nc(C)cn5c4)cn3)CC21] | 382.4 |

TABLE 2-continued

| Ex. | Structure | MS Detected |
|---|---|---|
| 30 | 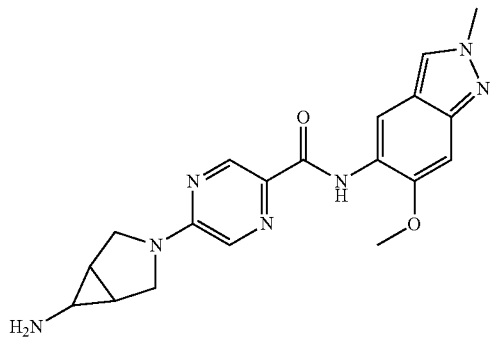 [SMILES: COc1cc2nn(C)cc2cc1NC(=O)c1cnc(N2CC3C(N)C3C2)cn1] | 380.4 |
| 31 | 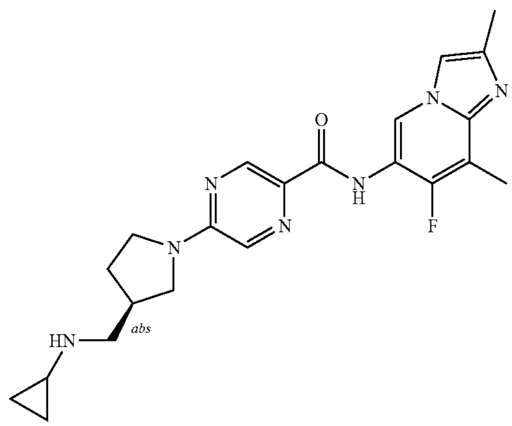 [SMILES: Cc1cn2cc(NC(=O)c3cnc(N4CC[C@H](CNC5CC5)C4)cn3)c(F)c(C)c2n1] | 424.4 |
| 32 | 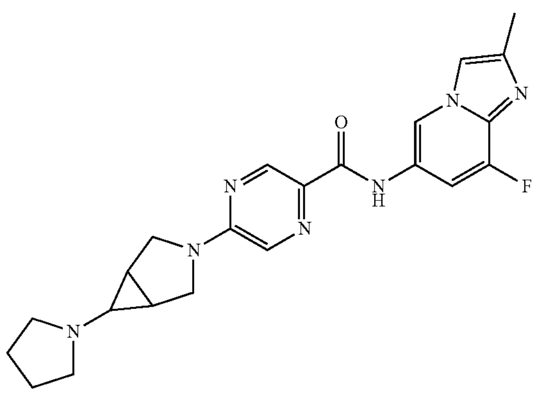 [SMILES: Cc1cn2cc(NC(=O)c3cnc(N4CC5C(C4)C5N4CCCC4)cn3)cc(F)c2n1] | 422.2 |
| 33 | 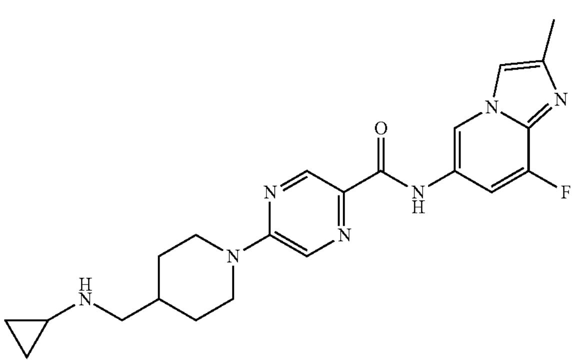 [SMILES: Cc1cn2cc(NC(=O)c3cnc(N4CCC(CNC5CC5)CC4)cn3)cc(F)c2n1] | 424.4 |

TABLE 2-continued

| Ex. | Structure | MS Detected |
|---|---|---|
| 34 | 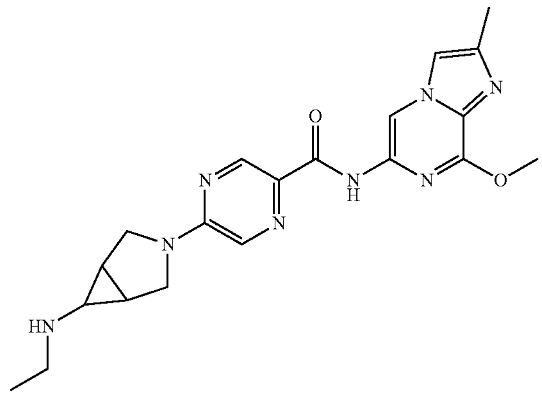 [SMILES: CCNC1C2CN(c3cnc(C(=O)Nc4cn5cc(C)nc5c(OC)n4)cn3)CC21] | 409.2 |
| 35 | Enantiomer 2 | 368.2 |
| 36 | Enantiomer 1 | 368.4 |
| 37 | 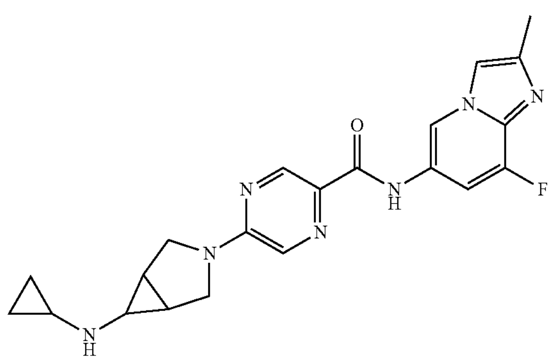 [SMILES: Cc1cn2cc(NC(=O)c3cnc(N4CC5C(C4)C5NC4CC4)cn3)cc(F)c2n1] | 408.2 |

TABLE 2-continued
| Ex. | Structure | MS Detected |
|---|---|---|
| 38 | 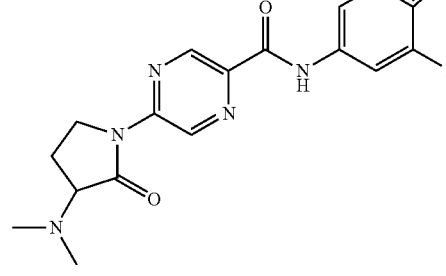 Enantiomer 2 | 398.2 |
| 39 | 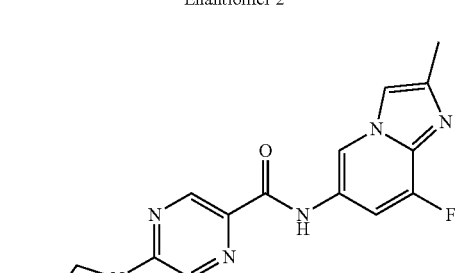 Enantiomer 1 | 398.2 |
| 40 | 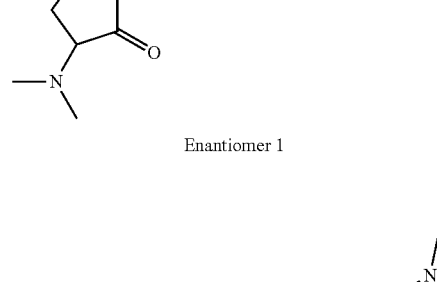 Enantiomer 1 | 424.2 |
| 41 | 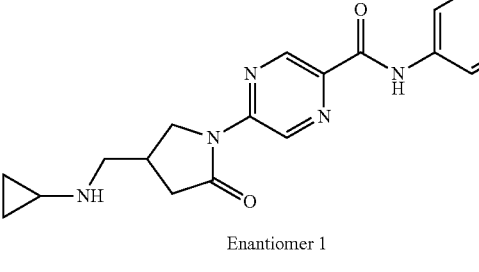 Enantiomer 2 | 424.2 |

TABLE 2-continued
| Ex. | Structure | MS Detected |
|---|---|---|
| 42 | 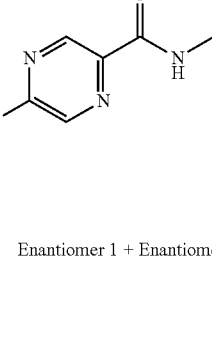<br>Enantiomer 1 + Enantiomer 2 | 370.5 |
| 43 | 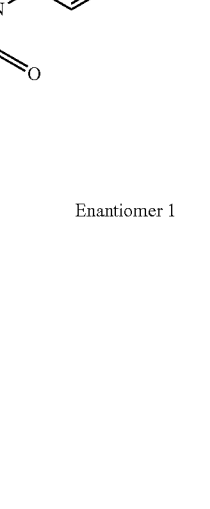<br>Enantiomer 1 | 410.3 |
| 44 | 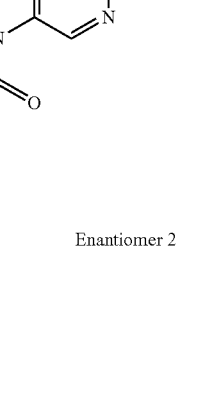<br>Enantiomer 2 | 410.4 |

TABLE 2-continued
| Ex. | Structure | MS Detected |
|---|---|---|
| 46 | 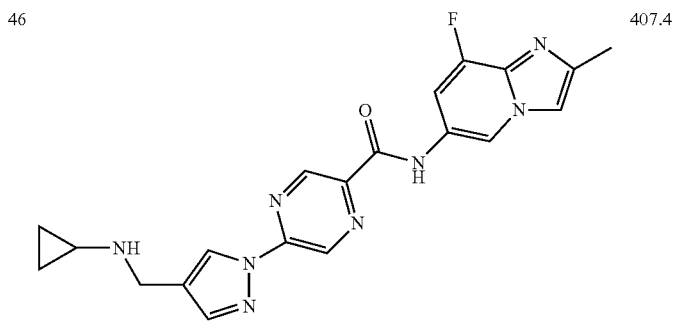 | 407.4 |
| 47 | 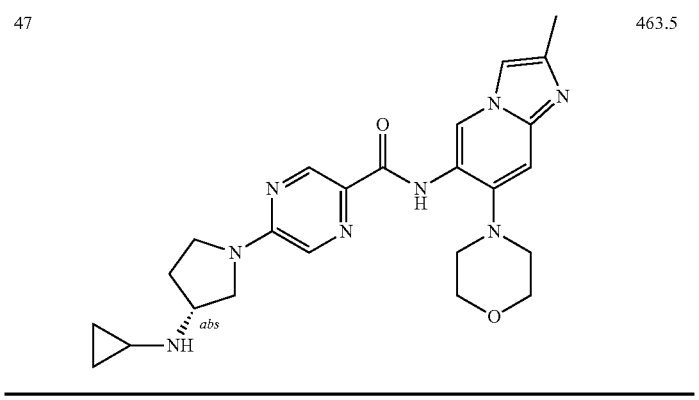 | 463.5 |

Also is provided a compound, or an isotopically enriched analog, pharmaceutically acceptable salt, prodrug, tautomer, stereoisomer, or a mixture of stereoisomers thereof, selected from Table 2A:
TABLE 2A
Structure
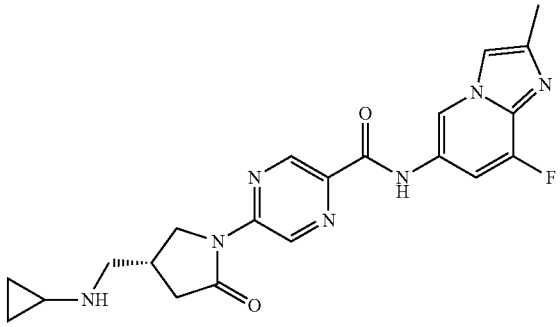 [SMILES: Cc1cn2cc(NC(=O)c3cnc(N4C[C@@H](CNC5CC5)CC4=O)cn3)cc(F)c2n1]
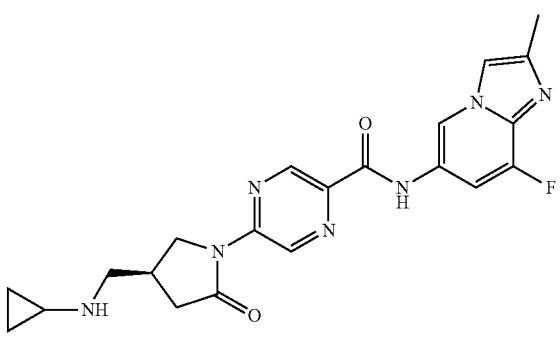 [SMILES: Cc1cn2cc(NC(=O)c3cnc(N4C[C@H](CNC5CC5)CC4=O)cn3)cc(F)c2n1]
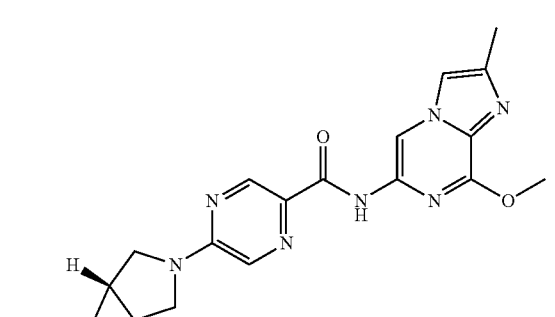
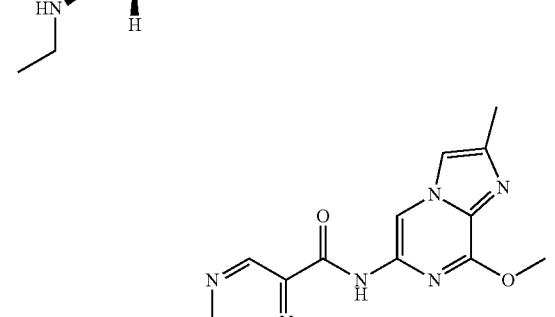
TABLE 2A-continued
Structure
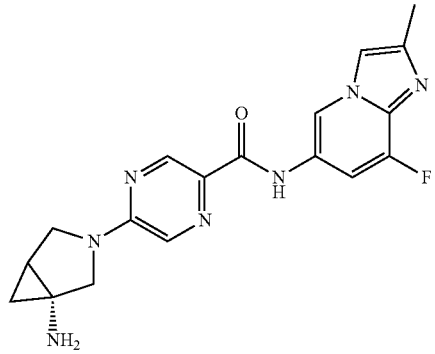 [SMILES: Cc1cn2cc(NC(=O)c3cnc(N4CC5C[C@]5(N)C4)cn3)cc(F)c2n1]
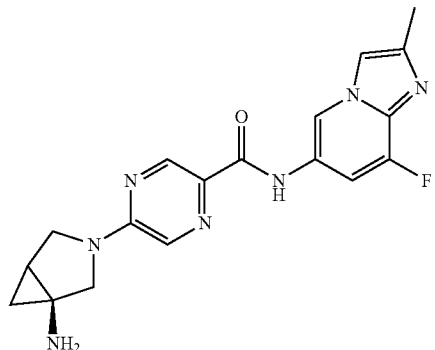
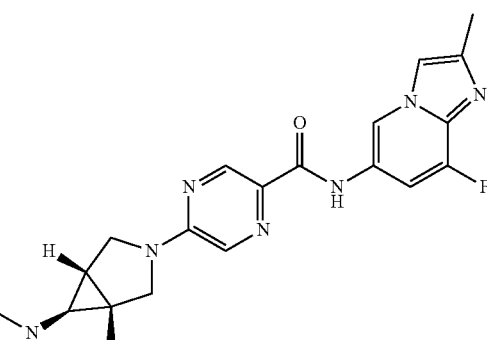

TABLE 2A-continued
| Structure |
|---|
| 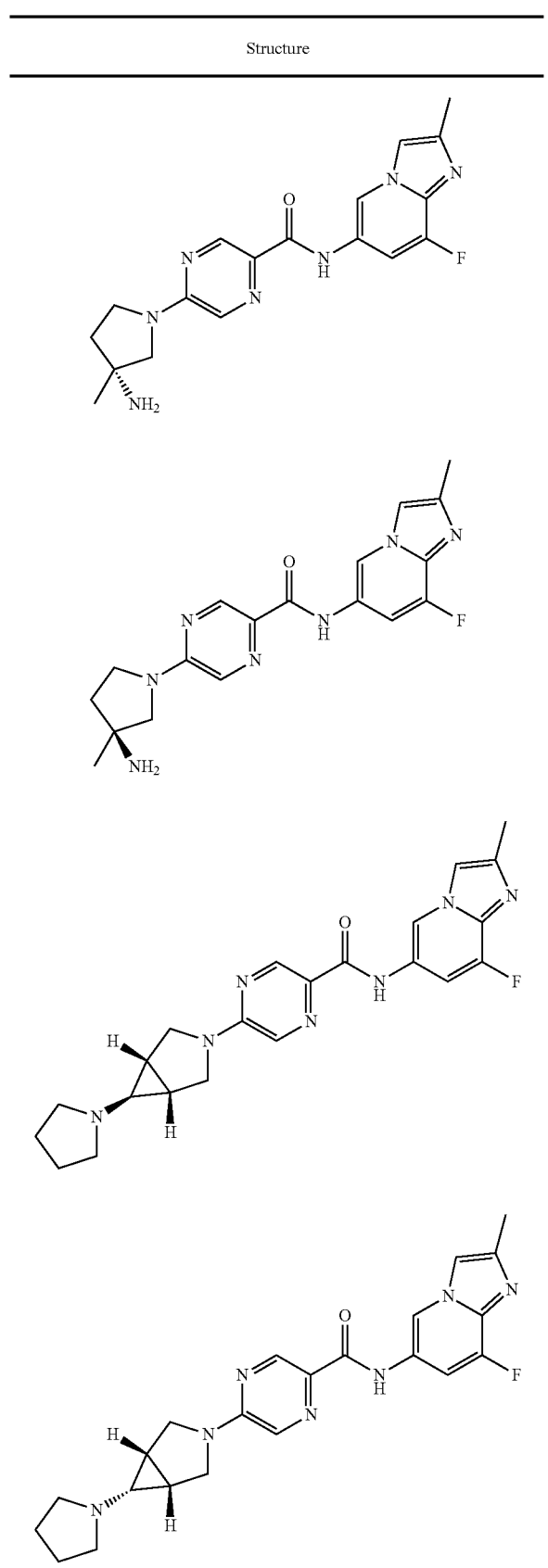 |
| 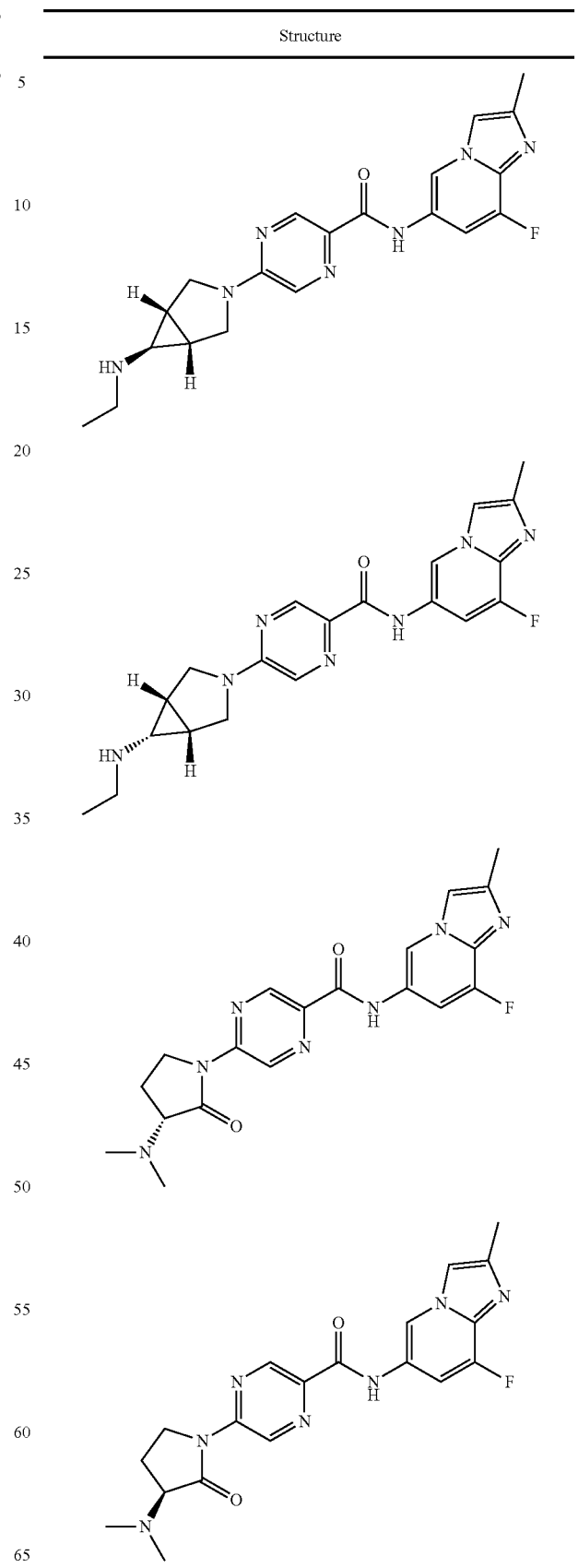 |

TABLE 2A-continued

Structure

TABLE 2A-continued

Structure

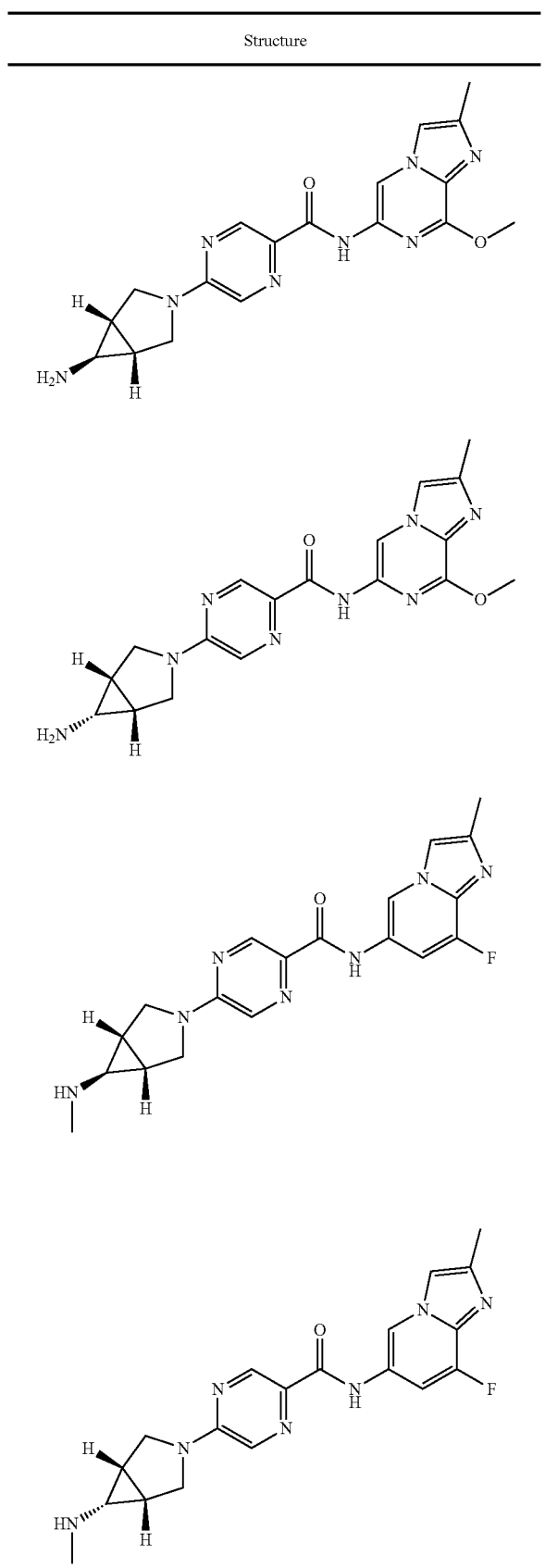

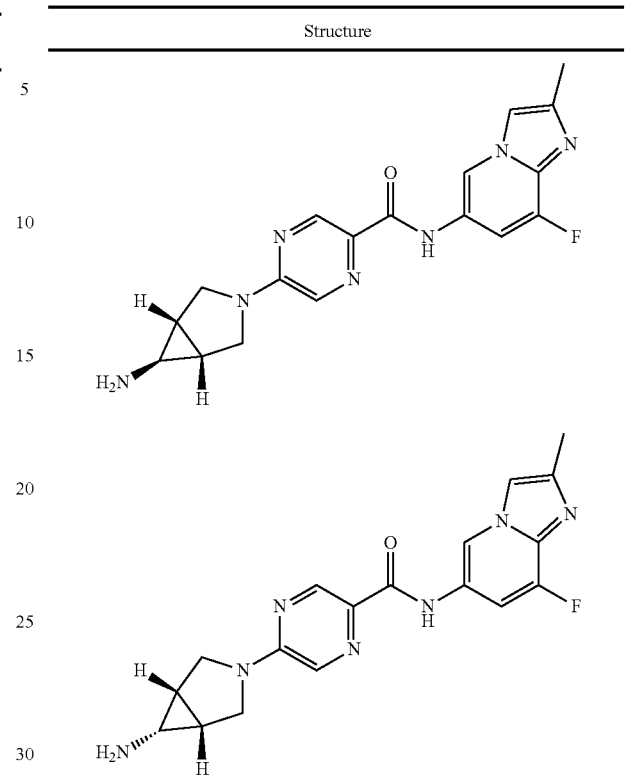

Indications and Treatment Methods

A compound described herein may be useful for treating a disease or condition mediated, at least in part, by a protein implicated in neurodegenerative disease. In some embodiments, a compound described herein is useful for detecting diseases or conditions mediated, at least in part, by HTT protein. In some embodiments, treatment of a disease or condition mediated, at least in part, by a protein implicated in neurodegenerative disease may comprise administration of a compound described herein. Treatment may include coadministration of a compound described herein and one or more other active agents and/or therapies.

In some embodiments, provided is a method of treating or preventing a disease or condition mediated, at least in part, by a protein implicated in neurodegenerative disease in a patient in need thereof, comprising administering to the patient a therapeutically effective amount of a compound described herein.

Exemplary diseases or conditions are as follows.

Huntington's Disease (HD)

Huntington's disease (HD) is an inherited progressive neurodegenerative condition, characterized by motor, cognitive, and psychiatric deficits as well as neurodegeneration and brain atrophy. Atrophy may begin in the striatum and cortex and extend to other subcortical brain regions. HD belongs to a family of neurodegenerative diseases in which an expanded CAG repeat tract results in long stretches of polyglutamine (polyQ) in an encoded protein. The family also includes dentatorubral-pallidoluysian atrophy (DR-PLA), spinal and bulbar muscular atrophy (SBMA) and the spinocerebellar ataxias (SCAs). In HD, the selective neurodegeneration of the γ-aminobutyric acid-releasing spiny-projection neurons of the striatum has been observed, although neuron loss in many other brain regions has also been reported. Symptoms of HD include loss of motor control, psychiatric symptoms, memory, and/or cognitive impairment.

Huntingtin protein (HTT protein) is a 348-kDa multidomain protein that contains a polymorphic glutamine/proline-rich domain at its amino-terminus. The number of CAG repeats in the $IT_{15}$ gene that encodes them varies from 6 to 35 in healthy individuals; repeats of 36 or more define an HD allele. The length of the CAG expansion has been inversely correlated with age of disease onset, with cases of juvenile onset characterized by expansions of more than 60 repeats. Reduced penetrance is seen between 36 and 39 repeats. See McColgan P, et al., Huntington's disease: a clinical review, Eur. J. Neurology, 2017, Vol. 25, 24-34, which is incorporated by reference herein in its entirety. The longer polyQ domain is believed to induce conformational changes in the HTT protein, which causes it to form intracellular aggregates that, in many, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum, and mitochondria.

A diagnosis of Huntington's disease is based on a confirmed family history or positive genetic test and the onset of motor disturbance as defined by the Unified HD Rating Scale (UHDRS) total motor score (TMS) diagnostic confidence score. This score ranges from 0 (no motor abnormalities suggestive of HD) to 4 (≥99% to be due to HD), with a score of 4 defining motor onset or 'manifest' HD. However, subtle motor, cognitive and psychiatric deficits can be identified up to 10-15 years before the onset of manifest disease and this is referred to as the pre-manifest stage of the disease.

Huntington's disease (HD) stages are described in, e.g., Winder, J. Y. et al., Assessment Scales for Patients with Advanced Huntington's Disease: Comparison of the UHDRS and UHDRS-FAP, Mov Disord Clin Pract. 2018 September-October; 5(5): 527-533, which is incorporated by reference herein in its entirety. HD may be classified as early stage (stage 1 or 2 Total Function Capacity (TFC) score), mid stage (stage 3 TFC score), or late stage (stage 4 or 5 TFC score). See, e.g., Shoulson, I. et al., Huntington disease: Clinical care and evaluation, Neurology, 1979, Vol. 29(1), 1; Shoulson, I., Huntington disease: functional capacities in patients treated with neuroleptic and antidepressant drugs, Neurology, 1981, Vol. 31(10), 1333-35. A new framework (HD-ISS) was published recently that stages HD based on biological, clinical, and functional assessments (Tabrizi et al, Huntington's Disease Regulatory Science Consortium (HD-RSC), A biological classification of Huntington's disease: the Integrated Staging System. Lancet Neurol. 2022, 21, 632-644). The part of the brain most affected by HD, and thus believed to be most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

Basal ganglia are a group of subcortical nuclei responsible primarily for motor control, as well as other roles, such as motor learning, executive functions and behaviors, and emotions. Disruption of the basal ganglia network are believed to contribute to several movement disorders. Normal function of the basal ganglia requires fine tuning of neuronal excitability within each nucleus to determine the degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

A compound described herein, when administered to a subject, may inhibit neuron degeneration. In some embodiments, inhibiting neuron degeneration may include inhibiting axon or neuron degeneration in a neuron. Such inhibition with respect to the entire neuron or a portion thereof, such as the neuron cell body, axons and dendrites. This can be assessed, for example, by analysis of neurological function according to methods known in the art.

The administration of a compound described herein may result in a rescue, for example, at least a 10% reduction (e.g., at least 15%, 20%, 25%, 30%, 35%, 40%, 45%, 50%, 55%, 60%, 65%, 70%, 75%, 80%, 85%, 90% or 100%) in one or more symptoms of a disease or condition described herein. The disease or condition may be a disorder of the nervous system that is secondary to a disease, condition, or therapy having a primary effect outside of the nervous system; an injury to the nervous system caused by physical, mechanical or chemical trauma; autoimmune neural degeration; neurodegeneration secondary to infection; and/or ocular neurodegeneration. Symptoms of nerve degeneration include, e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity.

The administration of a compound described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or 100%) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the compounds described herein.

Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the disclosure include cerebellar granule neurons, dorsal root ganglion neurons, PNS neurons (e.g. sensory neurons), and cortical neurons. Other examples of cell types that may be subject to treatment according to the disclosure include astrocytes and microglia.

A neurodegenerative disease is a disease or condition in which the function of a subject's nervous system becomes impaired. Examples of neurodegenerative diseases include, e.g., Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion disease, Refsum's disease, Sandhoff disease, Schilder's disease, Subacute combined degeneration of spinal cord secondary to Pernicious Anaemia, Schizophrenia, Spinocerebellar ataxia, Spinal muscular atrophy, Steele-Richardson-Olszewski disease, insulin resistance, or Tabes dorsalis.

In some embodiments, the disease or condition is selected from Huntington's disease (HD), dentatorubropallidoluysian atrophy, spinal and bulbar muscular atrophy, spinocerebellar ataxia, spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma.

Further, the compounds described herein can be used in the prevention or treatment of memory loss. Types of memory that can be affected by loss, and thus treated according to the disclosure, include episodic memory, semantic memory, short-term memory, and long-term memory.

In some embodiments, the disease or condition is a neurodegenerative disease selected from Alzheimer's disease, amyotrophic lateral sclerosis, Huntington's disease, Parkinson's disease, Prion disease and spinocerebellar ataxias. In some embodiments, the neurodegenerative disease is classified as a trinucleotide repeat disorder. In some embodiments, the trinucleotide repeat disorder is classified as belonging to Category I, Category II, or Category III.

In some embodiments, the neurodegenerative disease is Huntington's disease.

Also provided is use of a compound described herein for the manufacture of a medicament for use in diagnosis, prevention, or treatment of a disease or condition described herein. For example, the disease or condition may be Huntington's disease.

Pharmaceutical Compositions and Administration Thereof

Compounds provided herein may be administered in the form of a pharmaceutical composition. Thus, provided herein are also pharmaceutical compositions that contain a compound described herein and a pharmaceutically acceptable excipient.

Suitable pharmaceutically acceptable excipients may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical composition may be formulated for administration by various methods including, for example, oral, rectal, buccal, intranasal, and transdermal routes. In certain embodiments, the pharmaceutical composition may be administered by intra-arterial injection, intravenously, intraperitoneally, parenterally, intramuscularly, subcutaneously, orally, topically, or as an inhalant.

The pharmaceutical composition may be formulated for administration by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical excipients.

The pharmaceutical composition may be in the form of a sterile injectable aqueous or oleaginous suspension. This suspension may be formulated according to the known art using suitable dispersing or wetting agents and suspending agents. The sterile injectable preparation may also be a sterile injectable solution or suspension in a non-toxic parentally acceptable vehicle, for example, as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid can be useful in the preparation of injectables. Such solutions may be formulated as 0.01%-10% isotonic solutions, pH 5-7, with appropriate salts.

The compound described herein may be administered parenterally in a sterile medium. Parenteral administration includes subcutaneous injections, intravenous, intramuscular, intrathecal injection, or infusion techniques. The compound described herein, depending on the vehicle and concentration used, can either be suspended or dissolved in the vehicle. Advantageously, adjuvants such as local anesthetics, preservatives, and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

A pharmaceutical composition, for example, for injection, may comprise a cyclodextrin. The cyclodextrin may be, for example, a hydroxypropyl cyclodextrin or a sulfobutylether cyclodextrin. The cyclodextrin may be, for example, an α-cyclodextrin, a β-cyclodextrin, or a γ-cyclodextrin.

A compound described herein may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples can be found, e.g., in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

The pharmaceutical composition may be formulated for oral administration. The pharmaceutical composition may be in the form of, for example, a capsule or a tablet. The oral formulation may include an enteric coating. In making the pharmaceutical composition the compound described herein is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include, e.g., lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The pharmaceutical composition can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical composition can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. Such patches may be constructed for continuous, pulsatile, or on demand delivery of pharmaceutical agents.

For preparing solid compositions such as tablets, the compound described herein may be mixed with a pharmaceutical excipient to form a solid preformulation composition containing a homogeneous mixture. When referring to these preformulation compositions as homogeneous, the compound may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the intestine, or to be delayed in release. A variety of materials can be used for such enteric layers or coatings, such materials including a number of polymeric acids and mixtures of polymeric acids with such materials as shellac, cetyl alcohol, and cellulose acetate.

The compound described herein can be incorporated into oral liquid preparations such as aqueous or oily suspensions, solutions, emulsions, syrups, or elixirs, for example. Furthermore, pharmaceutical compositions containing the compound described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

A compound described herein, or a pharmaceutical composition thereof, may be administered in an appropriate dose as determined by an informed medical practitioner. The compound or pharmaceutical composition may be administered in a single dosage or in multiple dosages, and in a single dosage form or in a plurality of dosage forms (e.g., two tablets or three capsules). For any particular subject, an appropriate dose will depend upon a variety of factors including the activity of the specific compound employed, the age, body weight, general health, sex, diet, time of administration, route of administration, rate of excretion, active agents used in combination, and the severity of the particular disease or condition, of the subject. For example, a dose may be expressed as a number of milligrams of a compound described herein per kilogram of the subject's body weight (mg/kg) per day. A dose of about 0.1 to about 150 mg/kg may be appropriate. In some embodiments, a dose of about 0.1 to about 100 mg/kg may be appropriate. In some embodiments, a dose of from about 0.0001 to about 100 mg per kg of body weight per day, from about 0.001 to about 50 mg of compound per kg of body weight, or from about 0.01 to about 10 mg of compound per kg of body weight may be appropriate. In some embodiments, a dose may be administered in multiple administrations per day, for example, in one administration per day, two administrations per day, or three administrations per day. In some embodiments, a dose may be administered once in two days, once in three days, once in four days, or once per week. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

Kits

Also provided herein are kits that include a compound described herein and suitable packaging. In certain embodiments, a kit further includes instructions for use. In one aspect, a kit includes a compound described herein, and a label and/or instructions for use of the compound in the treatment of a disease or condition described herein.

Also provided herein are articles of manufacture that include a compound described herein in a suitable container. The container may be a vial, jar, ampoule, preloaded syringe and/or intravenous bag.

Combination Therapy

In some embodiments, a compound described herein is administered in combination with one or more additional active agents.

The methods described herein include methods for detecting, treating or preventing a disease or condition described herein, for example, Huntington's disease, comprising administering to a subject, simultaneously or sequentially, a compound described herein and one or more additional active agents. In methods using simultaneous administration, the agents can be present in a combined composition or can be administered separately. When used in combination with one or more additional active agents, a compound described herein may be administered prior to, concurrently with, or following administration of the additional active agents. The administration can be by the same route or by different routes.

Also provided is a pharmaceutical composition comprising a compound described herein and one or more additional pharmaceutical agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. Similarly, also provided is a packaged pharmaceutical composition containing a pharmaceutical composition comprising a compound described herein, and another composition comprising one or more additional pharmaceutical agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. In some embodiments, the active agent is carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, or risperidone.

Also provided are methods for treating or preventing Alzheimer's disease, including treating memory and/or cognitive impairment associated with Alzheimer's disease, comprising administering to a subject, simultaneously or sequentially, a compound described herein and one or more additional agents. In some embodiments, the active agent is Reminyl®, Cognex®, Aricept®, Exelon®, Akatinol®, Neotropin™, Eldepryl®, Estrogen, or Clioquinol.

In some embodiments, compounds described herein can be administered with an active agent for treating Parkinson's disease, for example, with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In some embodiments, compounds described herein can be administered with an active agent for treating Alzheimer's disease, for example, with acetylcholinesterase inhibitors (e.g., donepezil, galantamine, and rivastigmine) and/or NMDA receptor antagonists (e.g., memantine).

Synthesis of the Compounds

A compound described herein may be prepared using the methods disclosed herein and routine modifications thereof, which will be apparent given the disclosure herein and methods well known in the art. Conventional and well-known synthetic methods may be used in addition to the teachings herein. The synthesis of a typical compound described herein may be accomplished as described in the following examples. If available, reagents may be purchased commercially, e.g., from Sigma Aldrich or other chemical suppliers.

A compound described herein can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006), Greene's protective groups in organic synthesis. Hoboken, N.J., Wiley-Interscience, and references cited therein.

Furthermore, a compound described herein may contain one or more asymmetric ("chiral") centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromatography, chiral resolving agents, and the like. When enantiomerically pure or enriched compounds are desired, chiral chromatography and/or enantiomerically pure or enriched starting materials may be employed as conventionally used in the art or as described in the Examples.

The starting materials for the following reactions are generally known compounds or can be prepared by known procedures or obvious modifications thereof. For example, many of the starting materials are available from commercial suppliers such as Sigma Aldrich, Alfa Aesar, and the like. Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" and "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Generally, the term inert, as used herein with respect to a solvent, refers to a material that does not undergo reaction to form the target compound of interest through carbon-carbon bond forming reactions. Unless specified to the contrary, the solvents used in the reactions of the present disclosure are inert organic solvents, and the reactions are carried out under an inert gas, preferably nitrogen or argon.

The term "q.s." means adding a quantity sufficient to achieve a stated function, e.g., to bring a solution to the desired volume (i.e., 100%).

It will also be appreciated that in each of the below schemes, the addition of any substituent may result in the production of a number of isomeric products (including, but not limited to, enantiomers or one or more diastereomers) any or all of which may be isolated and purified using conventional techniques.

Incorporation of an isotopical label, e.g., a deuterium atom, into a compound described herein may be conducted by reacting an appropriate starting material(s) with a reagent including a radioactive isotope. Methods typically follow the same principles as standard organic chemical reactions, and may be carried out by any method known to those of skill in the art, including those provided in the present disclosure.

Scheme 1 provides exemplary synthetic routes for the synthesis of compounds provided herein (e.g., compounds of Formula I). The compounds of Formula I, or other formulas or compounds disclosed herein, are typically prepared by first providing Formulas Va and Vb and then attaching the desired substituents using suitable conditions (e.g., amide bond formation, nucleophilic aromatic substitution, or cross coupling).

In some embodiments, synthesis of a compound of Formula I proceeds according to Scheme 1. Synthesis of a compound of Formula I may proceed by coupling Compound Va with Compound Vb to form Compound Vc, coupling Compound Vc with Compound Vd, and preparing a compound of Formula I by one or more subsequent steps.

Scheme 1

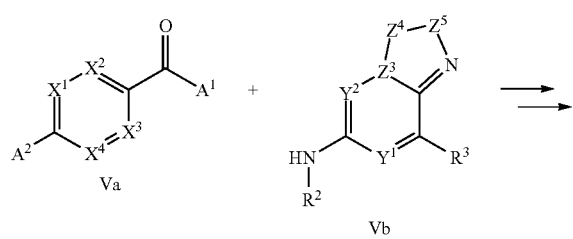

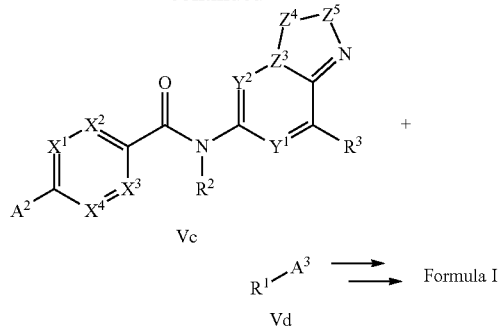

In Scheme 1, $R^1$, $R^2$, $R^3$, $X^1$, $X^2$, $X^3$, $X^4$, $Y^1$, and $Y^2$ are as defined herein. $A^1$, $A^2$, and $A^3$ are as defined below, and $Z^3$—$Z^4$—$Z^5$ is N—$CR^7$=$CR^8$ or C=$CR^7$—$NR^{10}$.

In Scheme 1, Compound Va may be joined with Compound Vb by amide bond formation through a leaving group at $A^1$ and an amine in Compound Vb (as shown in Scheme 1). $A^1$ may be a suitable leaving group such as, for example, a halide, a pseudohalide, a carboxylic acid, or carboylate. Compound Va may be activated at $A^1$ by an activating agent for activating a carboxylate group (e.g., chloro-N,N,N',N'-tetramethylformamidinium hexafluorophosphate, HATU, HBTU), optionally in the presence of a base (e.g., 1-methylimidazole, triethylamine, diisopropylethylamine), and in a suitable solvent (e.g., a polar aprotic solvent such as acetonitrile, DMF, or dichloromethane). Alternatively, a carboxylate at $A^1$ may be first activated by an activating agent (e.g., oxalyl chloride) and then combined with Compound Vb in the presence of a base (e.g., triethylamine, diisopropylethylamine). In such embodiments, an activated form of Compound Va (e.g., where $A^1$ is a halide such as a chloride) need not be isolated, and the reaction can be conducted in one pot.

In Scheme 1, a compound of Formula I may be prepared. Thus, Compound Vc may be joined with Compound Vd in a coupling reaction, e.g., by nucleophlic addition such as nucleophilic aromatic substitution to Compound Vc at $A^2$. In such embodiments, $A^2$ may be a suitable leaving group (e.g., a halide such as a chloride or a fluoride, or a pseudohalide such as a sulfonyl), and $A^3$ may be a hydrogen atom or, where $R^1$ is present as an anion, a cation (e.g., sodium ion, potassium ion). A nucleophilic aromatic substitution may be carried out heated (e.g., to a temperature of 50 to 200° C.) in the presence of a base (e.g., triethylamine, cesium carbonate, NaH, potassium carbonate, pyridine), and in a suitable solvent (e.g., dioxane, DMF, acetonitrile, DMSO). Alternatively, Compound Vc may be joined with Compound Vd in a coupling reaction (e.g., a metal-catalyzed coupling reaction). In such embodiments, for example, $A^2$ may be a leaving group (e.g., a halide such as a chloride or a bromide, or a pseudohalide such as a sulfonyl), and $R^1$ may comprise a suitable coupling functionality (e.g., a carbon-carbon double bond) and $A^3$ may be a complimentary coupling partner to $A^2$ (e.g., a hydrogen atom or a tin- or boron-containing group). The reaction may be conducted with a catalyst (e.g., bis(triphenylphosphine)palladium(II) dichloride), and optionally in the presence of a base (e.g., sodium carbonate).

In some embodiments, $A^2$ may be $R^1$, and Compound Vc may be converted to a compound of Formula I directly (without reaction with Compound Vd).

In Compound Va, Vb, Vc, and/or Vd, any of $R^1$, $R^2$, $R^3$, $X^1$, $X^2$, $X^3$, $X^4$, $Y^1$, $Y^2$, $Z^4$, and $Z^5$ may be present in a protected form, for example at an amine or hydroxyl group.

Amine protecting groups include those known in the art and described herein, including, for example, the tert-butoxycarbonyl group. In such embodiments, an additional step of deprotection may be needed. For example, where the protecting group is a tert-butoxycarbonyl group, an acidic deprotection step (e.g., using HCl in dioxane or TFA) may be needed to prepare the compound of Formula I.

A person of skill in the art will appreciate that any of Compound Va, Vb, Vc, or Vd may be available from a commercial supplier for a particular embodiment. Alternative synthesis of Compound Va, Vb, Vc, or Vd may be as described herein or as known to those of skill in the art.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Analytical Methods

Acidic QC methods
AcHSSC18—Standard Acidic UPLC-MS

| | |
|---|---|
| Instrumentation | UPLC + Waters DAD + Waters SQD2, single quadrapole UPLC-MS |
| MassLynx Files | |
| Column | Acquity UPLC HSS C18 1.8 um 100 × 2.1 mm. (Plus guard cartridge), maintained at temp |
| Mobile Phase A | Water (High purity via PureLab Option unit) with 0.1% formic acid |
| Mobile Phase B | Acetonitrile (Far UV grade) with 0.1% (V/V) formic acid |
| Flow | 0.4 mL/min |

| Gradient Program | Time (mins) | % A | % B |
|---|---|---|---|
| | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |

| | |
|---|---|
| Sample | 0.5-2 uL (concentration ~0.2-1 mg/mL). |
| Detectors | UV, diode array 210 nm-400 nm Resolution 1.2 nm Other wavelength traces are extracted from the DAD data MS, mass 100-700 (or ~1500 for HM method) in ES+ & ES– (300 μL/min split to MS) |

10 cm-Formic-AQ—Standard Acidic UPLC-MS

| | |
|---|---|
| Instrumentation | UPLC + Waters DAD + Waters SQD2, single quadrapole UPLC-MS |
| MassLynx Files | |
| Column | Acquity UPLC HSS C18 1.8 um 100 × 2.1 mm. (Plus guard cartridge), maintained at temp |
| Mobile Phase A | Water (High purity via PureLab Option unit) with 0.1% formic acid |
| Mobile Phase B | Acetonitrile (Far UV grade) with 0.1% (V/V) formic acid |
| Flow | 0.5 mL/min |

| Gradient Program | Time (mins) | % A | % B |
|---|---|---|---|
| | 0.0 | 95 | 05 |
| | 1.2 | 95 | 05 |
| | 3.5 | 0 | 100 |
| | 4.9 | 0 | 100 |
| | 5 | 95 | 05 |
| | 6 | 95 | 05 |

| | |
|---|---|
| Sample | 0.5-2 uL (concentration ~0.2-1 mg/mL). |
| Detectors | UV, diode array 210 nm-400 nm Resolution 1.2 nm Other wavelength traces are extracted from the DAD data MS, mass 100-700 (or ~1500 for HM method) in ES+ & ES– (300 μL/min split to MS) |

Acidic 1—Standard Acidic UPLC-MS

| | |
|---|---|
| Instrumentation | UPLC + Shimadzu SQD2, single quadrapole UPLC-MS |
| Column | Phenomenex C18 Kinetex column, 5 μm (4.6 × 150 mm) (Plus guard cartridge), maintained at temp |
| Mobile Phase A | Water with 0.1% v/v trifluoroacetic acid |
| Mobile Phase B | Acetonitrile with 0.1% v/v trifluoroacetic acid |
| Flow | 2.0 mL/min |

| Gradient Program | Time (mins) | % A | % B |
|---|---|---|---|
| | 0.0 | 95 | 5 |
| | 10.0 | 0 | 100 |
| | 13.0 | 0 | 100 |
| | 14.0 | 95 | 5 |

| | |
|---|---|
| Sample | 0.5-2 uL (concentration ~0.2-1 mg/mL). |
| Detectors | UV, 254 nm and 215 nm MS, mass 100-700 in ES+ & ES– (300 μL/min split to MS) |

Basic QC Methods
BicarbBEHC18—Standard Basic UPLC-MS

| | |
|---|---|
| Instrumentation | UPLC + Waters DAD + Waters SQD2, single quadrapole UPLC-MS |
| MassLynx Files | |
| Column | Acquity UPLC BEH Shield RP18 1.7 um 100 × 2.1 mm. (Plus guard cartridge), maintained at temp |
| Mobile Phase A | Water (High purity via PureLab Option unit) with 10 mM ammonium bicarbonate (ammonium hydrogen carbonate) |
| Mobile Phase B | Acetonitrile (Far UV grade) |
| Flow | 0.4 mL/min |

| Gradient Program | Time (mins) | % A | % B |
|---|---|---|---|
| | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |

| | |
|---|---|
| Sample | 0.5-2 uL (concentration ~0.2-1 mg/mL). |
| Detectors | UV, diode array 210 nm-400 nm Resolution 1.2 nm Other wavelength traces are extracted from the DAD data MS, mass 100-700 (or ~1500 for HM method) in ES+ & ES– (300 μL/min split to MS) |

10 cm_Bicarb_AQ—Standard Basic UPLC-MS

| Instrumentation | UPLC + Waters DAD + Waters SQD2, single quadrapole UPLC-MS |
|---|---|
| MassLynx Files | |
| Column | Acquity UPLC BEH Shield RP18 1.7 um 100 × 2.1 mm. (Plus guard cartridge), maintained at temp |
| Mobile Phase A | Water (High purity via PureLab Option unit) with 10 mM ammonium bicarbonate (ammonium hydrogen carbonate) |
| Mobile Phase B | Acetonitrile (Far UV grade) |
| Flow | 0.5 mL/min |

| Gradient Program | Time (mins) | % A | % B |
|---|---|---|---|
| | 0.0 | 95 | 05 |
| | 1.2 | 95 | 05 |
| | 3.5 | 0 | 100 |
| | 4.9 | 0 | 100 |
| | 5 | 95 | 05 |
| | 6 | 95 | 05 |

| Sample | 0.5-2 uL (concentration ~0.2-1 mg/mL). |
|---|---|
| Detectors | UV, diode array 210 nm-400 nm Resolution 1.2 nm Other wavelength traces are extracted from the DAD data MS, mass 100-700 (or –1500 for HM method) in ES+ & ES– (300 μL/min split to MS) |

General Procedures

Compounds were named with the Chemdraw 18.1 structure naming tool. All reactions involving air- or moisture-sensitive reagents were performed under a nitrogen atmosphere using dried solvents and glassware.

Example 1: (R)-5-(3-(cyclopropylamino)pyrrolidin-1-yl)-N-(2-methyl-6-(oxazol-5-ylmethoxy)-2H-indazol-5-yl)pyrazine-2-carboxamide

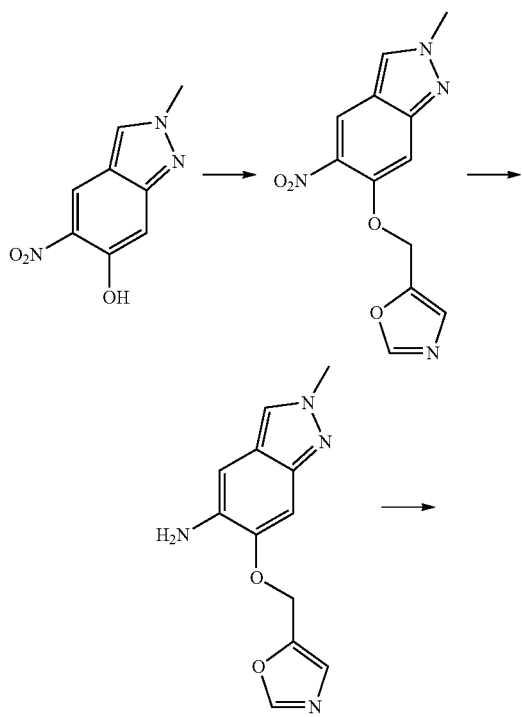

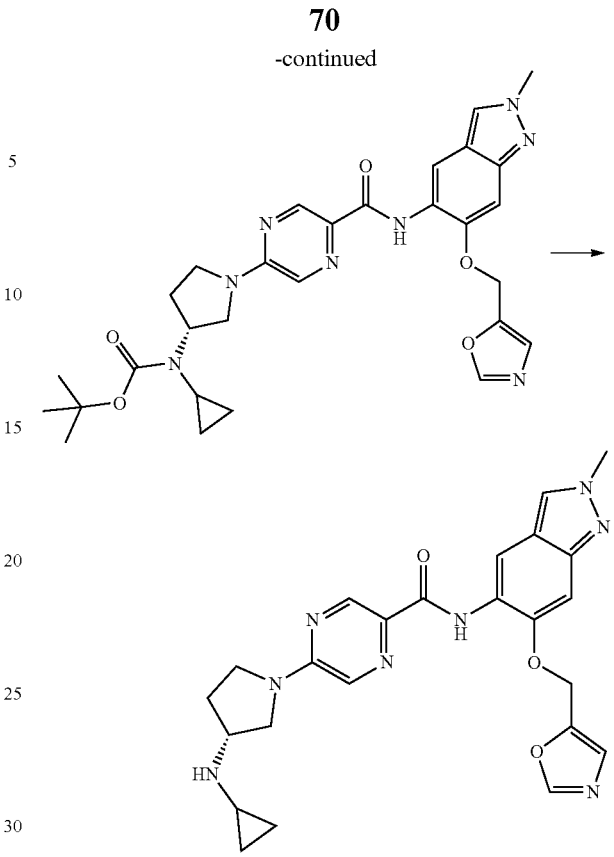

To a solution of 2-methyl-5-nitro-indazol-6-ol (500 mg, 2.59 mmol) in tetrahydrofuran (20 mL) was added triphenylphosphine (1018 mg, 3.88 mmol) and oxazol-4-yl-methanol (256 mg, 2.59 mmol). The mixture was cooled to 0° C. and diisopropyl azodicarboxylate (0.76 mL, 3.88 mmol) was added dropwise and reaction mixture stirred at RT for 18 h.

LCMS evidence indicated the reaction was ~60% complete. Further triphenylphosphine (339 mg, 1.29 mmol) was added followed by diisopropyl azodicarboxylate (0.25 mL, 1.29 mmol) at RT and the reaction stirred for a further 3 h at RT.

LCMS evidence indicated the reaction was complete. The reaction mixture was concentrated onto silica and purified by silica chromatography (40 g, eluting with EtOAc/cyclohexane 0-100%) to give 5-(((2-methyl-5-nitro-2H-indazol-6-yl)oxy)methyl)oxazole.

To a solution of 5-(((2-methyl-5-nitro-2H-indazol-6-yl)oxy)methyl)oxazole (300 mg, 1.09 mmol) in ethyl acetate (10 mL) and dichloromethane (10 mL) at RT was added tin(II) chloride dihydrate (987 mg, 4.38 mmol) and the reaction mixture was stirred for 18 h at RT.

LCMS indicated the mixture was mainly starting material. Large amounts of insoluble material were observed. MeOH (3 mL) was added to aid solubility. Further tin(II) chloride dihydrate (987 mg, 4.38 mmol) was added and the reaction mixture was stirred for 18 h at RT.

LCMS indicated the reaction was complete. The reaction was filtered through Celite and the Celite washed with DCM/MeOH (3:1). The solvent was removed in vacuo to give crude material, which was purified by silica chromatography (25 g, eluting with EtOAc/MeOH 0-10%) to give 2-methyl-6-(oxazol-5-ylmethoxy)-2H-indazol-5-amine, ~75% pure by LCMS, contaminated with $Ph_3PO$. The crude material was used in the next step without further purification.

2-Methyl-6-(oxazol-5-ylmethoxy)-2H-indazol-5-amine (50 mg, 0.205 mmol) and 5-[(3R)-3-[tert-butoxycarbonyl(cyclopropyl)amino]pyrrolidin-1-yl]pyrazine-2-carboxylic acid (76 mg, 0.218 mmol) was dissolved in acetonitrile (2 mL). 1-Methylimidazole (0.049 mL, 0.614 mmol) was added followed by chloro-N,N,N'N'-tetramethylformamidinium hexafluorophosphate (86 mg, 0.307 mmol). The reaction was stirred at RT for 18 h. The solid was collected by filtering to give tert-butyl (R)-cyclopropyl(1-(5-((2-methyl-6-(oxazol-5-ylmethoxy)-2H-indazol-5-yl)carbamoyl)pyrazin-2-yl)pyrrolidin-3-yl)carbamate.

tert-Butyl (R)-cyclopropyl(1-(5-((2-methyl-6-(oxazol-5-ylmethoxy)-2H-indazol-5-yl)carbamoyl)pyrazin-2-yl)pyrrolidin-3-yl)carbamate (32 mg, 0.0557 mmol) was dissolved in dichloromethane (3 mL) and trifluoroacetic acid (1.0 mL, 13.1 mmol) was added at RT. The reaction was stirred at RT for 1 h. The solvent was removed in vacuo and the residue oil dried in a vac oven overnight. The residue was free based by passing through an SCX column (1 g, eluting with MeOH and then 10% 7M NH$_3$ in MeOH/MeOH). The ammoniacal fractions were combined and the solvent removed in vacuo to give the title compound. LCMS (ES+) 475.2 (M+H)+, RT 2.48 min (Analytical method AcHSSC18); $^1$H NMR (400 MHz, DMSO-d$_6$) d 10.06 (s, 1H), 8.73 (d, J=1.3 Hz, 1H), 8.66 (s, 1H), 8.46 (s, 1H), 8.31 (s, 1H), 8.22 (s, 1H), 7.94 (d, J=1.3 Hz, 1H), 7.31 (s, 1H), 5.25 (s, 2H), 4.09 (s, 3H), 3.73-3.60 (m, 2H), 3.59-3.48 (m, 2H), 3.44-3.39 (m, 1H), 2.18-2.11 (m, 2H), 1.98-1.90 (m, 1H), 0.42 (m, 2H), 0.29-0.23 (m, 2H).

Example 2: (R)-5-(3-(cyclopropylamino)pyrrolidin-1-yl)-N-(2-methyl-6-((tetrahydro-2H-pyran-4-yl)oxy)-2H-indazol-5-yl)pyrazine-2-carboxamide

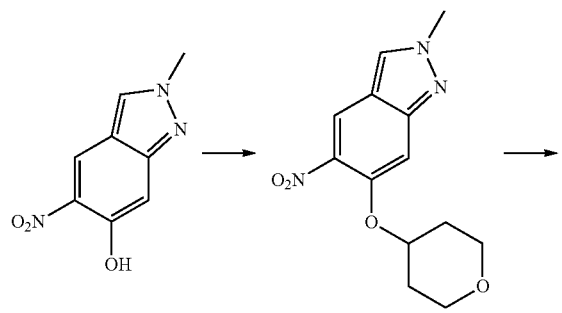

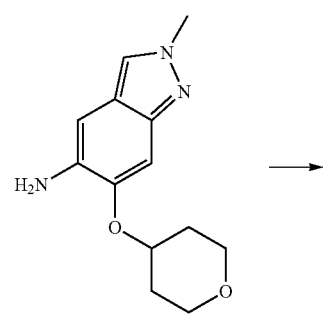

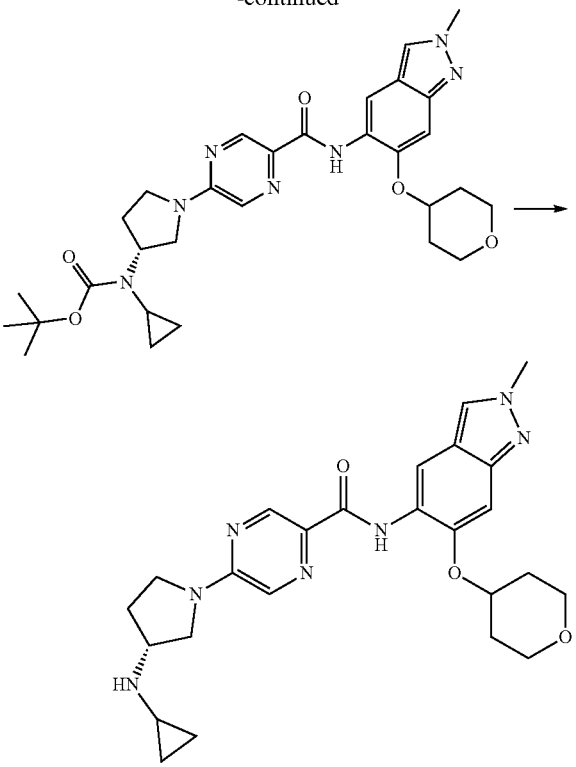

To a solution of 2-methyl-5-nitro-indazol-6-ol (300 mg, 1.55 mmol) in tetrahydrofuran (20 mL) was added triphenylphosphine (611 mg, 2.33 mmol) and tetrahydro-4-pyranol (0.15 mL, 1.55 mmol) and the resulting mixture was stirred at 0° C. Diisopropyl azodicarboxylate (0.46 mL, 2.33 mmol) was added dropwise and reaction mixture stirred at RT for 18 h. The solvent was removed in vacuo and the residue was purified by silica chromatography (25 g, eluting with EtOAc/cyclohexane 0-100%) to give 2-methyl-5-nitro-6-((tetrahydro-2H-pyran-4-yl)oxy)-2H-indazole.

2-Methyl-5-nitro-6-tetrahydropyran-4-yloxy-indazole (192 mg, 0.692 mmol) and tin(II) chloride dihydrate (625 mg, 2.77 mmol) was suspended in ethyl acetate (10 mL), dichloromethane (10 mL) and acetic acid (1 mL). The mixture was stirred for 48 h at RT. The solvent was removed in vacuo to give a residue, which was dissolved in MeOH and loaded onto an SCX column (10 g, eluting with MeOH and then 10% 7M NH3 in MeOH/MeOH). The ammoniacal fractions were combined and the solvent removed in vacuo to give 2-methyl-6-((tetrahydro-2H-pyran-4-yl)oxy)-2H-indazol-5-amine.

2-Methyl-6-tetrahydropyran-4-yloxy-indazol-5-amine (100 mg, 0.404 mmol) was dissolved in acetonitrile (5 mL) and 5-[(3R)-3-[tert-butoxycarbonyl(cyclopropyl)amino]pyrrolidin-1-yl]pyrazine-2-carboxylic acid (150 mg, 0.431 mmol) and 1-methylimidazole (0.097 mL, 1.21 mmol) was added. Chloro-N,N,N',N'-tetramethylformamidinium hexafluorophosphate (170 mg, 0.607 mmol, 1.50 eq) was added and the reaction stirred at RT for 18 h. The solvent was removed in vacuo and the residue purified by prep HPLC to give tert-butyl (R)-cyclopropyl(1-(5-((2-methyl-6-((tetrahydro-2H-pyran-4-yl)oxy)-2H-indazol-5-yl)carbamoyl)pyrazin-2-yl)pyrrolidin-3-yl)carbamate.

tert-Butyl (R)-cyclopropyl(1-(5-((2-methyl-6-((tetrahydro-2H-pyran-4-yl)oxy)-2H-indazol-5-yl)carbamoyl)

pyrazin-2-yl)pyrrolidin-3-yl)carbamate (63 mg, 0.109 mmol) was dissolved in dichloromethane (3 mL) and trifluoroacetic acid (1.0 mL, 13.1 mmol) was added at RT. The reaction was stirred at RT for 1 h. The solvent was removed in vacuo to give a residue oil, which was dried in a vacuum oven overnight. The residue was free based by passing through an SCX column (1 g, eluting with MeOH and then 10% 7M $NH_3$ in MeOH/MeOH). The ammoniacal fractions were combined and the solvent removed in vacuo to give the title compound. LCMS (ES+) 478.2 (M+H)+, RT 2.67 min (Analytical method AcHSSC18); $^1$H NMR (400 MHz, DMSO-$d_6$) d 10.26 (s, 1H), 8.74 (d, J=1.3 Hz, 1H), 8.66 (s, 1H), 8.21 (s, 1H), 7.99 (d, J=1.5 Hz, 1H), 7.21 (s, 1H), 4.90-4.83 (m, 1H), 4.08 (s, 3H), 3.96-3.88 (m, 2H), 3.71-3.49 (m, 6H), 3.44-3.41 (m, 1H), 2.13-2.04 (m, 4H), 1.96-1.90 (m, 1H), 1.75 (m, 2H), 0.41 (m, 2H), 0.27-0.21 (m, 2H) NH not observed.

Example 3: (R)-N-(6-(but-2-yn-1-yloxy)-2-methyl-2H-indazol-5-yl)-5-(3-(cyclopropylamino)pyrrolidin-1-yl)pyrazine-2-carboxamide

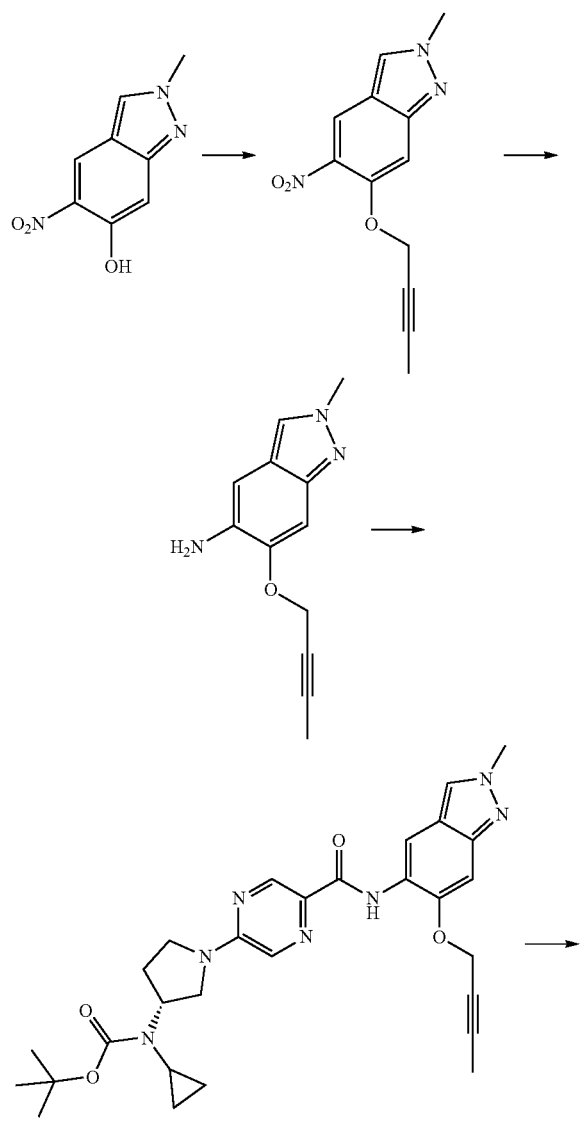

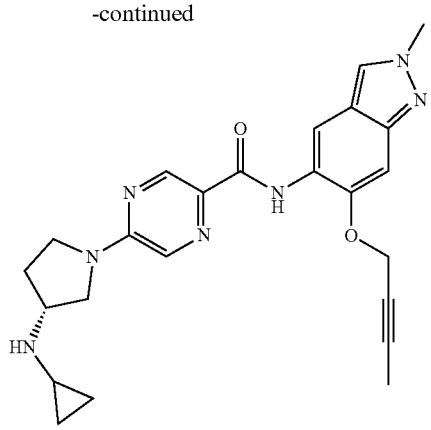

2-Methyl-5-nitro-indazol-6-ol (200 mg, 1.04 mmol) was dissolved in tetrahydrofuran (20 mL) and triphenylphosphine (543 mg, 2.07 mmol) and 2-Butyn-1-ol (0.085 mL, 1.14 mmol) was added. The mixture was cooled to 0° C. and diisopropyl azodicarboxylate (0.41 mL, 2.07 mmol) was added dropwise. The reaction mixture was stirred at RT for 18 h. The solvent was removed in vacuo and the residue was purified by silica chromatography (25 g, eluting with EtOAc/cyclohexane 0-100%) to give 6-(but-2-yn-1-yloxy)-2-methyl-5-nitro-2H-indazole. The material was 60% pure by LCMS with triphenylphospine oxide impurity. Used in the next step without further purification.

6-(But-2-yn-1-yloxy)-2-methyl-5-nitro-2H-indazole (490 mg, 1.20 mmol) was dissolved in ethyl acetate (10 mL) and dichloromethane (10 mL) and tin(II) chloride dihydrate (1082 mg, 4.80 mmol) was added at RT. The reaction was stirred for 48 h at RT. The solvent was removed in vacuo to give a residue, which was dissolved in MeOH and loaded onto an SCX column (10 g, eluting with MeOH and then 10% 7M $NH_3$ in MeOH/MeOH). The ammoniacal fractions were combined and the solvent removed in vacuo to give 6-(but-2-yn-1-yloxy)-2-methyl-2H-indazol-5-amine.

6-(But-2-yn-1-yloxy)-2-methyl-2H-indazol-5-amine (168 mg, 0.780 mmol) was dissolved in acetonitrile (5 mL) and 5-[(3R)-3-[tert-butoxycarbonyl(cyclopropyl)amino]pyrrolidin-1-yl]pyrazine-2-carboxylic acid (272 mg, 0.780 mmol) and 1-methylimidazole (0.19 mL, 2.34 mmol) was added. Chloro-N,N,N',N'-tetramethylformamidinium hexafluorophosphate (328 mg, 1.17 mmol) was added and the reaction stirred at RT for 18 h. The solvent was removed in vacuo to give a residue, which was purified by preparative HPLC to give tert-butyl (R)-(1-(5-((6-(but-2-yn-1-yloxy)-2-methyl-2H-indazol-5-yl)carbamoyl)pyrazin-2-yl)pyrrolidin-3-yl)(cyclopropyl)carbamate.

tert-Butyl (R)-(1-(5-((6-(but-2-yn-1-yloxy)-2H-indazol-5-yl)carbamoyl)pyrazin-2-yl)pyrrolidin-3-yl)(cyclopropyl)carbamate (97 mg, 0.179 mmol) was dissolved in dichloromethane (3 mL) and trifluoroacetic acid (1 mL) was added at RT. The reaction was stirred at RT for 1 h. The solvent was removed in vacuo to give a residue oil, which was dried in a vacuum oven overnight. The residue was free based by passing through an SCX column (1 g, eluting with MeOH and then 10% 7M $NH_3$ in MeOH/MeOH). The ammoniacal fractions were combined and the solvent removed in vacuo to give the title compound. LCMS (ES+) 446.2 (M+H)+, RT 4.09 min (Analytical method BicarbBEHC18); $^1$H NMR (400 MHz, DMSO-$d_6$) d 9.99 (s, 1H), 8.74 (d, J=1.3 Hz, 1H), 8.68 (s, 1H), 8.22 (s, 1H), 8.01 (d, J=1.5 Hz, 1H), 7.18 (s, 1H), 5.00-4.97 (m, 2H), 4.09 (s, 3H), 3.72-3.50 (m, 4H), 3.45-3.40 (m, 1H), 2.15-2.10 (m, 2H), 1.98-1.89 (m, 1H), 1.87-1.85 (m, 3H), 0.43-0.39 (m, 2H), 0.28-0.22 (m, 2H) NH not observed.

Example 4: (R)-N-(2-methyl-6-(prop-2-yn-1-yloxy)-2H-indazol-5-yl)-5-(3-(methylamino)pyrrolidin-1-yl)pyrazine-2-carboxamide

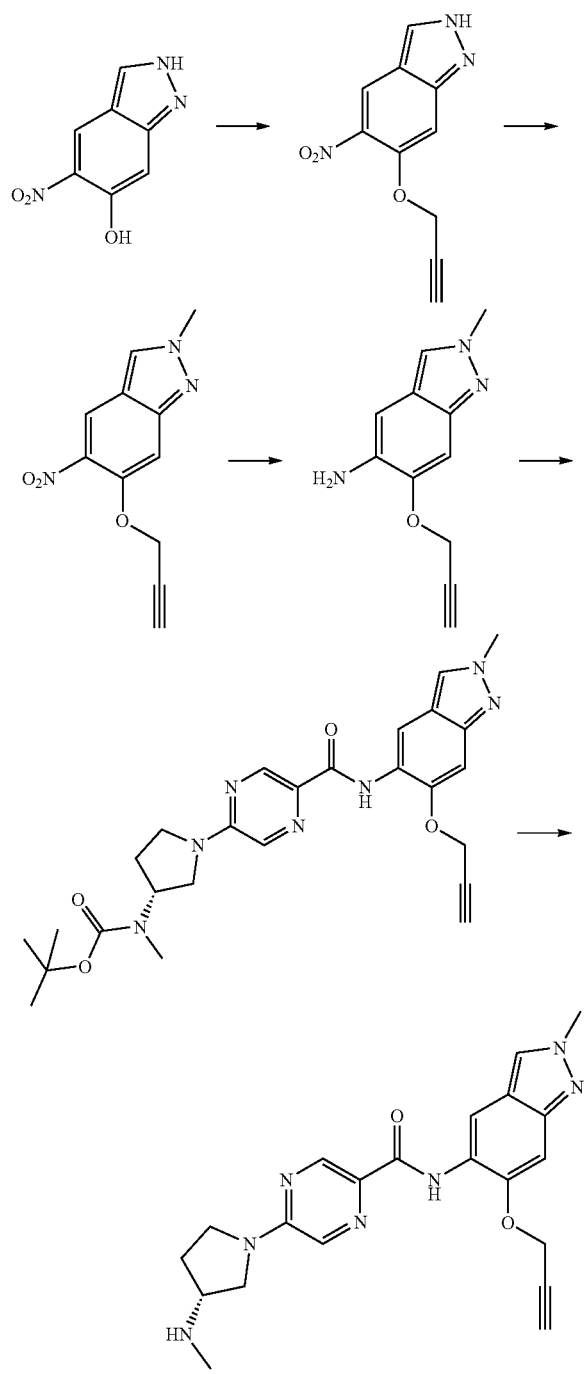

5-Nitro-2H-indazol-6-ol (500 mg, 2.79 mmol, 1.00 eq), triphenylphosphine (1098 mg, 4.19 mmol, 1.50 eq), propargyl alcohol (0.16 mL, 2.79 mmol, 1.00 eq) in tetrahydrofuran (20 mL) was stirred at 0° C. Diisopropyl azodicarboxylate (0.82 mL, 4.19 mmol, 1.50 eq) was added dropwise and the reaction mixture stirred at room temperature overnight. Water was added and the product extracted into ethyl acetate. The organic phase was dried over a hydrophobic frit and concentrated under reduced pressure. The residue was purified by silica gel chromatography using 0-100% ethyl acetate in cyclohexane. The appropriate fractions were combined and concentrated under reduced pressure to yield 5-nitro-6-prop-2-ynoxy-1H-indazole. LCMS: ES+218.3. $^1$H NMR (400 MHz, DMSO-$d_6$) 13.49 (1H, s), 8.51 (1H, s), 8.27 (1H, s), 7.39 (1H, s), 5.11 (2H, d, J=2.4 Hz), 3.76 (1H, t, J=2.4 Hz).

5-Nitro-6-prop-2-ynoxy-1H-indazole (480 mg, 2.21 mmol, 1.00 eq) in ethyl acetate (10.00 mL) was stirred at 0° C. Trimethyloxonium tetrafluoroborate (327 mg, 2.21 mmol, 1.00 eq) was added portionwise and the reaction mixture allowed to warm to room temperature with stirring overnight. Water was added and the organic phase separated. The organic phase was dried over a hydrophobic frit and concentrated under reduced pressure. The residue was purified by silica gel chromatography using 0-100% ethyl acetate in cyclohexane. The appropriate fractions were combined and concentrated under reduced pressure to yield 2-methyl-5-nitro-6-prop-2-ynoxy-indazole, which was used crude in the next step.

2-Methyl-5-nitro-6-prop-2-ynoxy-indazole (460 mg, 1.99 mmol, 1.00 eq), tin(II) chloride dihydrate (1796 mg, 7.96 mmol, 4.00 eq) in ethyl acetate (10 mL) and dichloromethane (10 mL) was stirred overnight at room temperature. The reaction mixture was filtered through celite and concentrated under reduced pressure to yield 2-methyl-6-prop-2-ynoxy-indazol-5-amine. LCMS: ES+202.2. $^1$H NMR (400 MHz, DMSO-$d_6$) 7.86 (1H, s), 6.98 (1H, s), 6.71 (1H, s), 4.90 (2H, d, J=2.7 Hz), 4.63 (2H, s), 4.05 (3H, s), 3.65 (1H, t, J=2.7 Hz).

2-Methyl-6-prop-2-ynoxy-indazol-5-amine (50 mg, 0.248 mmol, 1.00 eq), 5-[(3R)-3-[tert-butoxycarbonyl(methyl)amino]pyrrolidin-1-yl]pyrazine-2-carboxylic acid (80 mg, 0.248 mmol, 1.00 eq), chloro-N,N,N',N'-tetramethylformamidinium hexafluorophosphate (105 mg, 0.373 mmol, 1.50 eq), 1-methylimidazole (0.059 mL, 0.745 mmol, 3.00 eq) in acetonitrile (2 mL) stirred at room temperature overnight. Ethyl acetate and water were added, and the organic phase was separated, dried over a hydrophobic frit, and concentrated under reduced pressure to yield tert-butyl N-methyl-N-[(3R)-1-[5-[(2-methyl-6-prop-2-ynoxy-indazol-5-yl)carbamoyl]pyrazin-2-yl]pyrrolidin-3-yl]carbamate. LCMS: ES+506.5.

tert-Butyl N-methyl-N-[(3R)-1-[5-[(2-methyl-6-prop-2-ynoxy-indazol-5-yl)carbamoyl]pyrazin-2-yl]pyrrolidin-3-yl]carbamate (80 mg, 0.158 mmol, 1.00 eq), trifluoroacetic acid (0.12 mL, 1.58 mmol, 10.0 eq) combined in dichloromethane (2 mL) and stirred at room temperature for 2 hours. The reaction mixture was concentrated under reduced pressure and purified by prep-HPLC. This yielded (R)-N-(2-methyl-6-(prop-2-yn-1-yloxy)-2H-indazol-5-yl)-5-(3-(methylamino)pyrrolidin-1-yl)pyrazine-2-carboxamide. LCMS (ES+) 406.2 (M+H)+, RT 2.74 min (Analytical method AcHSSC18). $^1$H NMR (400 MHz, DMSO-$d_6$) 10.02 (1H, s), 8.76 (1H, d, J=1.4 Hz), 8.71 (1H, s), 8.26 (1H, s), 8.04 (1H, d, J=1.4 Hz), 7.23 (1H, s), 5.08-5.03 (2H, m), 4.12-4.10 (3H, m), 3.71-3.56 (5H, m), 3.48-3.40 (2H, m), 2.35 (3H, s), 2.19-2.10 (1H, m), 1.93 (1H, d, J=5.6 Hz).

Example 5: (R)-5-(3-(cyclopropylamino)pyrrolidin-1-yl)-N-(2-methyl-6-(prop-2-yn-1-yloxy)-2H-indazol-5-yl)pyrazine-2-carboxamide

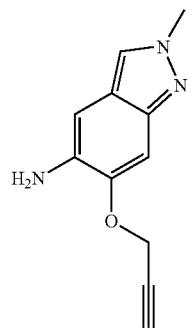

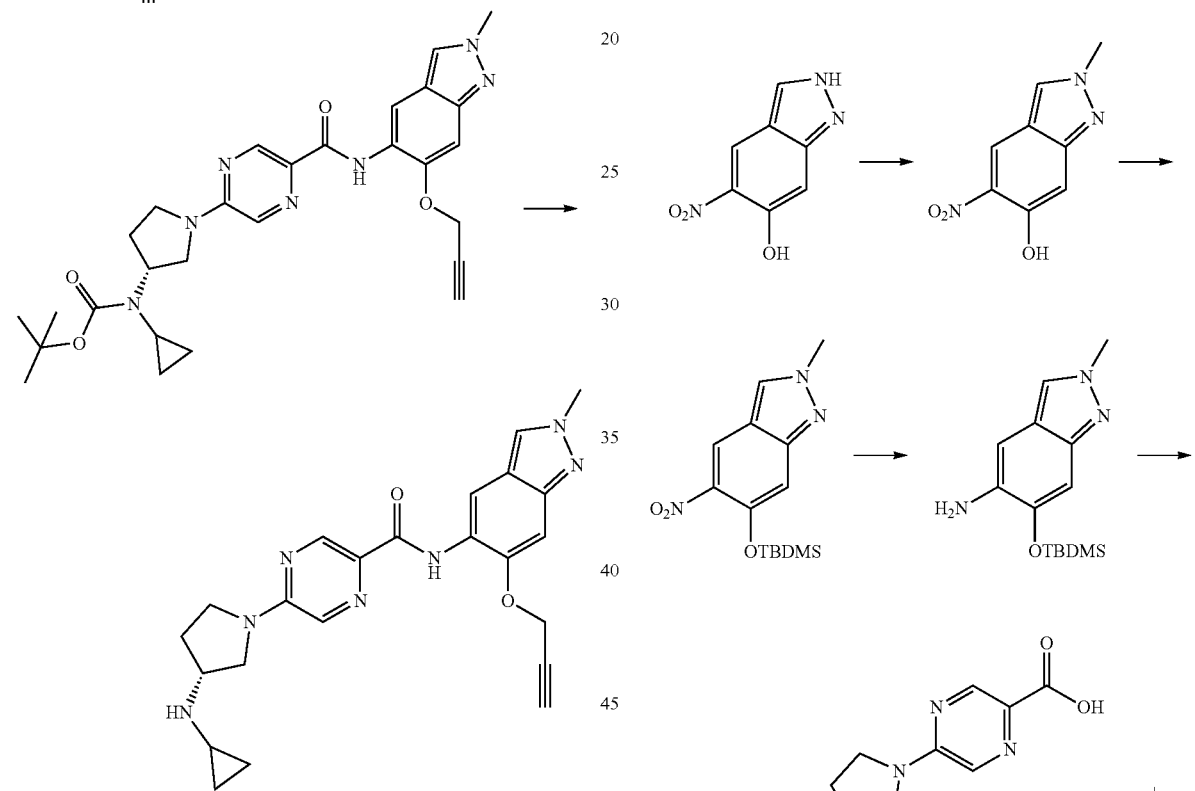

2-Methyl-6-prop-2-ynoxy-indazol-5-amine (50 mg, 0.248 mmol, 1.00 eq) and 5-[(3R)-3-[tert-butoxycarbonyl(cyclopropyl)amino]pyrrolidin-1-yl]pyrazine-2-carboxylic acid (75 mg, 0.215 mmol, 0.866 eq) were dissolved in acetonitrile (2 mL) at room temperature. Chloro-N,N,N',N'-tetramethylformamidinium hexafluorophosphate (108 mg, 0.385 mmol, 1.55 eq) and 1-methylimidazole (0.060 mL, 0.753 mmol, 3.03 eq) were added and the reaction mixture stirred for 24 h. The resulting precipitate was collected by filtration to yield tert-butyl N-cyclopropyl-N-[(3R)-1-[5-[(2-methyl-6-prop-2-ynoxy-indazol-5-yl)carbamoyl]pyrazin-2-yl]pyrrolidin-3-yl]carbamate. LCMS (ES+) 532 (M+H)+.

tert-Butyl N-cyclopropyl-N-[(3R)-1-[5-[(2-methyl-6-prop-2-ynoxy-indazol-5-yl)carbamoyl]pyrazin-2-yl]pyrrolidin-3-yl]carbamate (132 mg, 0.249 mmol, 1.00 eq) was suspended in dichloromethane (5 mL). Trifluoroacetic acid (1.5 mL, 19.6 mmol, 78.8 eq) was added and the mixture stirred at room temperature for 80 minutes. The reaction mixture was quenched with methanol and concentrated under reduced pressure. The residue was purified by prep-HPLC followed by achiral SFC to yield the title compound. LCMS (ES+) 432.2 (M+H)+, RT 2.66 min (Analytical method AcHSSC18) $^1$H NMR (400 MHz, DMSO-$d_6$) d 10.03 (s, 1H), 8.73 (s, 1H), 8.28 (s, 1H), 8.05 (d, J=1.3 Hz, 1H), 7.25 (s, 1H), 5.08 (d, J=2.4 Hz, 2H), 4.13 (s, 3H), 3.76-3.51 (m, 6H), 3.44-3.38 (m, 1H), 2.16-2.06 (m, 2H), 1.94 (s, 1H), 0.43-0.39 (m, 2H), 0.28-0.19 (m, 2H).

Example 6: (R)-5-(3-(cyclopropylamino)pyrrolidin-1-yl)-N-(2-methyl-6-((tetrahydro-2H-pyran-4-yl)methoxy)-2H-indazol-5-yl)pyrazine-2-carboxamide

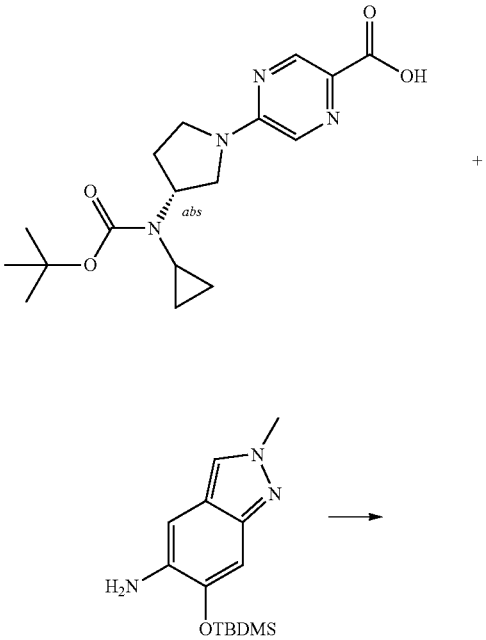

-continued

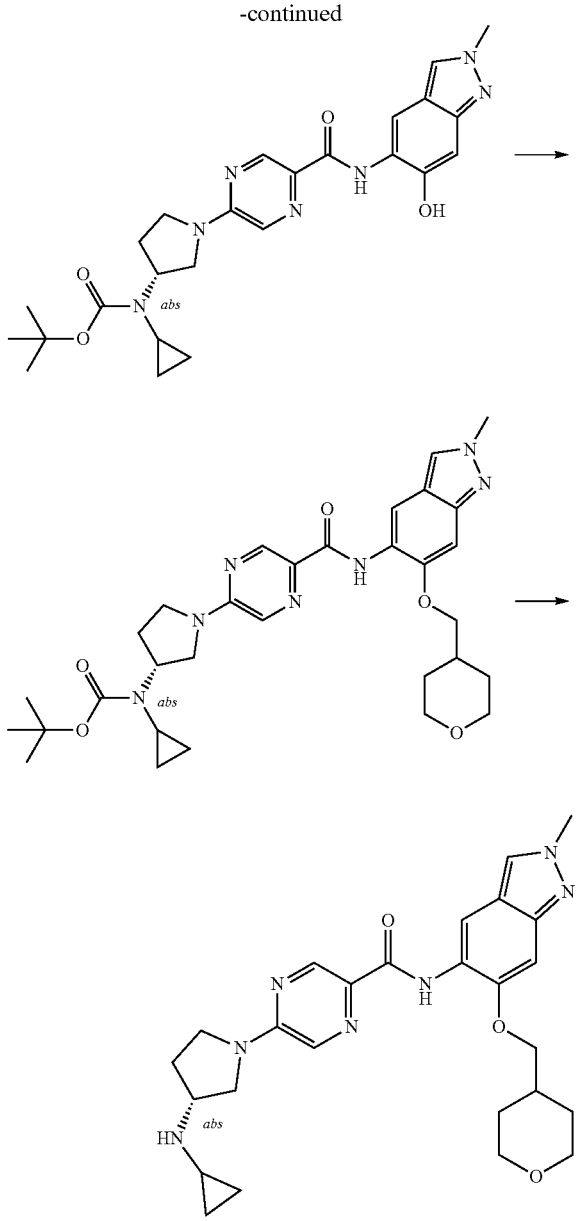

5-Nitro-1H-indazol-6-ol (2.00 g, 11.2 mmol, 1 eq), trimethyloxonium tetrafluoroborate (1.98 g, 13.4 mmol, 1.20 eq) and ethyl acetate (100 mL) were combined and stirred at RT for 4 days. The mixture was then diluted with EtOAC, washed with water, dried over magnesium sulfate and concentrated in vacuo to give 2-methyl-5-nitro-indazol-6-ol. $^1$H NMR (400 MHz, DMSO-d$_6$) 10.45 (1H, s), 8.54 (1H, s), 8.46 (1H, s), 7.02 (1H, s), 4.15 (3H, s).

2-Methyl-5-nitro-indazol-6-ol (405 mg, 2.10 mmol, 1 eq), tert-butyldimethylsilyl chloride (348 mg, 2.31 mmol, 1.1 eq), sodium hydride (60%, 92 mg, 2.31 mmol, 1.1 eq) and tetrahydrofuran (10 mL) were combined and stirred at RT under a nitrogen atmosphere for 90 min. The mixture was then concentrated in vacuo onto silica and purified by flash chromatography to give tert-butyl-dimethyl-(2-methyl-5-nitro-indazol-6-yl)oxy-silane. $^1$H NMR (400 MHz, CDCl$_3$) 8.17 (1H, s), 8.01 (1H, s), 7.11 (1H, s), 4.21 (3H, s), 1.01 (9H, s), 0.29 (6H, s).

tert-Butyl-dimethyl-(2-methyl-5-nitro-indazol-6-yl)oxy-silane (510 mg, 1.66 mmol, 1 eq), ethyl acetate (50 mL) and 10% palladium on carbon were combined and stirred under a hydrogen atmosphere for 20 h. The catalyst was then filtered off through a celite plug and the mixture concentrated in vacuo to give 6-[tert-butyl(dimethyl)silyl]oxy-2-methyl-indazol-5-amine. $^1$H NMR (400 MHz, CDCl$_3$) 7.55 (1H, s), 6.98 (1H, s), 6.76 (1H, s), 4.09 (3H, s), 3.83-3.74 (2H, m), 1.04 (9H, s), 0.31 (6H, s).

6-[tert-Butyl(dimethyl)silyl]oxy-2-methyl-indazol-5-amine (200 mg, 0.721 mmol, 1 eq), 5-[(3R)-3-[tert-butoxycarbonyl(cyclopropyl)amino]pyrrolidin-1-yl]pyrazine-2-carboxylic acid (251 mg, 0.721 mmol, 1 eq), HBTU (273 mg, 0.721 mmol, 1 eq), N,N-dimethylformamide (4 mL) and triethylamine (0.50 mL, 3.59 mmol, 4.98 eq) were combined and stirred at RT for 90 min. The mixture was then concentrated in vacuo onto silica and purified by flash chromatography eluting with 0-100% EtOAc in cyclohexane then 10% MeOH in EtOAc to give tert-butyl N-cyclopropyl-N-[(3R)-1-[5-[(6-hydroxy-2-methyl-indazol-5-yl)carbamoyl]pyrazin-2-yl]pyrrolidin-3-yl]carbamate. $^1$H NMR (400 MHz, DMSO-d$_6$) 10.49 (1H, s), 10.13 (1H, s), 8.77 (1H, d, J=1.3 Hz), 8.64 (1H, s), 8.17 (1H, s), 8.09 (1H, s), 6.94 (1H, s), 4.40 (1H, dd, J=7.8, 7.8 Hz), 4.06 (3H, s), 3.87-3.80 (2H, m), 3.62 (1H, dd, J=8.3, 10.8 Hz), 3.54-3.46 (1H, m), 2.46-2.40 (2H, m), 2.29-2.23 (1H, m), 1.43 (9H, s), 0.79-0.74 (2H, m), 0.67-0.63 (2H, m).

tert-Butyl N-cyclopropyl-N-[(3R)-1-[5-[(6-hydroxy-2-methyl-indazol-5-yl)carbamoyl]pyrazin-2-yl]pyrrolidin-3-yl]carbamate (120 mg, 0.243 mmol, 1 eq), potassium carbonate (40 mg, 0.292 mmol, 1.20 eq), acetone (20 mL) and 4-(bromomethyl)tetrahydropyran (44 mg, 0.243 mmol, 1 eq) were combined and hot block heated to 50° C. for 3 days. Then potassium tert-butoxide (27 mg, 0.243 mmol, 1 eq) was added and the mixture was stirred at 50° C. for additional 24 h. The mixture was then cooled to room temperature, the potassium salts were filtered off through a celite plug and the solution concentrated in vacuo. The residue was purified by prep HPLC to give partially purified tert-butyl (R)-cyclopropyl(1-(5-((2-methyl-6-((tetrahydro-2H-pyran-4-yl)methoxy)-2H-indazol-5-yl)carbamoyl)pyrazin-2-yl)pyrrolidin-3-yl)carbamate, which was used in the following step without further purification.

tert-Butyl N-cyclopropyl-N-[(3R)-1-[5-[[2-methyl-6-(tetrahydropyran-4-ylmethoxy)indazol-5-yl]carbamoyl]pyrazin-2-yl]pyrrolidin-3-yl]carbamate (27 mg, 0.0448 mmol, 1.00 eq), methyl alcohol (2 mL) and 4 M hydrogen chloride in dioxane (2.0 mL, 8.00 mmol, 179 eq) were combined and stirred at room temperature for one hour. The mixture was then concentrated in vacuo and purified by prep HPLC to give (R)-5-(3-(cyclopropylamino)pyrrolidin-1-yl)-N-(2-methyl-6-((tetrahydro-2H-pyran-4-yl)methoxy)-2H-indazol-5-yl)pyrazine-2-carboxamide as a formate salt. LCMS (ES+) 492.2 (M+H)+, RT 2.82 min (Analytical method AcHSSC18) $^1$H NMR (400 MHz, DMSO-d$_6$) 10.29 (1H, s), 8.73 (1H, d, J=1.1 Hz), 8.60 (1H, s), 8.22 (1H, s), 8.20 (1H, s), 7.88 (1H, d, J=1.4 Hz), 7.08 (1H, s), 4.08 (3H, s), 4.06-3.95 (5H, m), 3.70-3.53 (6H, m), 2.16-2.09 (3H, m), 1.97-1.94 (1H, m), 1.82-1.78 (2H, m), 1.58-1.49 (2H, m), 0.42-0.39 (2H, m), 0.27-0.21 (2H, m).

Example 7: (R)-N-(6-(cyanomethoxy)-2-methyl-2H-indazol-5-yl)-5-(3-(cyclopropylamino)pyrrolidin-1-yl)pyrazine-2-carboxamide

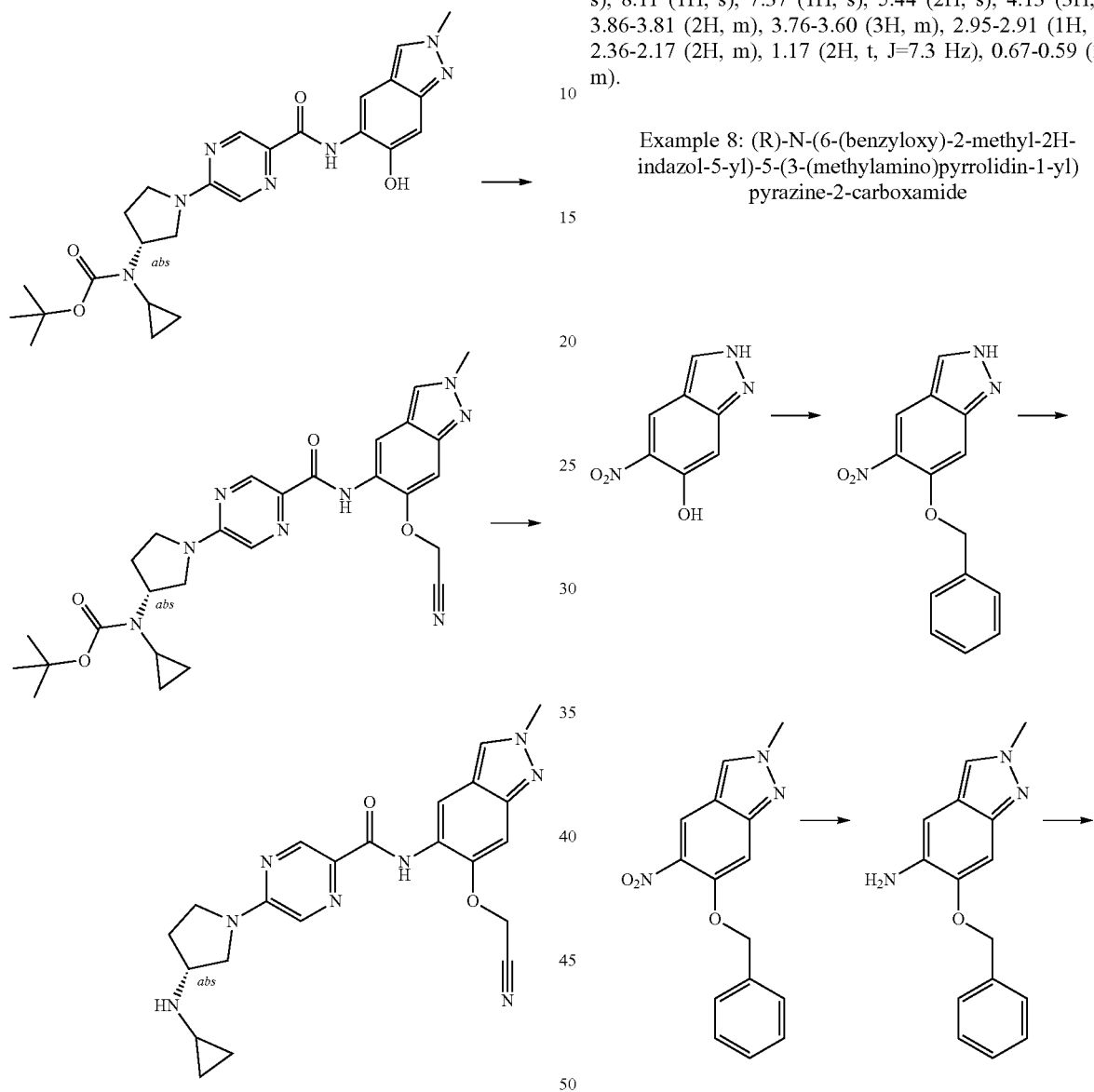

tert-Butyl N-cyclopropyl-N-[(3R)-1-[5-[(6-hydroxy-2-methyl-indazol-5-yl)carbamoyl]pyrazin-2-yl]pyrrolidin-3-yl]carbamate (100 mg, 0.203 mmol, 1 eq, synthesis described in example 6), potassium carbonate (34 mg, 0.243 mmol, 1.20 eq), acetone (10 mL) and bromoacetonitrile (0.014 mL, 0.203 mmol, 1.00 eq) were combined in a sealed tube and hot block heated to 50° C. The reaction mixture was cooled to RT. Potassium salts were filtered off and the filtrate was concentrated in vacuo. The residue was purified by prep HPLC and the intermediate was used as such in the next step.

tert-Butyl N-[(3R)-1-[5-[[6-(cyanomethoxy)-2-methyl-indazol-5-yl]carbamoyl]pyrazin-2-yl]pyrrolidin-3-yl]-N-cyclopropyl-carbamate (23 mg, 0.0430 mmol, 1 eq), dichloromethane (2 mL) and trifluoroacetic acid (1 mL, 13.1 mmol, 304 eq) were combined and stirred at RT. The reaction mixture was concentrated in vacuo. The residue was purified by prep HPLC, followed by achiral SFC purification. LCMS (ES+) 433.2 (M+H)+, RT 3.66 min (Analytical method BicarbBEHC18). $^1$H NMR (400 MHz, DMSO-$d_6$) 9.96 (1H, s), 8.80 (1H, d, J=1.3 Hz), 8.71 (1H, s), 8.31 (1H, s), 8.11 (1H, s), 7.37 (1H, s), 5.44 (2H, s), 4.13 (3H, s), 3.86-3.81 (2H, m), 3.76-3.60 (3H, m), 2.95-2.91 (1H, m), 2.36-2.17 (2H, m), 1.17 (2H, t, J=7.3 Hz), 0.67-0.59 (3H, m).

Example 8: (R)-N-(6-(benzyloxy)-2-methyl-2H-indazol-5-yl)-5-(3-(methylamino)pyrrolidin-1-yl)pyrazine-2-carboxamide

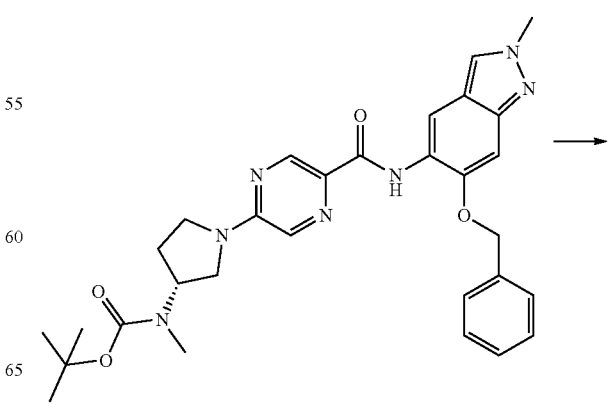

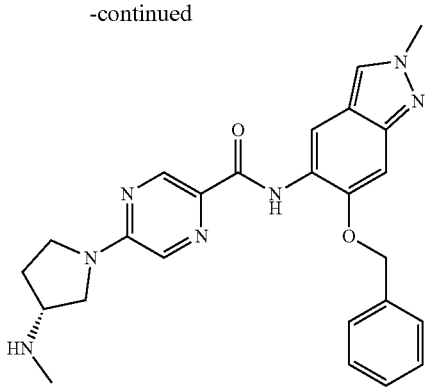

5-Nitro-2H-indazol-6-ol (500 mg, 2.79 mmol, 1.00 eq), triphenylphosphine (1098 mg, 4.19 mmol, 1.50 eq), and benzyl alcohol (0.29 mL, 2.79 mmol, 1.00 eq) in tetrahydrofuran (20 mL) were stirred at 0° C. Diisopropyl azodicarboxylate (0.82 mL, 4.19 mmol, 1.50 eq) was added dropwise and reaction mixture warmed to room temperature overnight. Water was added and the product was extracted into ethyl acetate. The organic phase was dried over a hydrophobic frit and concentrated under reduced pressure. The residue was purified by silica gel chromatography using 0-100% ethyl acetate in cyclohexane. The appropriate fractions were combined and concentrated under reduced pressure to yield 6-benzyloxy-5-nitro-1H-indazole. LCMS: ES+268.1. $^1$H NMR (400 MHz, CDCl$_3$) 10.04 (1H, s), 8.33 (1H, s), 8.12 (OH, s), 7.52-7.34 (5H, m), 7.05 (1H, s), 5.28 (2H, s).

6-Benzyloxy-5-nitro-1H-indazole (371 mg, 1.42 mmol, 1.00 eq) in ethyl acetate (10 mL) was stirred at 0° C. Trimethyloxonium tetrafluoroborate (209 mg, 1.42 mmol, 1.00 eq) was added portionwise and the reaction mixture was allowed to warm to room temperature and stirred at room temperature overnight. Water was added and the organic phase separated. The organic phase was washed with brine, dried over a hydrophobic frit and concentrated under reduced pressure to yield 6-benzyloxy-2-methyl-5-nitro-indazole. LCMS: ES+284.1. $^1$H NMR (400 MHz, CDCl$_3$) 8.22 (1H, s), 8.01 (1H, s), 7.51-7.47 (2H, m), 7.41-7.31 (3H, m), 7.15 (1H, s), 5.25 (2H, s), 4.20 (3H, s).

6-Benzyloxy-2-methyl-5-nitro-indazole (390 mg, 1.38 mmol, 1.00 eq) and tin(II) chloride dihydrate (1243 mg, 5.51 mmol, 4.00 eq) in dichloromethane (10 mL) and ethyl acetate (10 mL) were stirred overnight at room temperature. The mixture was filtered through celite and concentrated under reduced pressure to yield 6-benzyloxy-2-methyl-indazol-5-amine, which was used crude in the next step.

6-Benzyloxy-2-methyl-indazol-5-amine (50 mg, 0.197 mmol, 1.00 eq), 5-[(3R)-3-[tert-butoxycarbonyl(methyl)amino]pyrrolidin-1-yl]pyrazine-2-carboxylic acid (80 mg, 0.248 mmol, 1.00 eq), chloro-N,N,N',N'-tetramethylformamidinium hexafluorophosphate (105 mg, 0.373 mmol, 1.50 eq), and 1-methylimidazole (0.059 mL, 0.745 mmol, 3.00 eq) in acetonitrile (2 mL) were stirred at room temperature overnight. Water and ethyl acetate were added, the organic phase was separated and dried over a hydrophobic frit. The organic phase was concentrated under reduced pressure to yield tert-butyl N-[(3R)-1-[5-[(6-benzyloxy-2-methyl-indazol-5-yl)carbamoyl]pyrazin-2-yl]pyrrolidin-3-yl]-N-methyl-carbamate, which was used crude in the next step.

tert-Butyl N-[(3R)-1-[5-[(6-benzyloxy-2-methyl-indazol-5-yl)carbamoyl]pyrazin-2-yl]pyrrolidin-3-yl]-N-methyl-carbamate (180 mg, 0.323 mmol, 1.00 eq) and trifluoroacetic acid (0.25 mL, 3.23 mmol, 10.0 eq) in dichloromethane (2 mL) were stirred at room temperature for 2 h. The reaction mixture was concentrated under reduced pressure and purified by prep-HPLC followed by achiral SFC to yield (R)-N-(6-(benzyloxy)-2-methyl-2H-indazol-5-yl)-5-(3-(methylamino)pyrrolidin-1-yl)pyrazine-2-carboxamide. LCMS (ES+) 458.2 (M+H)+, RT 3.23 min (Analytical method AcHSSC18). $^1$H NMR (400 MHz, DMSO-d$_6$) 10.30 (1H, s), 8.76 (1H, d, J=1.4 Hz), 8.68 (1H, s), 8.24 (1H, s), 7.94 (1H, d, J=1.5 Hz), 7.63-7.61 (2H, m), 7.53-7.48 (2H, m), 7.41-7.37 (1H, m), 7.22 (1H, s), 5.36 (2H, s), 4.10 (3H, s), 3.71-3.57 (3H, m), 3.44-3.39 (1H, m), 3.31-3.28 (1H, m), 2.35-2.31 (3H, m), 2.16-2.10 (1H, m), 1.95-1.87 (2H, m).

Example 9: (R)-5-(3-(cyclopropylamino)pyrrolidin-1-yl)-N-(6-(2-methoxyethoxy)-2-methyl-2H-indazol-5-yl)pyrazine-2-carboxamide

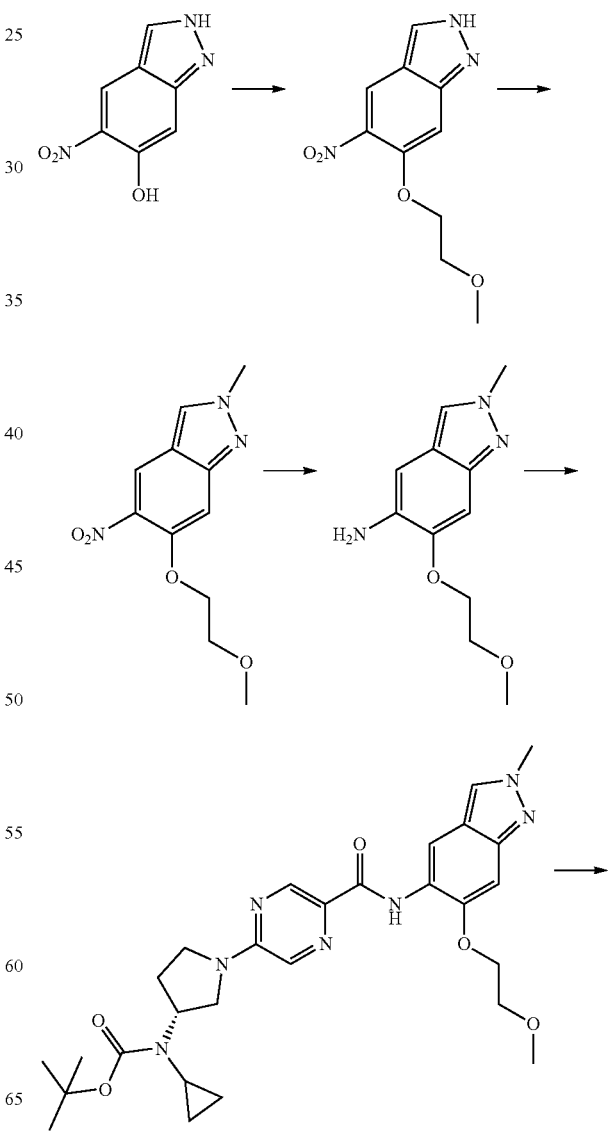

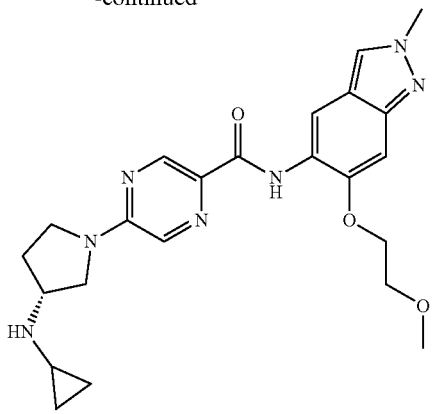

5-Nitro-2H-indazol-6-ol (500 mg, 2.79 mmol, 1.00 eq), 2-methoxyethanol (0.22 mL, 2.79 mmol, 1.00 eq), and ethylenebis(diphenylphosphine) (834 mg, 2.09 mmol, 0.750 eq) in tetrahydrofuran (20 mL) were stirred at 0° C. Diisopropyl azodicarboxylate (0.82 mL, 4.19 mmol, 1.50 eq) was added dropwise and reaction mixture warmed to room temperature overnight. Water was added and the product extracted into ethyl acetate. The organic phase was dried over a hydrophobic frit and purified by flash chromatography on silica using a 0-100% ethyl acetate in cyclohexane gradient. The appropriate fractions were combined and concentrated under reduced pressure to yield 6-(2-methoxyethoxy)-5-nitro-1H-indazole. $^1$H NMR (400 MHz, DMSO-$d_6$) 13.42-13.38 (1H, m), 8.46 (1H, s), 8.24 (1H, s), 7.29 (1H, s), 4.38-4.34 (2H, m), 3.78-3.75 (2H, m), 3.37 (3H, s).

6-(2-Methoxyethoxy)-5-nitro-1H-indazole (380 mg, 1.44 mmol, 1.00 eq) in ethyl acetate (10.00 mL) was stirred at 0° C. Trimethyloxonium tetrafluoroborate (213 mg, 1.44 mmol, 1.00 eq) was added portionwise and reaction mixture allowed to warm to room temperature. The reaction mixture was stirred at room temperature overnight. Water was added and the product extracted into ethyl acetate. The organic phase was dried over a hydrophobic frit and concentrated under reduced pressure to yield 6-(2-methoxyethoxy)-2-methyl-5-nitro-indazole. $^1$H NMR (400 MHz, DMSO-$d_6$) 8.59 (1H, s), 8.45-8.44 (1H, m), 7.32-7.31 (1H, m), 4.32-4.29 (2H, m), 4.21 (3H, s), 3.76-3.73 (2H, m), 3.37 (3H, s).

6-(2-Methoxyethoxy)-2-methyl-5-nitro-indazole (340 mg, 1.35 mmol, 1.00 eq) and tin(II) chloride dihydrate (1221 mg, 5.41 mmol, 4.00 eq) in ethyl acetate (5 mL) and dichloromethane (5 mL) were stirred at room temperature overnight. The reaction mixture was filtered through celite and concentrated under reduced pressure to yield 6-(2-methoxyethoxy)-2-methyl-indazol-5-amine. LCMS (ES+) 222 (M+H).

6-(2-Methoxyethoxy)-2-methyl-indazol-5-amine (50 mg, 0.226 mmol, 1.00 eq), [5-[(3R)-3-[tert-butoxycarbonyl(cyclopropyl)amino]pyrrolidin-1-yl]pyrazine-2-carbonyl]oxylithium (80 mg, 0.226 mmol, 1.00 eq), chloro-N,N,N',N'-tetramethylformamidinium hexafluorophosphate (95 mg, 0.339 mmol, 1.50 eq), and 1-methylimidazole (0.05 mL, 0.68 mmol, 3.0 eq) in acetonitrile (2 mL) were stirred at room temperature overnight. Water was added and the product extracted into ethyl acetate. The organic phase was dried over a hydrophobic frit and concentrated under reduced pressure to yield tert-butyl N-cyclopropyl-N-[(3R)-1-[5-[[6-(2-methoxyethoxy)-2-methyl-indazol-5-yl]carbamoyl]pyrazin-2-yl]pyrrolidin-3-yl]carbamate. LCMS (ES+) 552 (M+H)+.

tert-Butyl N-cyclopropyl-N-[(3R)-1-[5-[[6-(2-methoxyethoxy)-2-methyl-indazol-5-yl]carbamoyl]pyrazin-2-yl]pyrrolidin-3-yl]carbamate (95 mg, 0.17 mmol, 1.0 eq) and 4 M hydrogen chloride in 1,4-dioxane (0.43 mL, 1.72 mmol, 10.0 eq) in 1,4-dioxane (2 mL) were stirred at room temperature for 4 h. The reaction mixture was concentrated under reduced pressure, dissolved in DMSO and purified by prep-HPLC to yield (R)-5-(3-(cyclopropylamino)pyrrolidin-1-yl)-N-(6-(2-methoxyethoxy)-2-methyl-2H-indazol-5-yl)pyrazine-2-carboxamide. LCMS (ES+) 452.5 (M+H)+, RT 2.51 min (Analytical method AcHSSC18). $^1$H NMR (400 MHz, DMSO-$d_6$) 10.15 (1H, s), 8.73 (1H, d, J=1.4 Hz), 8.67-8.66 (1H, m), 8.21-8.20 (1H, m), 7.96 (1H, d, J=1.3 Hz), 7.11 (1H, s), 4.31-4.27 (2H, m), 4.08 (3H, s), 3.83-3.79 (2H, m), 3.72-3.47 (4H, m), 3.40-3.39 (4H, m), 2.13-2.09 (2H, m), 1.96-1.89 (1H, m), 0.42-0.38 (2H, m), 0.27-0.20 (2H, m). One peak not visible due to overlap with DMSO or $H_2O$.

Example 10: N-(6-(benzyloxy)-2-methyl-2H-indazol-5-yl)-5-(6-methyl-2,6-diazaspiro[3.5]nonan-2-yl)pyrazine-2-carboxamide

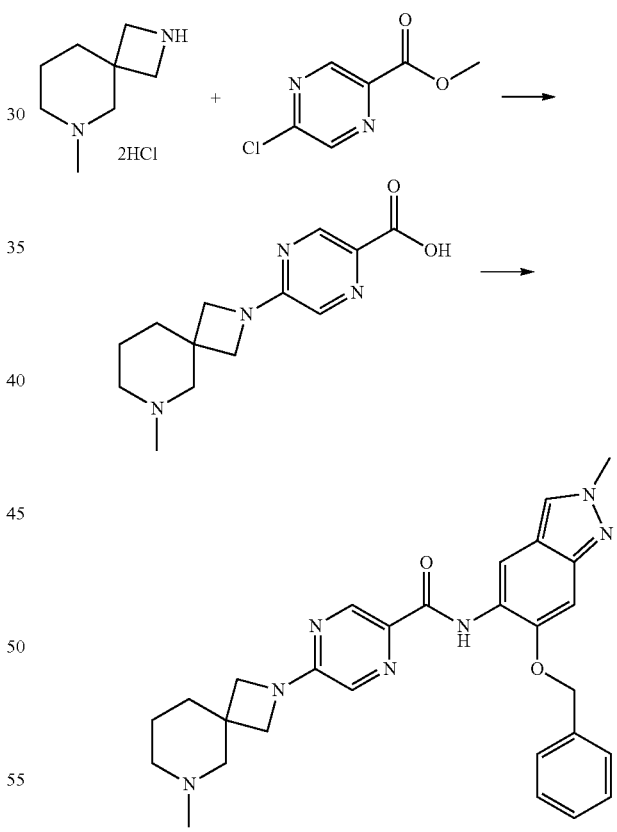

To a suspension of 6-methyl-2,6-diazaspiro[3.5]nonane; hydrochloride (500 mg, 2.83 mmol, 1.00 eq) and triethylamine (1.2 mL, 8.49 mmol, 3.00 eq) in 1,4-dioxane (10 mL) were added methyl 5-chloro-2-pyrazinecarboxylate (488 mg, 2.83 mmol, 1.00 eq). The reaction mixture was heated to 100° C. for 2 h. Sodium hydroxide (170 mg, 4.24 mmol, 1.50 eq) and water (10 mL) were added and the mixture stirred at 50° C. for 4 h. The reaction was acidified with 1M aqueous HCl and loaded onto SCX cartridge. The cartridge was washed with methanol and product eluted with 7N ammonia in methanol. The solution was concentrated under reduced pressure to yield 5-(8-methyl-2,8-diazaspiro[3.5]nonan-2-yl)pyrazine-2-carboxylic acid. LCMS (ES−) 261 (M−H)−.

6-Benzyloxy-2-methyl-indazol-5-amine (100 mg, 0.395 mmol, 1.00 eq), 5-(8-methyl-2,8-diazaspiro[3.5]nonan-2-yl)pyrazine-2-carboxylic acid (104 mg, 0.395 mmol, 1.00 eq), chloro-N,N,N',N'-tetramethylformamidinium hexafluorophosphate (166 mg, 0.592 mmol, 1.50 eq), and 1-methylimidazole (0.094 mL, 1.18 mmol, 3.00 eq) in acetonitrile (2 mL) were stirred at room temperature overnight. The reaction mixture was diluted with ethyl acetate and water. The organic phase was separated, dried over a hydrophobic frit and concentrated under reduced pressure. The residue was purified by prep-HPLC to yield N-(6-(benzyloxy)-2-methyl-2H-indazol-5-yl)-5-(6-methyl-2,6-diazaspiro[3.5]nonan-2-yl)pyrazine-2-carboxamide. LCMS (ES+) 498.2 (M+H)+, RT 3.18 min (Analytical method AcHSSC18). $^1$H NMR (400 MHz, DMSO-$d_6$) 10.30 (1H, s), 8.73 (1H, d, J=1.3 Hz), 8.67 (1H, s), 8.25-8.24 (1H, m), 7.84 (1H, d, J=1.4 Hz), 7.63-7.60 (2H, m), 7.53-7.48 (2H, m), 7.41-7.37 (1H, m), 7.23 (1H, s), 5.36 (2H, s), 4.10 (3H, s), 3.93-3.85 (4H, m), 2.47-2.44 (2H, m), 2.22-2.20 (5H, m), 1.69-1.65 (2H, m), 1.57-1.51 (2H, m).

Example 11: N-(2-methyl-6-(prop-2-yn-1-yloxy)-2H-indazol-5-yl)-5-(6-methyl-2,6-diazaspiro[3.5]nonan-2-yl)pyrazine-2-carboxamide

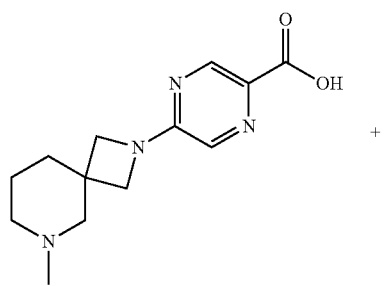

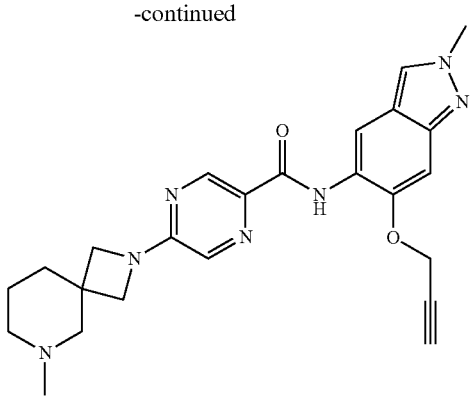

-continued

A solution of 2-methyl-6-prop-2-ynoxy-indazol-5-amine (100 mg, 0.497 mmol, 1 eq), 5-(8-methyl-2,8-diazaspiro[3.5]nonan-2-yl)pyrazine-2-carboxylic acid (130 mg, 0.497 mmol, 1 eq), chloro-N,N,N',N'-tetramethylformamidinium hexafluorophosphate (209 mg, 0.745 mmol, 1.5 eq), and 1-methylimidazole (0.12 mL, 1.49 mmol, 3 eq) in acetonitrile (2 mL) were stirred at room temperature overnight. Ethyl acetate and water were added. The organic phase was separated, dried over a hydrophobic frit and concentrated under reduced pressure. The residue was purified by prep-HPLC to yield N-(2-methyl-6-(prop-2-yn-1-yloxy)-2H-indazol-5-yl)-5-(6-methyl-2,6-diazaspiro[3.5]nonan-2-yl)pyrazine-2-carboxamide. LCMS (ES+) 446.2 (M+H)+, RT 2.7 min (Analytical method AcHSSC18). $^1$H NMR (400 MHz, DMSO-$d_6$) 10.00 (1H, s), 8.73 (1H, d, J=1.4 Hz), 8.70 (1H, s), 8.26 (1H, s), 7.92 (1H, d, J=1.4 Hz), 7.23 (1H, s), 5.06 (2H, d, J=2.4 Hz), 4.11 (3H, s), 3.91-3.83 (4H, m), 3.68 (1H, t, J=2.3 Hz), 2.50-2.39 (2H, m), 2.29-2.20 (5H, m), 1.65-1.65 (2H, m), 1.57-1.51 (2H, m).

Example 12: N-(4-fluoro-2-methylbenzo[d]oxazol-6-yl)-5-(3-((isopropylamino)methyl)azetidin-1-yl)pyrazine-2-carboxamide

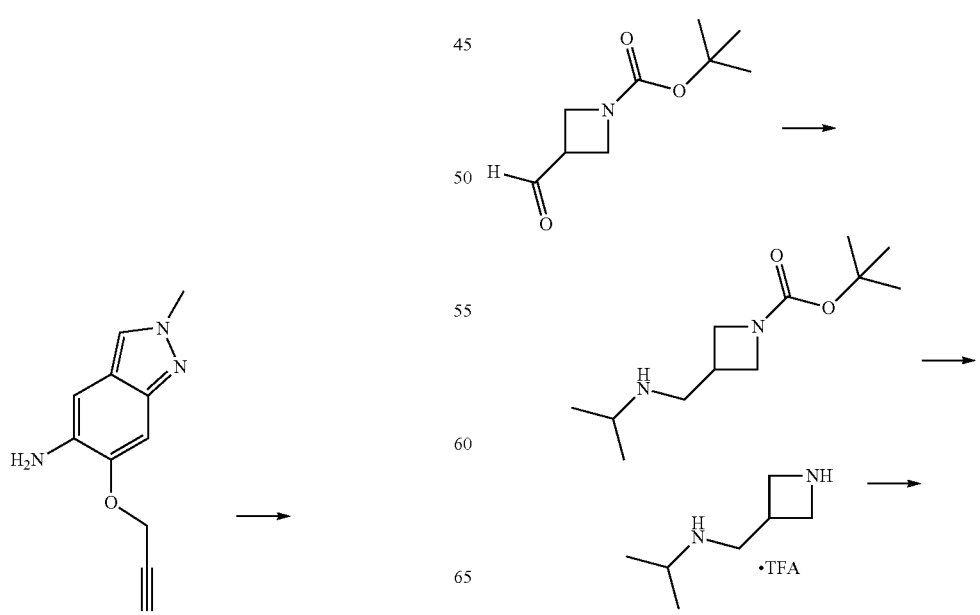

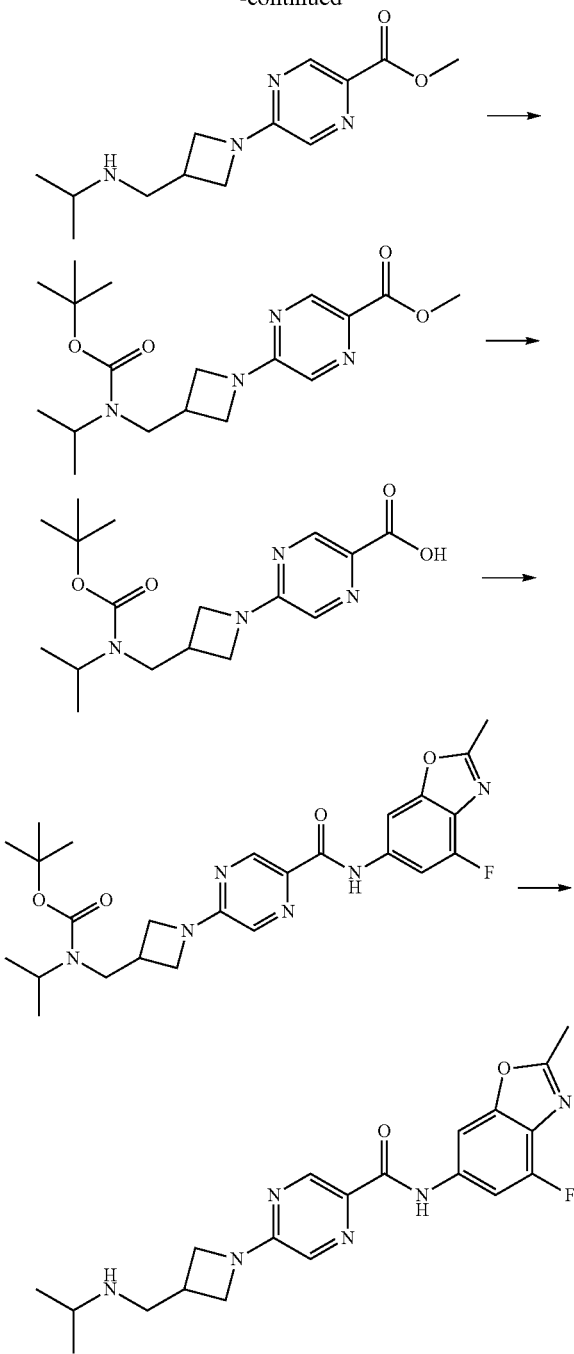

tert-Butyl 3-formylazetidine-1-carboxylate (300 mg, 1.62 mmol) was dissolved in dichloromethane (15 mL) and isopropylamine (0.14 mL, 1.62 mmol) was added at RT. Sodium triacetoxyborohydride (755 mg, 3.56 mmol) was added and the reaction stirred at RT for 18 h. The reaction was quenched with saturated sodium hydrogencarbonate and stirred for 20 minutes. The layers were separated using a phase separator and the aqueous layer was further extracted using DCM×3. The DCM was removed in vacuo to give tert-butyl 3-((isopropylamino)methyl)azetidine-1-carboxylate. The material was used in the next step without further purification.

tert-Butyl 3-((isopropylamino)methyl)azetidine-1-carboxylate (350 mg, 1.53 mmol) was dissolved in dichloromethane (3 mL) and trifluoroacetic acid (1.0 mL, 13.1 mmol) was added at RT. The reaction was stirred at RT for 2 h and the solvent was removed in vacuo to give N-(azetidin-3-ylmethyl)propan-2-amine; bis-2,2,2-trifluoroacetic acid. The crude product was used in the next step without further purification.

Methyl 5-chloro-2-pyrazinecarboxylate (140 mg, 0.814 mmol) and N-(azetidin-3-ylmethyl)propan-2-amine; bis-2,2,2-trifluoroacetic acid (290 mg, 0.814 mmol) were dissolved in acetonitrile (10 mL) and triethylamine (0.45 mL, 3.26 mmol) was added. The reaction was heated to 45° C. for 18 h. The reaction was cooled to RT and the solvent was removed in vacuo to give a residue. The residue was dissolved in DCM and washed with saturated sodium hydrogencarbonate. The DCM was separated using a phase separator and the DCM layer concentrated in vacuo to give a residue. The residue was purified by silica chromatography (10 g, eluting with EtOAc in cyclohexane 0-100%) to give methyl 5-(3-((isopropylamino)methyl)azetidin-1-yl)pyrazine-2-carboxylate.

Methyl 5-[3-[(isopropylamino)methyl]azetidin-1-yl]pyrazine-2-carboxylate (215 mg, 0.814 mmol) was dissolved in dichloromethane (10 mL) and di-tert-butyl dicarbonate (0.21 mL, 0.895 mmol) and 4-(dimethylamino)pyridine (10 mg, 0.081 mmol) was added. The reaction was stirred at RT for 18 h. The solvent was removed in vacuo and the residue was purified by silica chromatography (10 g, eluting with EtOAc in cyclohexane 0-100%) to give methyl 5-(3-(((tert-butoxycarbonyl)(isopropyl)amino)methyl)azetidin-1-yl)pyrazine-2-carboxylate.

Methyl 5-[3-[[tert-butoxycarbonyl(isopropyl)amino]methyl]azetidin-1-yl]pyrazine-2-carboxylate (130 mg, 0.357 mmol) was dissolved in methyl alcohol (3 mL) and water (1.5 mL) and lithium hydroxide (9.4 mg, 0.392 mmol) was added at RT. The reaction was stirred at RT for 18 h. The solvent was removed in vacuo to give a residue. Water (1 mL) was added to the residue and the pH adjusted to ~3 with 1M HCl. The aqueous layer was extracted with EtOAc×3 and the organic layer was dried by passing through a hydrophobic frit. The solvent was removed in vacuo to give 5-(3-(((tert-butoxycarbonyl)(isopropyl)amino)methyl)azetidin-1-yl)pyrazine-2-carboxylic acid. The crude material was used in the next step without further purification.

5-[3-[[tert-Butoxycarbonyl(isopropyl)amino]methyl]azetidin-1-yl]pyrazine-2-carboxylic acid (95 mg, 0.271 mmol) and 4-fluoro-2-methyl-1,3-benzoxazol-6-amine (45 mg, 0.271 mmol) were dissolved in acetonitrile (3 mL). 1-Methylimidazole (0.065 mL, 0.813 mmol) was added followed by chloro-N,N,N',N'-tetramethylformamidinium hexafluorophosphate (84 mg, 0.298 mmol). The reaction was stirred at RT for 18 h. The reaction mixture was filtered to collect a solid and the solid washed with acetonitrile and water to give tert-butyl ((1-(5-((4-fluoro-2-methylbenzo[d]oxazol-6-yl)carbamoyl)pyrazin-2-yl)azetidin-3-yl)methyl)(isopropyl)carbamate. The material was used in the next step without further purification.

tert-Butyl N-[[1-[5-[(4-fluoro-2-methyl-1,3-benzoxazol-6-yl)carbamoyl]pyrazin-2-yl]azetidin-3-yl]methyl]-N-isopropyl-carbamate (82 mg, 0.164 mmol) was dissolved in dichloromethane (3 mL) and trifluoroacetic acid (1.0 mL, 13.1 mmol) was added. The reaction was stirred at RT for 1 h. The solvent was removed by blowing nitrogen over the sample, and the sample was further dried in vacuum oven overnight. The resulting residue was dissolved in DCM/MeOH 9:1 (2 mL) and MP-carbonate was added, and the sample was left for 18 h at RT. The MP-carbonate was removed by filtration and the solvent removed in vacuo to give the title compound. LCMS (ES+) 399.2 (M+H)+, RT 2.91 min (Analytical method AcHSSC18); ¹H NMR (400 MHz, DMSO-d$_6$) d 10.57 (s, 1H), 8.72 (d, J=1.3 Hz, 1H), 8.18 (d, J=1.5 Hz, 1H), 7.85-7.80 (m, 2H), 4.23 (dd, J=8.3, 8.3 Hz, 2H), 3.88 (dd, J=5.1, 9.1 Hz, 2H), 2.87-2.76 (m, 4H), 2.61 (s, 3H), 1.00 (d, J=6.3 Hz, 6H) NH not observed); ¹⁹F NMR (400 MHz, DMSO-d$_6$) d −126.11 (d, J=12.5 Hz, 1F).

Example 13: 5-((3S,4R)-3-(cyclopropylamino)-4-methylpyrrolidin-1-yl)-N-(8-fluoro-2-methylimidazo[1,2-a]pyridin-6-yl)pyrazine-2-carboxamide

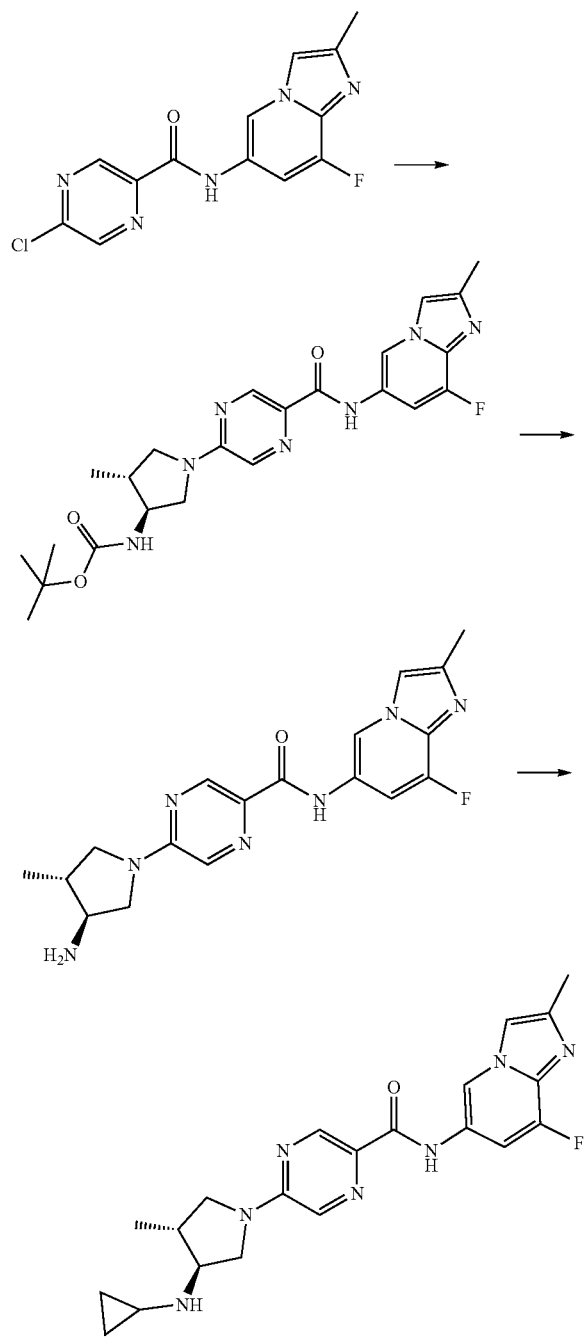

tert-Butyl N-[(3S,4R)-4-methylpyrrolidin-3-yl]carbamate (125 mg, 0.624 mmol) and 5-chloro-N-(8-fluoro-2-methylimidazo[1,2-a]pyridin-6-yl)pyrazine-2-carboxamide (191 mg, 0.624 mmol) were dissolved in acetonitrile (5 mL) and triethylamine (0.26 mL, 1.87 mmol) was added. The reaction was heated at 45° C. for 18 h. The reaction was cooled to RT and the solvent removed in vacuo to give a residue, which was purified by silica chromatography (10 g, eluting with EtOAc/cyclohexane) to give tert-butyl ((3S,4R)-1-(5-((8-fluoro-2-methylimidazo[1,2-a]pyridin-6-yl)carbamoyl)pyrazin-2-yl)-4-methylpyrrolidin-3-yl)carbamate.

tert-Butyl ((3S,4R)-1-(5-((8-fluoro-2-methylimidazo[1,2-a]pyridin-6-yl)carbamoyl)pyrazin-2-yl)-4-methylpyrrolidin-3-yl)carbamate (220 mg, 0.469 mmol) was dissolved in dichloromethane (3 mL) and trifluoroacetic acid (1.0 mL) was added at RT and the reaction was stirred for 1 h. The solvent was removed in vacuo to give a residue. The residue was purified by SCX chromatography (10 g, eluting with MeOH and then 10% 7M NH$_3$ in MeOH/MeOH). The ammoniacal fraction was concentrated in vacuo to give 5-((3S,4R)-3-amino-4-methylpyrrolidin-1-yl)-N-(8-fluoro-2-methylimidazo[1,2-a]pyridin-6-yl)pyrazine-2-carboxamide.

5-((3S,4R)-3-Amino-4-methylpyrrolidin-1-yl)-N-(8-fluoro-2-methylimidazo[1,2-a]pyridin-6-yl)pyrazine-2-carboxamide (173 mg, 0.468 mmol) was dissolved in methyl alcohol (10 mL) and acetic acid (0.029 mL, 0.515 mmol) was added at RT. (1-Ethoxycyclopropoxy)trimethylsilane (0.094 mL, 0.468 mmol) was added and the reaction stirred at RT for 18 h. Sodium cyanoborohydride (32 mg, 0.515 mmol) was added at RT and the reaction stirred for a further 18 h at RT. The reaction was quenched by addition of saturated sodium hydrogencarbonate and extracted with DCM×3. The layers were separated using a phase separator and the solvent removed in vacuo to give a residue, which was purified by preparative HPLC followed by achiral SFC to give the title compound. LCMS (ES+) 410.2 (M+H)+, RT 2.15 min (Analytical method AcHSSC18); ¹H NMR (400 MHz, DMSO-d$_6$) d 10.41 (s, 1H), 9.18 (d, J=1.5 Hz, 1H), 8.73 (d, J=1.3 Hz, 1H), 7.95 (d, J=1.1 Hz, 1H), 7.88 (d, J=2.9 Hz, 1H), 7.55 (dd, J=1.6, 13.1 Hz, 1H), 3.93-3.77 (m, 2H), 3.38-3.30 (m, 1H), 3.19-3.12 (m, 1H), 3.04-3.02 (m, 1H), 2.53 (dd, J=2.4, 6.2 Hz, 1H), 2.33 (s, 3H), 2.19-2.15 (m, 2H), 1.07 (d, J=6.8 Hz, 3H), 0.44-0.40 (m, 2H), 0.28-0.20 (m, 2H); ¹⁹F NMR (400 MHz, DMSO-d$_6$) d −132.19 (dd, J=3.5, 12.7 Hz, 1F).

Example 14: N-(4-fluoro-2-methylbenzo[d]oxazol-6-yl)-5-(methyl(piperidin-4-yl)amino)pyrazine-2-carboxamide

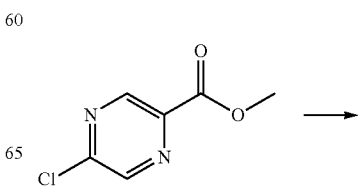

-continued

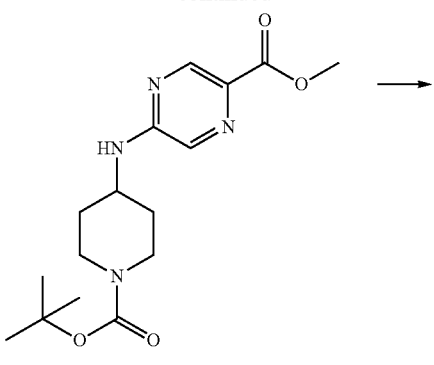

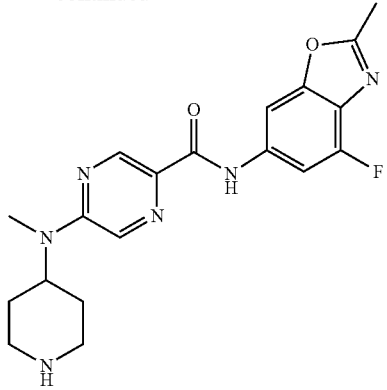 [SMILES: Cc1nc2c(F)cc(NC(=O)c3cnc(N(C)C4CCNCC4)cn3)cc2o1]

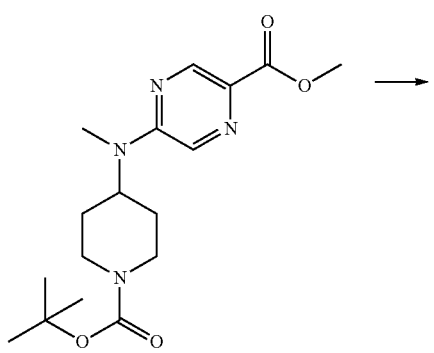

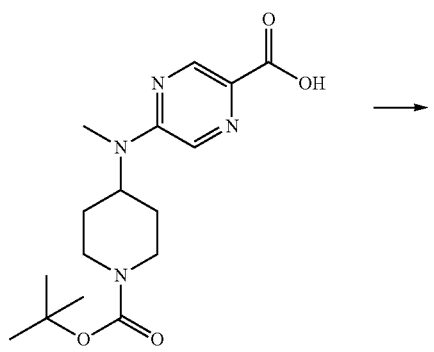

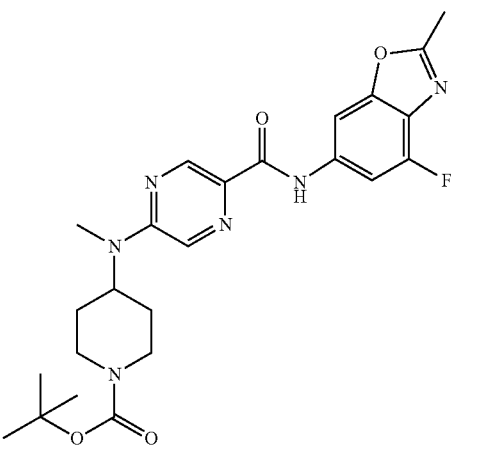

4-Amino-1-Boc-piperidine (671 mg, 3.35 mmol), methyl 5-chloro-2-pyrazinecarboxylate (578 mg, 3.35 mmol), cesium carbonate (2194 mg, 6.73 mmol) and 1,4-dioxane (35 mL) were combined and heated at reflux for 18 h. The reaction was cooled to RT and the solids removed by filtering through Celite. The solvent was removed in vacuo to give a residue, which was purified by silica chromatography (25 g, eluting with EtOAc/cyclohexane 0-100%) to give methyl 5-((1-(tert-butoxycarbonyl)piperidin-4-yl)amino)pyrazine-2-carboxylate.

Methyl 5-[(1-tert-butoxycarbonyl-4-piperidyl)amino]pyrazine-2-carboxylate (534 mg, 1.59 mmol) was dissolved in N,N-dimethylformamide (15 mL) and sodium hydride (60%, 95 mg, 2.38 mmol) was added at RT and stirred for 1 h. Iodomethane (0.15 mL, 2.38 mmol) was added and the reaction was stirred for a further 18 h at RT. The reaction was quenched with MeOH (used to avoid ester hydrolysis) and the solvent was removed in vacuo to yield methyl 5-((1-(tert-butoxycarbonyl)piperidin-4-yl)(methyl)amino)pyrazine-2-carboxylate. The material was used in the next step without further purification.

Methyl 5-[(1-tert-butoxycarbonyl-4-piperidyl)-methylamino]pyrazine-2-carboxylate (556 mg, 1.59 mmol) was dissolved in methyl alcohol (12 mL) and water (6 mL). Lithium hydroxide (57 mg, 2.38 mmol) was added and the reaction stirred at RT for 18 h. The solvent was removed in vacuo to give an aqueous solution. The pH was adjusted to ~3 with 1M HCl to give a solid. The solid was collected by filtration, washed with water and dried in a vacuum oven overnight to give 5-((1-(tert-butoxycarbonyl)piperidin-4-yl)(methyl)amino)pyrazine-2-carboxylic acid. The material was used in the next step without further purification.

4-Fluoro-2-methyl-1,3-benzoxazol-6-amine (80 mg, 0.481 mmol), 5-[(1-tert-butoxycarbonyl-4-piperidyl)-methyl-amino]pyrazine-2-carboxylic acid (100 mg, 0.297 mmol), and 1-methylimidazole (0.12 mL, 1.44 mmol) were suspended in acetonitrile (8 mL), and chloro-N,N,N',N'-tetramethylformamidinium hexafluorophosphate (149 mg, 0.530 mmol) was added and stirred at RT for 18 h. The solvent was removed in vacuo and the residue purified by silica chromatography (10 g, eluting with EtOAc/cyclohexane 0-100%) to give tert-butyl 4-((5-((4-fluoro-2-methylbenzo[d]oxazol-6-yl)carbamoyl)pyrazin-2-yl)(methyl)amino)piperidine-1-carboxylate.

tert-Butyl 4-[[5-[(4-fluoro-2-methyl-1,3-benzoxazol-6-yl)carbamoyl]pyrazin-2-yl]-methyl-amino]piperidine-1-carboxylate (82 mg, 0.169 mmol,) was dissolved in dichloromethane (3 mL) and trifluoroacetic acid (1.0 mL, 13.1 mmol) was added at RT. The reaction was stirred at RT for 1 h. The solvent removed in vacuo to give a residue, which was dried in a vacuum oven overnight. The resulting residue was dissolved in DCM/MeOH 9:1 (2 mL) and MP-carbonate was added, and the sample was left for 18 h at RT. The MP-carbonate was removed by filtration and the solvent removed in vacuo to give a residue, which was purified by achiral SFC to give the title compound. LCMS (ES+) 385.2 (M+H)+, RT 2.69 min (Analytical method AcHSSC18); $^1$H NMR (400 MHz, DMSO-d$_6$) d 10.54 (s, 1H), 8.75 (d, J=1.3 Hz, 1H), 8.18 (d, J=1.5 Hz, 1H), 8.15 (d, J=1.3 Hz, 1H), 7.82 (dd, J=1.7, 12.8 Hz, 1H), 4.63-4.55 (m, 1H), 3.06-2.99 (m, 5H), 2.63-2.55 (m, 5H), 2.34-2.18 (m, 1H), 1.71-1.54 (m, 4H); $^{19}$F NMR (400 MHz, DMSO-d$_6$) d −126.11 (d, J=12.5 Hz, 1F).

Example A: N-(7-chloro-2-methylpyrazolo[1,5-a]pyridin-5-yl)-5-(3-((cyclopropylamino)methyl) azetidin-1-yl)pyrazine-2-carboxamide

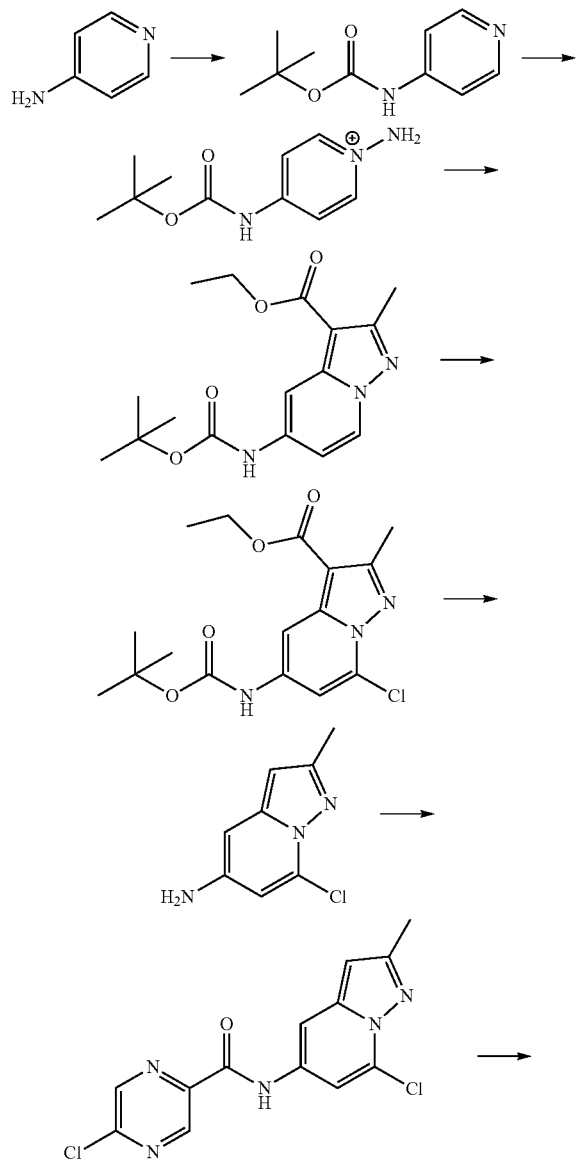

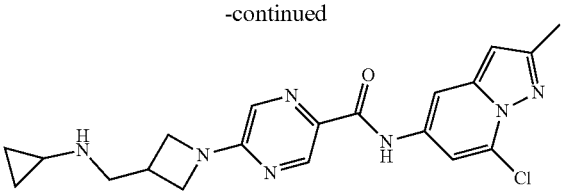

4-Aminopyridine (3 g, 31.9 mmol) was dissolved in EtOAc and di-tert-butyl dicarbonate (7.3 mL, 31.9 mmol) was added. The reaction mixture was stirred at r.t. for 1.5 h. The reaction mixture was partitioned between EtOAc and water. The aqueous phase was extracted with EtOAc (×3) and the combined organic phases were filtered through a hydrophobic frit. The solvent was concentrated in vacuo to give the desired product. LCMS (ES+) 195.3 (M+H)+, R.T. 1.06 min. $^1$H NMR (400 MHz, CDCl$_3$) d 8.44 (dd, J=1.5, 4.8 Hz, 2H), 7.33-7.29 (m, 2H), 6.83 (s, 1H), 1.53 (s, 9H).

4-(Boc-amino)pyridine (7.22 g, 37.1 mmol) was dissolved in N,N-dimethylformamide (50.00 mL) and O-(2,4-dinitrophenyl)hydroxylamine (8.14 g, 40.9 mmol) was added at r.t. The reaction mixture was stirred at r.t. for 16 h, and this was used directly in the next step. LCMS (ES+) 210 (M+H)+, R.T. 1.05 min (broad signal).

To tert-butyl N-(1-aminopyridin-1-ium-4-yl)carbamate 2,4-dinitrophenolate (14 g, 35.6 mmol) in N,N-dimethylformamide (50 mL) were added ethyl 2-butynoate (2.0 mL, 17.2 mmol) and potassium carbonate (7.38 g, 53.4 mmol) at r.t. The reaction was stirred at r.t. for 48 h. The reaction mixture was filtered, and the precipitate was washed with EtOAc. The filtrate was concentrated in vacuo to give a residue. The crude was purified by column chromatography on silica gel, eluting with EtOAc/cyclohexane 0-100% to give the desired product. LCMS (ES+) 319 (M+H)+, R.T. 1.66 min.

Ethyl 5-(tert-butoxycarbonylamino)-2-methyl-pyrazolo[1,5-a]pyridine-3-carboxylate (537 mg, 1.68 mmol) was stirred in dry THF (10 mL) at −80° C. To this, n-butyllithium solution (1.4 mL, 3.53 mmol, 2.5 M) was added dropwise, and the reaction was stirred at −80° C. for 15 mins. p-Toluenesulfonyl chloride (1.3 g, 6.73 mmol) in dry THF (1 mL) was added to the reaction at −80° C. The reaction was stirred for 5 mins and the ice bath was removed. The reaction was stirred for a further 20 mins. The reaction mixture was diluted with EtOAc and washed with brine. The organic layer was passed through a hydrophobic frit and concentrated in vacuo to give the crude product. LCMS (ES+) 353 (M+H)+, R.T. 1.75 min.

Ethyl 5-(tert-butoxycarbonylamino)-7-chloro-2-methylpyrazolo[1,5-a]pyridine-3-carboxylate (420 mg, 1.19 mmol) and hydrogen bromide (48%, 1.8 mL, 15.9 mmol) were refluxed together for 17 h. The reaction mixture was concentrated in vacuo and the residue was loaded onto a 5 g SCX cartridge (preconditioned with MeOH). The residue was eluted with MeOH, then NH$_3$ (7 M) in MeOH. The ammonia fraction was concentrated in vacuo to give the desired product. LCMS (ES+) 181 (M+H)+, R.T. 1.14 min.

7-Chloro-2-methyl-pyrazolo[1,5-a]pyridin-5-amine (150 mg, 0.826 mmol), 5-chloro-2-pyrazinecarboxylic acid (131 mg, 0.826 mmol), chloro-N,N,N',N'-tetramethylformamidinium hexafluorophosphate (348 mg, 1.24 mmol), and 1-methylimidazole (0.20 mL, 2.48 mmol) in MeCN (8 mL) was stirred under nitrogen for 1 h at r.t. The reaction mixture was concentrated in vacuo, diluted with DCM, and washed with aqueous sodium bicarbonate solution. The organic layer was concentrated onto silica and purified by column chromatography, eluting with cyclohexane and EtOAc (0-35% gradient). The appropriate fractions were combined and concentrated in vacuo to give the desired product. LCMS (ES+) 322 (M+H)+, R.T. 1.52 min. $^1$H NMR (400 MHz, CDCl$_3$) δ 9.52 (s, 1H), 9.28 (d, J=1.5 Hz, 1H), 8.60 (d, J=1.3 Hz, 1H), 8.07 (d, J=2.0 Hz, 1H), 7.13 (d, J=2.0 Hz, 1H), 6.42 (s, 1H), 2.55 (s, 3H).

Triethylamine (0.035 mL, 0.251 mmol), 5-chloro-N-(7-chloro-2-methyl-pyrazolo[1,5-a]pyridin-5-yl)pyrazine-2-carboxamide (27 mg, 0.0838 mmol), and N-(azetidin-3-ylmethyl)cyclopropanamine (11 mg, 0.0838 mmol) were combined in MeCN (6 mL) and stirred at 40° C. for 1 h. The reaction was stopped and the mixture concentrated in vacuo. The crude material provided was submitted to achiral SFC for purification. LCMS (ES+) 412 (M+H)+, R.T. 2.86 min (Analytical method AcHSSC18. NMR: $^1$H NMR (400 MHz, DMSO-d$_6$) δ 10.55 (s, 1H), 8.71 (d, J=1.4 Hz, 1H), 8.27 (d, J=2.0 Hz, 1H), 7.83 (d, J=1.3 Hz, 1H), 7.63 (d, J=2.1 Hz, 1H), 6.48 (s, 1H), 4.22 (dd, J=8.3, 8.3 Hz, 2H), 3.88-3.79 (m, 2H), 2.89-2.84 (m, 3H), 2.39 (s, 3H), 2.08-2.03 (m, 1H), 0.39-0.34 (m, 2H), 0.22-0.18 (m, 2H).

Further analogues were prepared using the same chemistry as described in Example A, from commercially available or synthesised amines. Final products were isolated by Preparative HPLC.

Example B: 5-(3-((cyclopropylamino)methyl)azetidin-1-yl)-N-(6-ethoxy-2-methyl-2H-indazol-5-yl)pyrazine-2-carboxamide

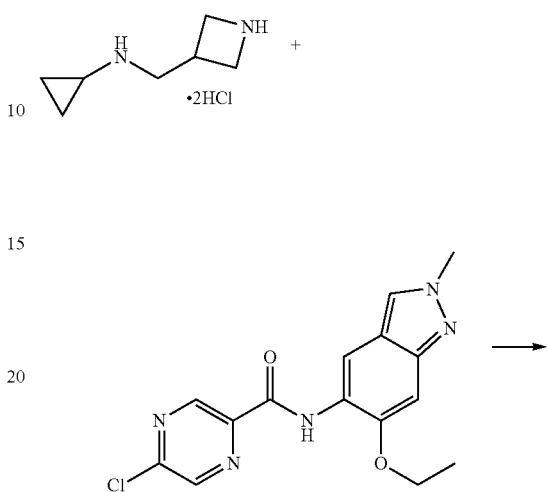

| Ex. | Structure | Analytical data |
|---|---|---|
| 15 | 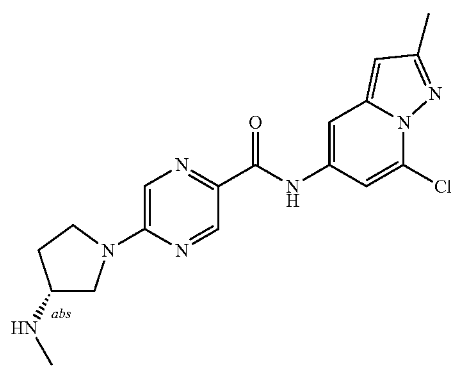 [SMILES: CN[C@@H]1CCN(c2cnc(C(=O)Nc3cc(Cl)n4nc(C)cc4c3)cn2)C1] | LCMS (ES+) 386.2 (M + H)+, RT 2.85 min (Analytical method AcHSSC18) $^1$H NMR (400 MHz, DMSO-d$_6$) δ 10.55 (s, 1H), 8.76 (d, J = 1.3 Hz, 1H), 8.29 (d, J = 2.1 Hz, 1H), 7.99 (d, J = 1.4 Hz, 1H), 7.66 (d, J = 2.0 Hz, 1H), 6.50 (s, 1H), 3.70-3.58 (m, 3H), 3.43-3.37 (m, 2H), 2.42 (s, 3H), 2.11 (tt, J = 6.5, 6.2 Hz, 1H), 1.97-1.85 (m, 2H). |
| 16 | 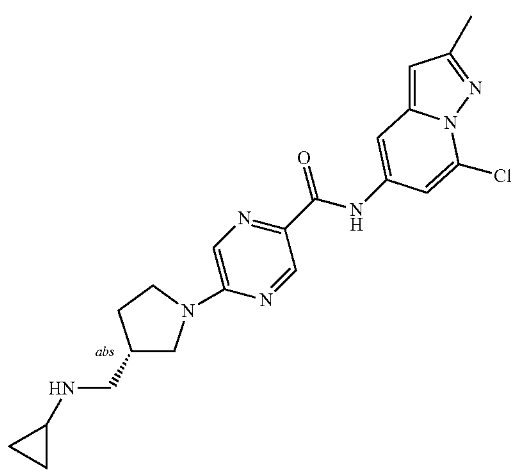 [SMILES: Cc1cc2cc(NC(=O)c3cnc(N4CC[C@@H](CNC5CC5)C4)cn3)cc(Cl)n2n1] | LCMS (ES+) 426.2 (M + H)+, RT 3.21 min (Analytical method AcHSSC18). $^1$H NMR (400 MHz, DMSO-d$_6$) δ 10.55 (s, 1H), 8.71 (d, J = 1.4 Hz, 1H), 8.27 (d, J = 2.0 Hz, 1H), 7.83 (d, J = 1.3 Hz, 1H), 7.63 (d, J = 2.1 Hz, 1H), 6.48 (s, 1H), 4.22 (dd, J = 8.3, 8.3 Hz, 2H), 3.88-3.79 (m, 2H), 2.89-2.84 (m, 3H), 2.39 (s, 3H), 2.08-2.03 (m, 1H), 0.39-0.34 (m, 2H), 0.22-0.18 (m, 2H). |

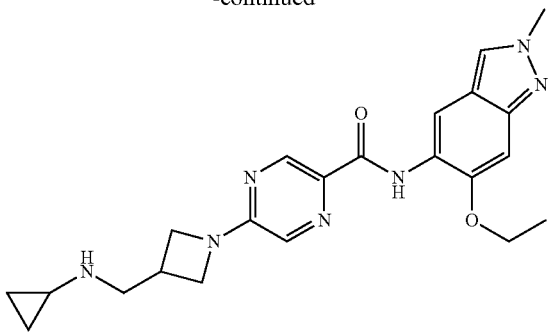

A suspension of 5-chloro-N-(6-ethoxy-2-methyl-indazol-5-yl)pyrazine-2-carboxamide (50 mg, 0.151 mmol), N-(azetidin-3-ylmethyl)cyclopropanamine dihydrochloride (39 mg, 0.196 mmol) and cesium carbonate (196 mg, 0.603 mmol) in DMF (1.50 mL) was heated at 100° C. overnight. The reaction mixture was allowed to cool to room temperature, filtered and sent to achiral reverse phase HPLC for purification (Xbridge Phenyl 19×150 mm, 10 μm 40-100% MeOH/H$_2$O (10 mM NH$_4$CO$_3$), 20 mL/min, RT) to yield 5-[3-[(cyclopropylamino)methyl]azetidin-1-yl]-N-(6-ethoxy-2-methyl-indazol-5-yl)pyrazine-2-carboxamide. LCMS (ES+) 422.4 [M+H]+, RT 2.70 min (Analytical method AcHSSC18). $^1$H NMR (400 MHz, DMSO-d$_6$) δ 10.12 (s, 1H), 8.70 (d, J=1.3 Hz, 1H), 8.65 (s, 1H), 8.20 (s, 1H), 7.88 (d, J=1.3 Hz, 1H), 7.07 (s, 1H), 4.25-4.17 (m, 4H), 4.08 (s, 3H), 3.84 (dd, J=4.8, 8.9 Hz, 2H), 2.89-2.84 (m, 3H), 2.37-2.32 (m, 1H), 2.09-2.03 (m, 1H), 1.46 (t, J=6.9 Hz, 3H), 0.39-0.34 (m, 2H), 0.22-0.17 (m, 2H).

A further analogue was prepared using the same chemistry as described in Example B, using 1-(azetidin-3-ylmethyl)-3-fluoro-azetidine dihydrochloride. Final product was isolated by Preparative HPLC.

| Ex. | Structure | Analytical data |
|---|---|---|
| 17 | 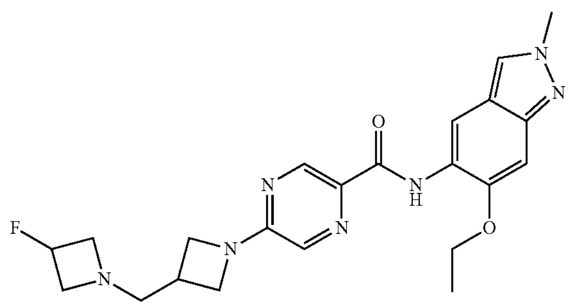 [SMILES: CCOc1cc2nn(C)cc2cc1NC(=O)c1cnc(N2CC(CN3CC(F)C3)C2)cn1] | LCMS (ES+) 440 (M + H)+, RT 4.22 min (Analytical method BicarbBEHC18). $^1$H NMR (400 MHz, DMSO-d$_6$) 11.54-11.13 (1H, m), 10.14 (1H, s), 8.73 (1H, d, J = 1.3 Hz), 8.66 (1H, s), 8.24-8.22 (1H, m), 7.92 (1H, s), 7.09-7.07 (1H, m), 5.51-5.28 (1H, m), 4.32-4.17 (5H, m), 4.09 (3H, s), 4.04-3.98 (2H, m), 3.64 (2H, s), 3.61 (2H, td, J = 6.3, 32.0 Hz), 3.13-3.03 (1H, m), 1.46 (3H, t, J = 6.9 Hz); $^{19}$F NMR (376 MHz, DMSO-d$_6$) −176.1- −176.5 (1F, m) |

A further analogue was prepared using the same chemistry as described in Example 14 using (R)-N-cyclopropylpyrrolidin-3-amine·2HCl. Final product was isolated by Preparative HPLC.

| Ex. | Structure | Analytical data |
|---|---|---|
| 18 | 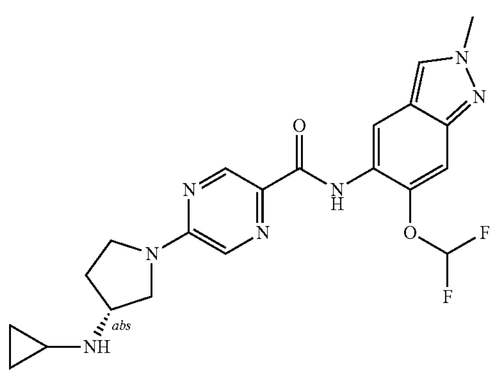 [SMILES: Cn1cc2cc(NC(=O)c3cnc(N4CC[C@@H](NC5CC5)C4)cn3)c(OC(F)F)cc2n1] | LCMS (ES+) 444.2 (M + H)+, RT 2.75 min (Analytical method AcHSSC18). $^1$H NMR (400 MHz, DMSO-d$_6$) d 9.92 (s, 1H), 8.74 (d, J = 1.1 Hz, 1H), 8.68 (s, 1H), 8.37 (s, 1H), 8.03 (d, J = 1.3 Hz, 1H), 7.46 (s, 1H), 7.40 (t, J = 73.6 Hz, 1H), 4.14 (s, 3H), 3.71-3.52 (m, 4H), 3.43-3.36 (m, 1H), 2.10 (dd, J = 3.2, 5.7 Hz, 2H), 1.95-1.91 (m, 1H), 0.40 (dd, J = 1.6, 6.7 Hz, 2H), 0.27-0.21 (m, 2H). $^{19}$F NMR (376 MHz, DMSO-d$_6$) d −81.54 (d, J = 73.8 Hz). |

Example 19: (R)-N-(8-fluoro-2-methyl-[1,2,4]tri-azolo[1,5-a]pyridin-6-yl)-5-(3-(methylamino)pyrrolidin-1-yl)pyrazine-2-carboxamide

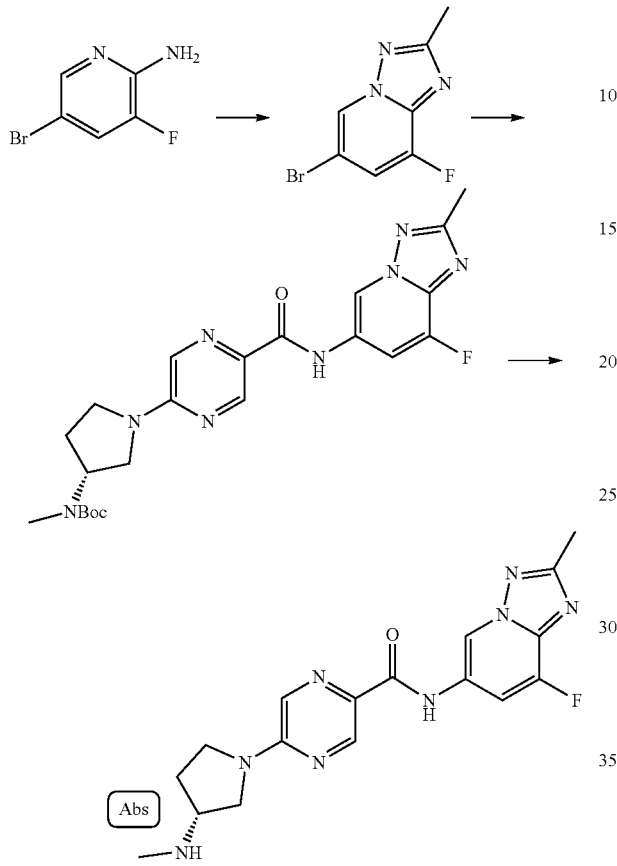

N,N-Dimethylacetamide dimethyl acetal (2.7 mL, 18.7 mmol) was added to a solution of 5-bromo-3-fluoro-pyridin-2-amine (1.02 g, 5.34 mmol) in N,N-dimethylformamide (10 mL). The reaction mixture was heated at 130° C. for 16 h. After cooling, the crude reaction mixture was concentrated in vacuo. The residue was dissolved in MeOH (15 mL), followed by the addition of pyridine (5 mL). The reaction mixture was cooled to 0° C. and hydroxylamine-O-sulfonic acid (966 mg, 8.54 mmol) was added, the ice-bath was removed, and the reaction was stirred at RT for 16 h. The reaction mixture was concentrated in vacuo and the residue was diluted with ethyl acetate and washed with aqueous sodium bicarbonate solution. The organic layer was concentrated onto silica and was purified by column chromatography eluting with ethyl acetate (0-70%) in cyclohexane. The appropriate fractions were combined and concentrated in vacuo to afford the desired product. LCMS (ES+) 230.0 (M+H)+, R.T. 1.31 min. $^1$H NMR (400 MHz, DMSO-$d_6$) d 9.25 (d, J=0.8 Hz, 1H), 7.98 (dd, J=1.5, 10.1 Hz, 1H), 2.55 (s, 3H). $^{19}$F NMR (376 MHz, DMSO-$d_6$) d −128.54 (d, J=10.1 Hz, 1F). Note: 30% starting material confirmed by NMR characterisation.

tert-Butyl N-[(3R)-1-(5-carbamoylpyrazin-2-yl)pyrrolidin-3-yl]-N-methyl-carbamate (190 mg, 0.591 mmol), 6-bromo-8-fluoro-2-methyl-[1,2,4]triazolo[1,5-a]pyridine (177 mg, 0.769 mmol), copper(I) iodide (11 mg, 0.0591 mmol), potassium carbonate (123 mg, 0.887 mmol) and N,N'-dimethylethylenediamine (0.013 mL, 0.118 mmol) in toluene (3 mL) were combined and degassed with nitrogen for 10 mins. The reaction mixture was stirred at 100° C. for 16 h. After cooling, the reaction mixture was passed through celite, diluted with ethyl acetate and washed with brine. The combined organics were concentrated onto silica and the product was purified by column chromatography eluting with cyclohexane/ethyl acetate (0-100%) gradient. The appropriate fractions were combined and concentrated in vacuo. LCMS (ES+) 471.4 (M+H)+, R.T. 1.58 min.

tert-Butyl N-[(3R)-1-[5-[(8-fluoro-2-methyl-[1,2,4]triazolo[1,5-a]pyridin-6-yl)carbamoyl]pyrazin-2-yl]pyrrolidin-3-yl]-N-methyl-carbamate (125 mg, 0.266 mmol), trifluoroacetic acid (0.66 mL, 8.64 mmol) and DCM (5 mL) were stirred at RT for 3 h. The reaction mixture was passed through an SCX cartridge, eluting with NH$_3$ in MeOH (7 M) to retrieve the product. The appropriate fraction was concentrated in vacuo to give crude product, which was purified by achiral reverse phase purification. LCMS (ES+) 371.2 (M+H)+, RT 2.18 min (Analytical method AcHSSC18). $^1$H NMR (400 MHz, DMSO-$d_6$) d 10.73 (s, 1H), 9.45 (d, J=1.6 Hz, 1H), 8.77 (d, J=1.3 Hz, 1H), 8.11 (dd, J=1.8, 12.4 Hz, 1H), 7.99 (d, J=1.3 Hz, 1H), 3.71-3.56 (m, 3H), 3.45-3.38 (m, 2H), 2.50 (s, 3H), 2.33 (s, 3H), 2.16-2.07 (m, 1H), 2.01-1.82 (m, 2H). $^{19}$F NMR (376 MHz, DMSO-$d_6$) d −130.19 (d, J=12.5 Hz, 1F).

Example 20: (R)-5-(3-((4,5-dihydro-1H-imidazol-2-yl)amino)pyrrolidin-1-yl)-N-(8-fluoro-2-methylimidazo[1,2-a]pyridin-6-yl)pyrazine-2-carboxamide

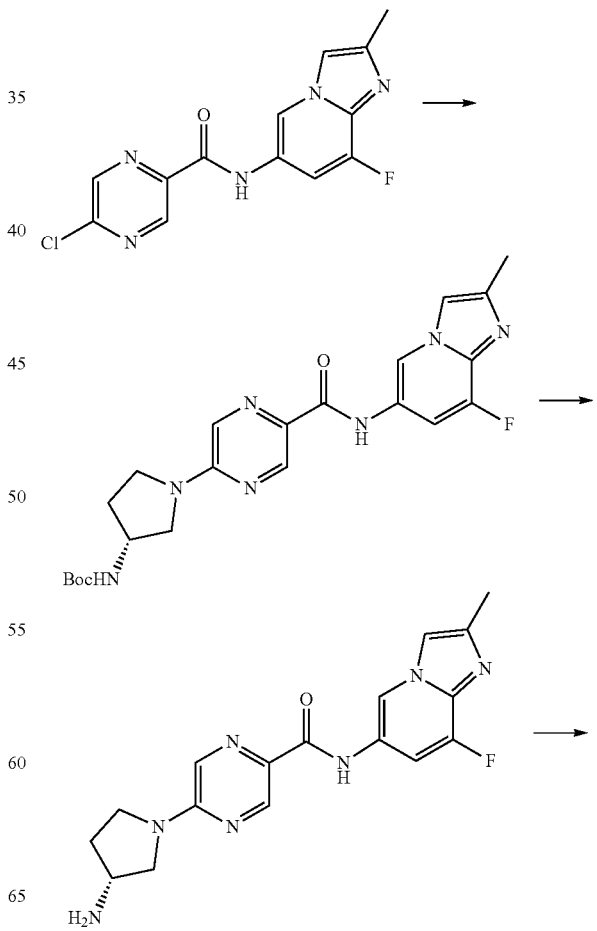

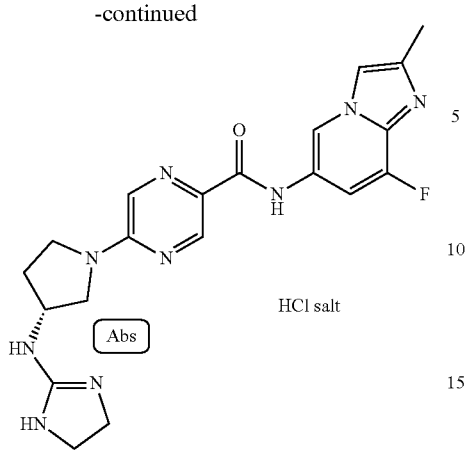

(R)-3-(Boc-amino)pyrrolidine (96 mg, 0.517 mmol), triethylamine (0.22 mL, 1.55 mmol), and 5-chloro-N-(8-fluoro-2-methyl-imidazo[1,2-a]pyridin-6-yl)pyrazine-2-carboxamide (158 mg, 0.517 mmol) were combined in MeCN (6 mL) and stirred at 65° C. for 1 h. The reaction was stopped and concentrated in vacuo, dissolved in DCM and washed with brine. The organic layer was concentrated in vacuo to give the desired product. LCMS (ES+) 456.5 (M+H)+, R.T. 1.49 min.

tert-Butyl N-[(3R)-1-[5-[(8-fluoro-2-methyl-imidazo[1,2-a]pyridin-6-yl)carbamoyl]pyrazin-2-yl]pyrrolidin-3-yl]carbamate (280 mg, 0.615 mmol), TFA (1.5 mL, 20.0 mmol) and DCM (5 mL) were stirred at RT for 3 h. The reaction mixture was passed through an SCX cartridge, eluting with $NH_3$ in MeOH (7 M) to retrieve the product. The appropriate fraction was concentrated in vacuo to give the desired product. LCMS (ES+) 356 (M+H)+, R.T. 1.10 min.

5-[(3R)-3-aminopyrrolidin-1-yl]-N-(8-fluoro-2-methyl-imidazo[1,2-a]pyridin-6-yl)pyrazine-2-carboxamide (67 mg, 0.189 mmol), 4,5-dihydro-1H-imidazole-2-sulfonic acid (37 mg, 0.245 mmol) and were combined in 1-butanol (5 mL). The reaction was stirred for 2 h at RT, the reaction mixture was concentrated in vacuo and submitted for achiral SFC to give the desired product. LCMS (ES+) 423 (M+H)+, R.T. 1.18 min.

5-[(3R)-3-(4,5-dihydro-1H-imidazol-2-ylamino)pyrrolidin-1-yl]-N-(8-fluoro-2-methyl-imidazo[1,2-a]pyridin-6-yl)pyrazine-2-carboxamide (18 mg, 0.0434 mmol) and HCl (0.011 mL, 0.0434 mmol, 4 M) in MeOH (1 mL) were stirred at RT for 3 h. The reaction was stopped, and nitrogen was passed through the sample for 2 h. The compound was dried further in the high vacuum oven for 24 h to give the desired HCl salt product. LCMS (ES+) 424.2 (M+H)+, RT 1.82 min (Analytical method AcHSSC18). $^1$H NMR (400 MHz, DMSO-$d_6$) δ 10.48 (s, 1H), 9.20 (s, 1H), 8.81-8.77 (m, 2H), 8.05 (s, 1H), 7.92 (d, J=2.6 Hz, 1H), 7.60 (d, J=12.5 Hz, 1H), 4.32-4.26 (m, 1H), 3.85 (dd, J=5.6, 11.5 Hz, 1H), 3.70 (t, J=7.0 Hz, 2H), 3.64 (s, 3H), 3.60 (dd, J=3.8, 11.9 Hz, 1H), 2.36-2.29 (m, 3H), 2.12-2.06 (m, 1H). $^{19}$F NMR (376 MHz, DMSO-$d_6$) δ -132.11 (dd, J=3.0, 12.4 Hz, 1F).

Example 21: (R)-N-(8-fluoro-2,7-dimethylimidazo[1,2-a]pyridin-6-yl)-5-(3-(methylamino)pyrrolidin-1-yl)pyrazine-2-carboxamide

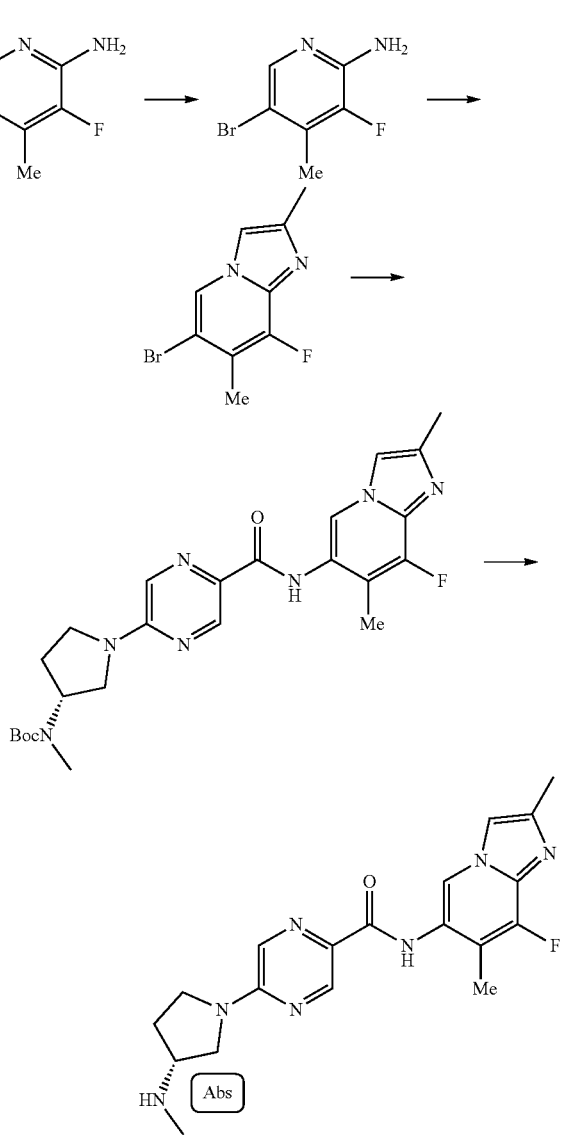

3-Fluoro-4-methyl-pyridin-2-amine (348 mg, 2.76 mmol) and N-bromosuccinimide (491 mg, 2.76 mmol) in DCM (20 mL) were stirred at RT for 1 h. The reaction mixture was concentrated in vacuo and ethyl acetate was added to the residue and the precipitant was isolated from the filtrate to give the desired product. $^1$H NMR (400 MHz, DMSO-$d_6$) δ 7.90 (s, 1H), 6.40-6.33 (m, 2H), 2.26 (d, J=2.5 Hz, 3H). $^{19}$F NMR (376 MHz, DMSO-$d_6$) δ -138.44 (s, 1F).

5-Bromo-3-fluoro-4-methyl-pyridin-2-amine (500 mg, 2.44 mmol), 1-bromo-2,2-dimethoxypropane (0.49 mL, 3.66 mmol), pyridinium p-toluenesulfonate (61 mg, 0.244 mmol), and 2-propanol (15 mL) were combined in a sealed tube and hot block heated to 85° C. The precipitant was collected via vacuum filtration to give the desired product. $^1$H NMR (400 MHz, DMSO-$d_6$) δ 9.09 (s, 1H), 7.98 (s, 1H), 2.49 (d, J=0.7 Hz, 3H), 2.46 (d, J=3.0 Hz, 3H). $^{19}$F NMR (376 MHz, DMSO-$d_6$) δ -132.66 (s, 1F).

tert-Butyl N-[(3R)-1-(5-carbamoylpyrazin-2-yl)pyrrolidin-3-yl]-N-methyl-carbamate (111 mg, 0.345 mmol), 6-bromo-8-fluoro-2,7-dimethyl-imidazo[1,2-a]pyridine (109 mg, 0.449 mmol) copper(I) iodide (6.6 mg, 0.0345 mmol), potassium carbonate (72 mg, 0.518 mmol), N,N'-dimethylethylenediamine (0.0074 mL, 0.0691 mmol), and toluene (3 mL) were combined and the reaction mixture was degassed with nitrogen for 10 mins and stirred at 100° C. for 24 h. The reaction mixture was diluted with water and washed with EtOAc (×3). The combined organics were concentrated onto silica and the product was purified by column chromatography eluting with cyclohexane/ethyl acetate (0-90%) gradient. The appropriate fractions were combined and concentrated in vacuo to give the product. LCMS (ES+) 484.4 (M+H)+, R.T. 1.56 min.

tert-Butyl-N-[(3R)-1-[5-[(8-fluoro-2,7-dimethyl-imidazo[1,2-a]pyridin-6-yl)carbamoyl]pyrazin-2-yl]pyrrolidin-3-yl]-N-methyl-carbamate (86 mg, 0.178 mmol), DCM (5 mL), and TFA (34 mg, 0.534 mmol) were stirred at RT for 1 h. The reaction was stopped and passed through an SCX cartridge, eluting with NH$_3$ (7 M) in MeOH. The appropriate fraction was concentrated in vacuo to give crude product which was purified by achiral purification to give the desired compound. LCMS (ES+) 384.2 (M+H)+, RT 1.91 min (Analytical method AcHSSC18). $^1$H NMR (400 MHz, DMSO-d$_6$) δ 9.89 (s, 1H), 8.72 (d, J=1.3 Hz, 1H), 8.68 (s, 1H), 8.03 (d, J=1.4 Hz, 1H), 7.78 (d, J=2.8 Hz, 1H), 3.70-3.57 (m, 3H), 3.40 (d, J=10.4 Hz, 1H), 2.35 (d, J=0.8 Hz, 3H), 2.32 (s, 3H), 2.22 (d, J=2.5 Hz, 3H), 2.14-2.07 (m, 1H), 1.96-1.86 (m, 2H). $^{19}$F NMR (376 MHz, DMSO-d$_6$) δ -136.76 (s, 1F).

Example 22: (R)-N-(4-methoxy-2-methylbenzo[d]oxazol-6-yl)-5-(3-(methylamino)pyrrolidin-1-yl)pyrazine-2-carboxamide

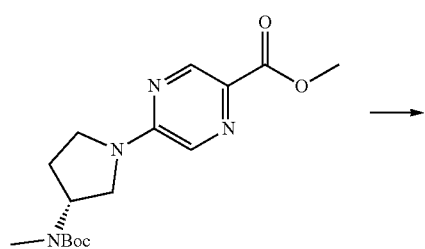

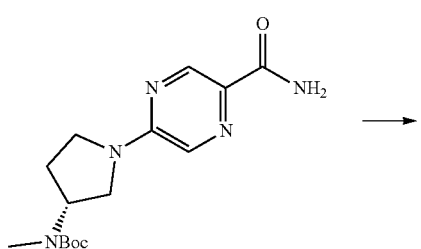

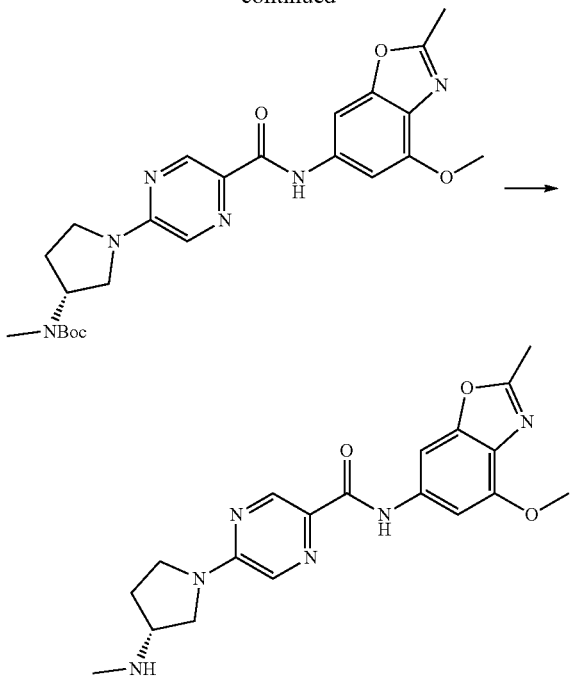

Methyl 5-[(3R)-3-[tert-butoxycarbonyl(methyl)amino]pyrrolidin-1-yl]pyrazine-2-carboxylate (1.50 g, 4.46 mmol) was dissolved in methanol (5 mL) and treated with ammonia (7 M in methanol, 34 mL, 0.237 mol). The reaction mixture was sealed in a tube and stirred at 80° C. for 3 days. After cooling to r.t., the reaction was concentrated in vacuo to give crude tert-butyl N-[(3R)-1-(5-carbamoylpyrazin-2-yl)pyrrolidin-3-yl]-N-methyl-carbamate, which was used without further purification.

tert-Butyl N-[(3R)-1-(5-carbamoylpyrazin-2-yl)pyrrolidin-3-yl]-N-methyl-carbamate (106 mg, 0.330 mmol), 6-bromo-4-methoxy-2-methyl-1,3-benzoxazole (107 mg, 0.442 mmol), copper(I) iodide (12 mg, 0.0604 mmol), potassium carbonate (66 mg, 0.478 mmol), and N,N'-dimethylethylenediamine (0.013 mL, 0.119 mmol) were suspended in toluene (3 mL) and sparged with N$_2$ for 10 min. The mixture was sealed in a tube and stirred at 100° C. for 4 days. After cooling to r.t., the mixture was diluted with 20 mL water and extracted with 3×30 mL EtOAc; the combined organics were washed with 20 mL brine, dried (Na$_2$SO$_4$) and concentrated. The residue was purified by SFC to give crude tert-butyl N-[(3R)-1-[5-[(4-methoxy-2-methyl-1,3-benzoxazol-6-yl)carbamoyl]pyrazin-2-yl]pyrrolidin-3-yl]-N-methyl-carbamate, which was used without further purification.

tert-Butyl N-[(3R)-1-[5-[(4-methoxy-2-methyl-1,3-benzoxazol-6-yl)carbamoyl]pyrazin-2-yl]pyrrolidin-3-yl]-N-methyl-carbamate (22 mg, 0.0456 mmol) was dissolved in dichloromethane (1.5 mL) at r.t. Trifluoroacetic acid (0.47 mL, 6.14 mmol) was added. After stirring at r.t. for 15 min the majority of TFA was removed by evaporation at reduced pressure and the residue was dissolved in 5 ml MeOH.

0.97 g MP-carbonate beads were added (3 mmol/g). The mixture was stirred at r.t. for 20 min, then filtered and concentrated. The residue was combined with another, smaller (one-half scale) experiment and purified by SFC to give (R)-N-(4-methoxy-2-methylbenzo[d]oxazol-6-yl)-5-(3-(methylamino)pyrrolidin-1-yl)pyrazine-2-carboxamide. LCMS (ES+) 383.2 (M+H)+, RT 2.53 min (Analytical method AcHSSC18); $^1$H NMR (400 MHz, DMSO-$d_6$) δ 10.31 (s, 1H), 8.74 (d, J=1.3 Hz, 1H), 7.97-7.95 (m, 2H), 7.49 (d, J=1.5 Hz, 1H), 3.94 (s, 3H), 3.68-3.57 (m, 3H), 3.40-3.35 (m, 1H), 2.55 (s, 3H), 2.31 (s, 3H), 2.14-2.05 (m, 1H), 1.94-1.82 (m, 2H). One NH not observed.

Example 23: 5-(6-(ethylamino)-3-azabicyclo[3.1.0]hexan-3-yl)-N-(8-fluoro-2-methylimidazo[1,2-a]pyridin-6-yl)pyrazine-2-carboxamide

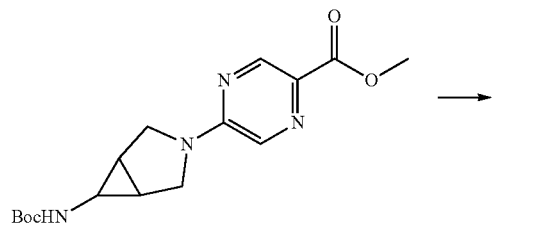

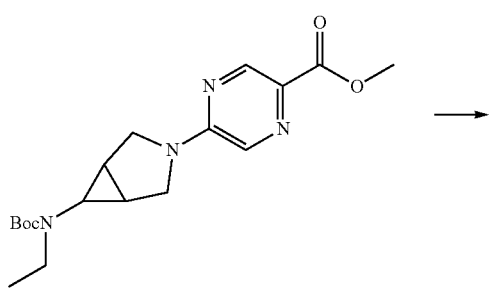

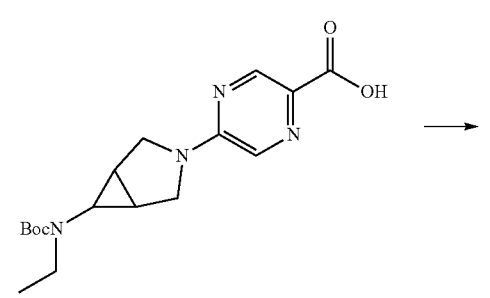

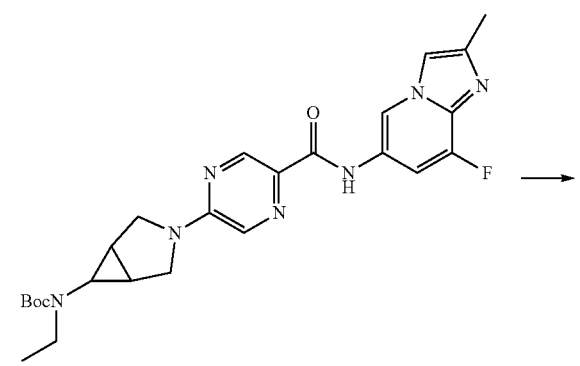

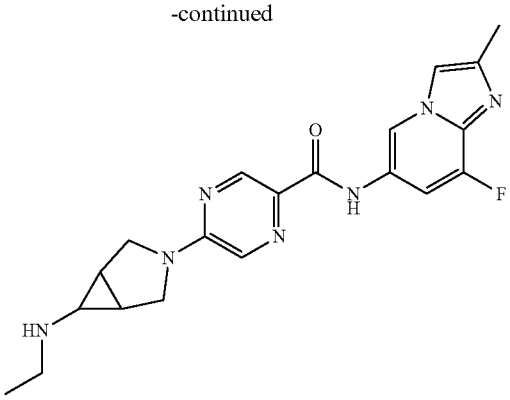

Methyl 5-[6-(tert-butoxycarbonylamino)-3-azabicyclo[3.1.0]hexan-3-yl]pyrazine-2-carboxylate (375 mg, 1.12 mmol, 1.00 eq), sodium hydride (60%, 54 mg, 1.35 mmol, 1.20 eq), N,N-dimethylformamide (10 mL), and iodoethane (0.11 mL, 1.35 mmol, 1.20 eq) were combined under a nitrogen atmosphere and stirred at room temperature overnight. The mixture was diluted with EtOAc, washed with water (3×), and concentrated in vacuo to give methyl 5-[6-[tert-butoxycarbonyl(ethyl)amino]-3-azabicyclo[3.1.0]hexan-3-yl]pyrazine-2-carboxylate, which was used directly in next step. LCMS (ES+) 363 (M+H)+.

Methyl 5-[6-[tert-butoxycarbonyl(ethyl)amino]-3-azabicyclo[3.1.0]hexan-3-yl]pyrazine-2-carboxylate (crude from previous step, 1.12 mmol, 1.00 eq), Lithium hydroxide monohydrate (56 mg, 1.35 mmol, 1.20 eq), methyl alcohol (30 mL) and water (3 mL) were combined and hot block heated to 50° C. overnight. The mixture was concentrated in vacuo to remove MeOH and partitioned between EtOAc and water/AcOH. The organics were dried (MgSO$_4$) and concentrated in vacuo and dried in vac oven to give 5-[6-[tert-butoxycarbonyl(ethyl)amino]-3-azabicyclo[3.1.0]hexan-3-yl]pyrazine-2-carboxylic acid, which was used directly in next step. LCMS (ES+) 349 (M+H)+.

5-[6-[tert-Butoxycarbonyl(ethyl)amino]-3-azabicyclo[3.1.0]hexan-3-yl]pyrazine-2-carboxylic acid (95 mg, 0.273 mmol, 1.00 eq), 8-fluoro-2-methyl-imidazo[1,2-a]pyridin-6-amine (45 mg, 0.273 mmol, 1.00 eq), HBTU (103 mg, 0.273 mmol, 1.00 eq), N,N-dimethylformamide (2 mL), and triethylamine (0.50 mL, 3.59 mmol, 13.2 eq) were combined and stirred at room temperature for 3 h. Reaction mixture was then purified by prep HPLC to give tert-butyl N-ethyl-N-[3-[5-[(8-fluoro-2-methyl-imidazo[1,2-a]pyridin-6-yl)carbamoyl]pyrazin-2-yl]-3-azabicyclo[3.1.0]hexan-6-yl]carbamate, which was used directly in next step. LCMS (ES+) 496 (M+H)+.

tert-Butyl N-ethyl-N-[3-[5-[(8-fluoro-2-methyl-imidazo[1,2-a]pyridin-6-yl)carbamoyl]pyrazin-2-yl]-3-azabicyclo[3.1.0]hexan-6-yl]carbamate (81 mg, 0.163 mmol, 1.00 eq), methyl alcohol (2 mL) and 4 M hydrogen chloride in dioxane (2.0 mL, 8.00 mmol, 48.9 eq) were combined and stirred at room temperature for 2 h. The mixture was concentrated in vacuo and purified by prep HPLC to give the title compound. LCMS (ES+) 396.2 (M+H)+, RT 1.8 min (Analytical method AcHSSC18). $^1$H NMR (400 MHz, DMSO-$d_6$) d 10.43 (s, 1H), 9.19 (d, J=1.6 Hz, 1H), 8.74 (d, J=1.1 Hz, 1H), 7.94 (d, J=1.4 Hz, 1H), 7.89 (d, J=2.8 Hz, 1H), 7.56 (dd, J=1.6, 13.1 Hz, 1H), 3.78 (d, J=11.2 Hz, 2H), 3.64-3.57 (m, 2H), 2.61 (q, J=7.2 Hz, 2H), 2.35 (s, 3H), 2.19 (s, 1H), 1.90 (dd, J=2.2, 2.2 Hz, 1H), 1.72 (s, 2H), 1.02 (dd, Example 24: 5-(6-amino-3-azabicyclo[3.1.0]hexan-3-yl)-N-(8-fluoro-2-methyl-imidazo[1,2-a]pyridin-6-yl)pyrazine-2-carboxamide

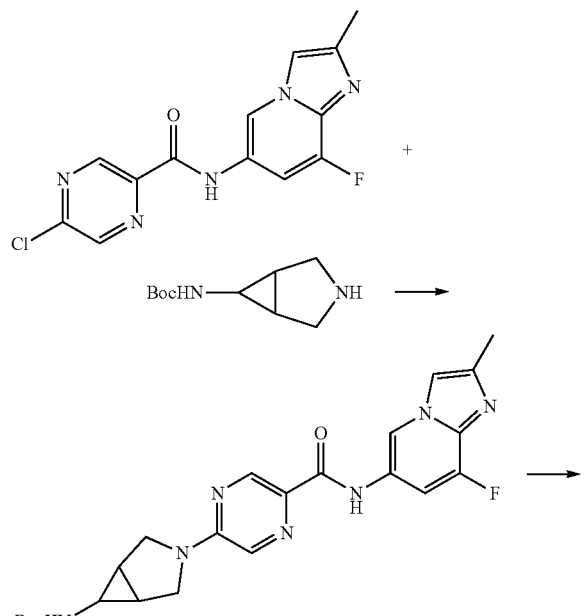

5-Chloro-N-(8-fluoro-2-methyl-imidazo[1,2-a]pyridin-6-yl)pyrazine-2-carboxamide (120 mg, 0.393 mmol, 1.00 eq), 6-(Boc-amino)-3-azabicyclo[3.1.0]hexane (198211-38-0) (78 mg, 0.393 mmol, 1.00 eq), cesium carbonate (192 mg, 0.589 mmol, 1.50 eq), and N,N-dimethylformamide (3 mL) were combined in a sealed tube and hot block heated to 100° C. for 1 hour. The reaction was cooled to room temperature and filtered to remove cesium salts. The crude was purified by prep HPLC to give tert-butyl N-[3-[5-[(8-fluoro-2-methyl-imidazo[1,2-a]pyridin-6-yl)carbamoyl]pyrazin-2-yl]-3-azabicyclo[3.1.0]hexan-6-yl]carbamate. LCMS (ES+) 468 (M+H)+. $^1$H NMR (400 MHz, DMSO-$d_6$) d 10.43 (s, 1H), 9.19 (d, J=1.5 Hz, 1H), 8.75 (d, J=1.1 Hz, 1H), 7.98 (d, J=1.3 Hz, 1H), 7.90 (d, J=2.8 Hz, 1H), 7.56 (dd, J=1.6, 13.1 Hz, 1H), 7.21-7.17 (m, 1H), 3.84 (d, J=11.2 Hz, 2H), 3.63 (d, J=11.0 Hz, 2H), 2.35 (s, 3H), 2.28-2.25 (m, 1H), 1.87 (s, 2H), 1.41 (s, 9H).

tert-Butyl N-[3-[5-[(8-fluoro-2-methyl-imidazo[1,2-a]pyridin-6-yl)carbamoyl]pyrazin-2-yl]-3-azabicyclo[3.1.0]hexan-6-yl]carbamate (100 mg, 0.214 mmol, 1.00 eq), methyl alcohol (2 mL), and 4 M hydrogen chloride in dioxane (2.0 mL, 8.00 mmol, 37.4 eq) were combined and stirred at room temperature for 1 h. Reaction mixture was concentrated in vacuo and purified by prep HPLC to give 5-(6-amino-3-azabicyclo[3.1.0]hexan-3-yl)-N-(8-fluoro-2-methyl-imidazo[1,2-a]pyridin-6-yl)pyrazine-2-carboxamide. LCMS (ES+) 368.2 (M+H)+, RT 1.98 min (Analytical method AcHSSC18). $^1$H NMR (400 MHz, DMSO-$d_6$) d 10.42 (s, 1H), 9.19 (d, J=1.6 Hz, 1H), 8.73 (d, J=1.1 Hz, 1H), 7.93 (d, J=1.3 Hz, 1H), 7.89 (d, J=2.8 Hz, 1H), 7.56 (dd, J=1.7, 13.0 Hz, 1H), 3.75 (d, J=11.2 Hz, 2H), 3.63-3.56 (m, 2H), 2.35 (s, 3H), 2.02 (dd, J=2.1, 2.1 Hz, 1H), 1.98 (s, 1H), 1.66 (s, 2H).

The following compounds were synthesised in a similar manner from the appropriate starting materials.

| Ex. | Product | Starting material | Analytical data |
|---|---|---|---|
| 25 | (structure) | (structure) | LCMS (ES+) 365.2 (M + H)+, RT 1.9 min (Analytical method AcHSSC18). $^1$H NMR (400 MHz, DMSO-$d_6$) d 9.66 (s, 1H), 9.14 (s, 1H), 8.74 (d, J = 1.3 Hz, 1H), 8.01-7.98 (m, 2H), 3.75 (d, J = 11.3 Hz, 2H), 3.60 (d, J = 11.4 Hz, 2H), 2.71 (s, 3H), 2.40 (s, 3H), 2.01 (s, 2H), 1.68-1.67 (m, 2H). |

| Ex. | Product | Starting material | Analytical data |
|---|---|---|---|
| 26 | (pyrazine-carboxamide with 3-(6-amino-3-azabicyclo[3.1.0]hexan-3-yl) substituent, N-linked to 8-methoxy-2-methylimidazo[1,2-a]pyrazine) | Boc-NH-(3-azabicyclo[3.1.0]hexan-6-yl) | LCMS (ES+) 381 (M + H)+, RT 1.96 min (Analytical method AcHSSC18). ¹H NMR (400 MHz, DMSO-d₆) d 9.87 (s, 1H), 9.16 (s, 1H), 8.82 (d, J = 1.5 Hz, 1H), 8.28 (s, 1H), 8.10 (d, J = 1.3 Hz, 1H), 4.21 (s, 3H), 3.91 (d, J = 11.4 Hz, 2H), 3.75-3.69 (m, 3H), 3.56-3.48 (m, 1H), 2.49 (s, 4H), 2.28 (s, 2H). |
| 27 | (pyrazine-carboxamide with 3-(6-amino-3-azabicyclo[3.1.0]hexan-3-yl) substituent, N-linked to 7-fluoro-2,8-dimethylimidazo[1,2-a]pyridine) | Boc-NH-(3-azabicyclo[3.1.0]hexan-6-yl) | LCMS (ES+) 382.2 (M + H)+, RT 1.82 min (Analytical method AcHSSC18). ¹H NMR (400 MHz, DMSO-d₆) d 9.80 (s, 1H), 8.97 (d, J = 7.3 Hz, 1H), 8.72 (d, J = 1.3 Hz, 1H), 8.00 (d, J = 1.3 Hz, 1H), 7.72 (s, 1H), 3.75 (d, J = 11.3 Hz, 2H), 3.60 (dd, J = 2.3, 8.8 Hz, 2H), 2.40 (d, J = 1.9 Hz, 3H), 2.33 (s, 3H), 2.01 (dd, J = 2.2, 2.2 Hz, 2H), 1.66 (s, 2H). ¹⁹F NMR (376 MHz, DMSO-d₆) d −133.05 |
| 28 | (pyrazine-carboxamide with 3-(1-amino-3-azabicyclo[3.1.0]hexan-3-yl) substituent, N-linked to 8-fluoro-2-methylimidazo[1,2-a]pyridine) Enantiomer 1 + Enantiomer 2 | (1-amino-3-azabicyclo[3.1.0]hexane) | LCMS (ES+) 368 (M + H)+, RT 1.73 min (Analytical method AcHSSC18). ¹H NMR (400 MHz, DMSO-d₆) d 10.43 (s, 1H), 9.19 (d, J = 1.6 Hz, 1H), 8.73 (d, J = 1.3 Hz, 1H), 7.95 (d, J = 1.0 Hz, 1H), 7.89 (d, J = 2.8 Hz, 1H), 7.56 (dd, J = 1.8, 13.1 Hz, 1H), 3.94 (d, J = 10.4 Hz, 1H), 3.69 (s, 2H), 3.47 (d, J = 10.5 Hz, 1H), 2.35 (s, 3H), 2.28 (s, 2H), 1.54-1.48 (m, 1H), 0.97 (dd, J = 5.0, 7.7 Hz, 1H), 0.46 (dd, J = 4.5, 4.5 Hz, 1H). ¹⁹F NMR (376 MHz, DMSO-d₆) d −132.17 (dd, J = 2.7 Hz, J = 13.4 Hz). |

Example 29: N-(8-Fluoro-2-methyl-imidazo[1,2-a]pyridin-6-yl)-5-[6-(methylamino)-3-azabicyclo[3.1.0]hexan-3-yl]pyrazine-2-carboxamide

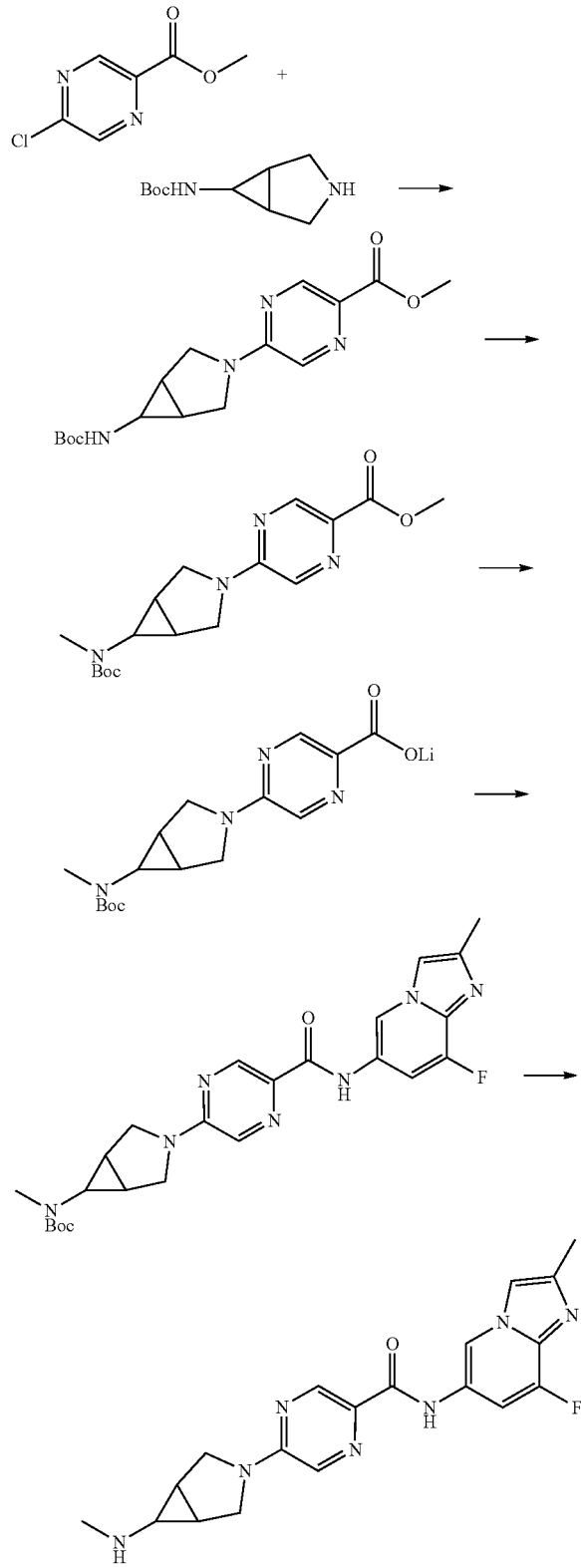

Methyl 5-chloro-2-pyrazinecarboxylate (223 mg, 1.29 mmol, 1.00 eq), 6-(Boc-amino)-3-azabicyclo[3.1.0]hexane (256 mg, 1.29 mmol, 1.00 eq) (Cas no. 198211-38-0), cesium carbonate (631 mg, 1.94 mmol, 1.50 eq), and acetonitrile (15 mL) were combined in a sealed tube and hot block heated to 80° C. for 4 h. Reaction mixture was cooled to room temperature and concentrated in vacuo onto silica gel and purified by flash chromatography to give methyl 5-[6-(tert-butoxycarbonylamino)-3-azabicyclo[3.1.0]hexan-3-yl]pyrazine-2-carboxylate. LCMS (ES+) 335 (M+H)+.

Methyl 5-[6-(tert-butoxycarbonylamino)-3-azabicyclo[3.1.0]hexan-3-yl]pyrazine-2-carboxylate (119 mg, 0.356 mmol, 1.00 eq), sodium hydride (60%, 17 mg, 0.427 mmol, 1.20 eq), N,N-dimethylformamide (3 mL), and iodomethane (0.044 mL, 0.712 mmol, 2.00 eq) were combined under a nitrogen atmosphere and stirred at room temperature over a weekend. Reaction mixture was diluted with EtOAc, washed with water, concentrated in vacuo to give methyl 5-[6-[tert-butoxycarbonyl(methyl)amino]-3-azabicyclo[3.1.0]hexan-3-yl]pyrazine-2-carboxylate, which was used directly in next step. LCMS (ES+) 349 (M+H)+.

Methyl 5-[6-[tert-butoxycarbonyl(methyl)amino]-3-azabicyclo[3.1.0]hexan-3-yl]pyrazine-2-carboxylate (124 mg, 0.355 mmol, 1.00 eq), lithium hydroxide monohydrate (18 mg, 0.426 mmol, 1.20 eq), methyl alcohol (10 mL), and water (1 mL) were combined and hot block heated to 50° C. for 2 days. Reaction mixture was concentrated in vacuo to give [5-[6-[tert-butoxycarbonyl(methyl)amino]-3-azabicyclo[3.1.0]hexan-3-yl]pyrazine-2-carbonyl]oxylithium, which was used directly in next step. LCMS (ES+) 335 (M+H)+ for acid.

5-[6-[tert-Butoxycarbonyl(methyl)amino]-3-azabicyclo[3.1.0]hexan-3-yl]pyrazine-2-carboxylic acid (45 mg, 0.135 mmol, 1.00 eq), 8-fluoro-2-methyl-imidazo[1,2-a]pyridin-6-amine (22 mg, 0.135 mmol, 1.00 eq), HBTU (51 mg, 0.135 mmol, 1.00 eq), N,N-dimethylformamide (1 mL), and triethylamine (0.25 mL, 1.79 mmol, 13.3 eq) were combined and stirred at room temperature for 1 h.

Reaction mixture was purified by prep HPLC to give tert-butyl N-[3-[5-[(8-fluoro-2-methyl-imidazo[1,2-a]pyridin-6-yl)carbamoyl]pyrazin-2-yl]-3-azabicyclo[3.1.0]hexan-6-yl]-N-methyl-carbamate. LCMS (ES+) 482 (M+H)+.

tert-Butyl N-[3-[5-[(8-fluoro-2-methyl-imidazo[1,2-a]pyridin-6-yl)carbamoyl]pyrazin-2-yl]-3-azabicyclo[3.1.0]hexan-6-yl]-N-methyl-carbamate (49 mg, 0.102 mmol, 1.00 eq), methyl alcohol (1 mL), and 4 M hydrogen chloride in dioxane (1.0 mL, 4.00 mmol, 39.3 eq) were combined and stirred at room temperature for 2 h. Reaction mixture was then concentrated in vacuo and purified by prep HPLC to give the title compound. LCMS (ES+) 382.2 (M+H)+, RT 1.74 min (Analytical method AcHSSC18). $^1$H NMR (400 MHz, DMSO-$d_6$) d 10.43 (s, 1H), 9.19 (d, J=1.6 Hz, 1H), 8.74 (d, J=1.3 Hz, 1H), 7.95 (d, J=1.3 Hz, 1H), 7.89 (d, J=2.8 Hz, 1H), 7.56 (dd, J=1.9, 13.1 Hz, 1H), 3.77 (d, J=11.2 Hz, 2H), 3.64-3.57 (m, 2H), 2.35 (d, J=1.1 Hz, 3H), 2.32 (s, 3H), 2.21 (s, 1H), 1.85 (dd, J=2.1, 2.1 Hz, 1H), 1.72 (s, 2H). $^{19}$F NMR (376 MHz, DMSO-$d_6$) d −132.18 (dd, J=3 Hz, J=13.6 Hz).

Example 30: 5-(6-Amino-3-azabicyclo[3.1.0]hexan-3-yl)-N-(6-methoxy-2-methyl-indazol-5-yl)pyrazine-2-carboxamide

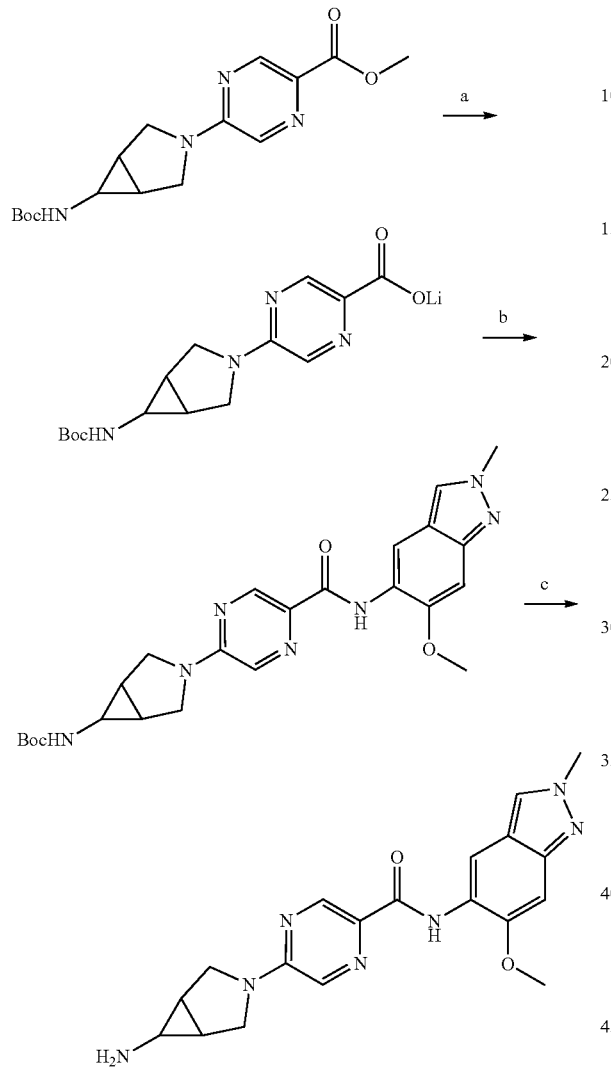

Methyl 5-[6-(tert-butoxycarbonylamino)-3-azabicyclo[3.1.0]hexan-3-yl]pyrazine-2-carboxylate (223 mg, 0.667 mmol, 1.00 eq), lithium hydroxide monohydrate (34 mg, 0.800 mmol, 1.20 eq), methyl alcohol (20 mL), and water (2 mL) were combined and hot block heated to 55° C. overnight. Reaction mixture was concentrated in vacuo to give [5-[6-(tert-butoxycarbonylamino)-3-azabicyclo[3.1.0]hexan-3-yl]pyrazine-2-carbonyl]oxylithium, which was used directly in next step. LCMS (ES+) 321 (M+H)+ for acid.

[5-[6-(tert-Butoxycarbonylamino)-3-azabicyclo[3.1.0]hexan-3-yl]pyrazine-2-carbonyl]oxylithium (104 mg, 0.319 mmol, 1.00 eq), 6-methoxy-2-methyl-indazol-5-amine (56 mg, 0.319 mmol, 1.00 eq), HBTU (121 mg, 0.319 mmol, 1.00 eq), N,N-dimethylformamide (2 mL), and triethylamine (0.50 mL, 3.59 mmol, 11.3 eq) were combined and stirred at room temperature for 2 h. The reaction mixture was concentrated in vacuo, triturated with water, filtered off, and dried in a vac oven to give tert-butyl N-[3-[5-[(6-methoxy-2-methyl-indazol-5-yl)carbamoyl]pyrazin-2-yl]-3-azabicyclo[3.1.0]hexan-6-yl]carbamate, which was used directly in next step. LCMS (ES+) 480 (M+H)+.

tert-Butyl N-[3-[5-[(6-methoxy-2-methyl-indazol-5-yl)carbamoyl]pyrazin-2-yl]-3-azabicyclo[3.1.0]hexan-6-yl]carbamate (111 mg, 0.231 mmol, 1.00 eq), methyl alcohol (2 mL), and 4 M hydrogen chloride in dioxane (2.0 mL, 8.00 mmol, 34.6 eq) were combined and stirred at room temperature for 1 h. The reaction mixture was concentrated in vacuo. Water was added, and the resulting precipitate was filtered, rinsed with water, and dried in a vac oven to give the title compound. LCMS (ES+) 380.2 (M+H)+, RT 2.43 min (Analytical method AcHSSC18). $^1$H NMR (400 MHz, DMSO-$d_6$) d 10.05 (s, 1H), 8.74 (d, J=1.0 Hz, 1H), 8.68 (s, 1H), 8.23 (s, 1H), 8.02 (d, J=1.3 Hz, 1H), 7.11 (s, 1H), 4.10 (s, 3H), 3.98 (s, 3H), 3.74 (d, J=11.2 Hz, 2H), 3.59 (dd, J=2.3, 9.0 Hz, 2H), 2.09-2.08 (m, 2H), 2.01 (dd, J=2.2, 2.2 Hz, 1H), 1.66 (s, 2H).

Example 31: 5-[(3R)-3-[(cyclopropylamino)methyl]pyrrolidin-1-yl]-N-(7-fluoro-2,8-dimethyl-imidazo[1,2-a]pyridin-6-yl)pyrazine-2-carboxamide

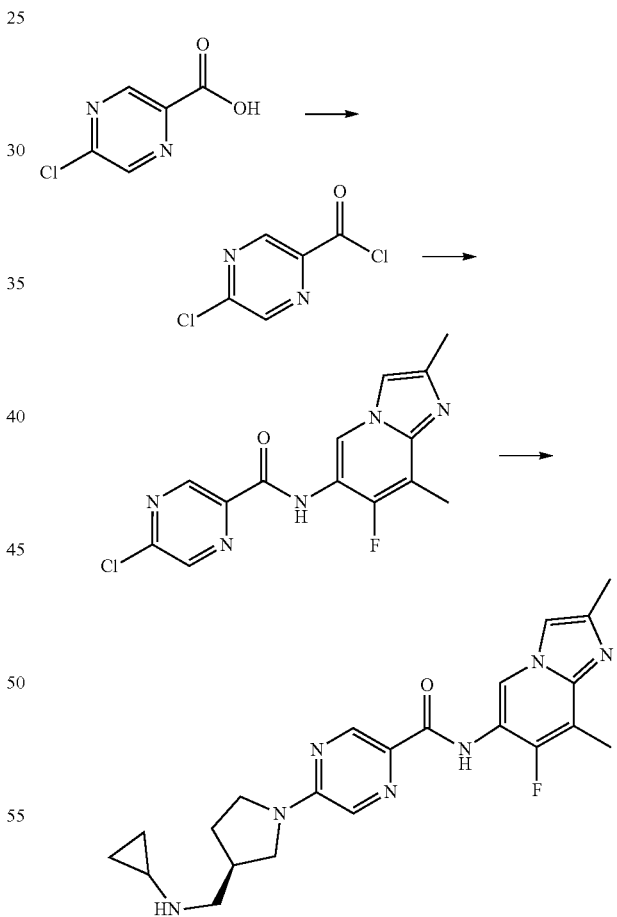

5-Chloro-2-pyrazinecarboxylic acid (159 mg, 1.00 mmol, 1.00 eq), dichloromethane (5 mL), oxalyl chloride, GMP (0.17 mL, 2.00 mmol, 2.00 eq), and 1 drop of DMF were combined and stirred at room temperature under a nitrogen atmosphere overnight. Reaction mixture was then concentrated in vacuo to give 5-chloropyrazine-2-carbonyl chloride, which was used directly in next step.

5-Chloropyrazine-2-carbonyl chloride (177 mg, 1.00 mmol, 1.00 eq), 7-fluoro-2,8-dimethyl-imidazo[1,2-a]pyridin-6-amine (197 mg, 1.10 mmol, 1.10 eq), dichloromethane (10 mL), and triethylamine (0.50 mL, 3.59 mmol, 3.59 eq) were combined and stirred at room temperature for 30 minutes. Reaction mixture was then concentrated in vacuo to give 5-chloro-N-(7-fluoro-2,8-dimethyl-imidazo[1,2-a]pyridin-6-yl)pyrazine-2-carboxamide, which was used directly in next step. LCMS (ES+) 320/322 (M+H)+.

5-Chloro-N-(7-fluoro-2,8-dimethyl-imidazo[1,2-a]pyridin-6-yl)pyrazine-2-carboxamide (250 mg, 0.782 mmol, 1.00 eq), N-[[(3S)-pyrrolidin-3-yl]methyl]cyclopropanamine (195 mg, 1.39 mmol, 1.78 eq), cesium carbonate (510 mg, 1.56 mmol, 2.00 eq), and N,N-dimethylformamide (4 mL) were combined and hot block heated to 100° C. for 3 h. The reaction was cooled to room temperature and filtered to remove cesium salts. The crude was purified by prep HPLC followed by SFC to give 5-[(3R)-3-[(cyclopropylamino)methyl]pyrrolidin-1-yl]-N-(7-fluoro-2,8-dimethyl-imidazo[1,2-a]pyridin-6-yl)pyrazine-2-carboxamide. LCMS (ES+) 424.2 (M+H)+, RT 2.1 min (Analytical method AcHSSC18). $^1$H NMR (400 MHz, DMSO-$d_6$) d 9.82 (s, 1H), 8.99 (d, J=7.0 Hz, 1H), 8.75 (d, J=1.1 Hz, 1H), 8.05 (d, J=1.3 Hz, 1H), 7.74 (s, 1H), 3.78-3.66 (m, 2H), 3.58-3.40 (m, 1H), 3.29 (dd, J=7.2, 11.2 Hz, 1H), 2.75-2.62 (m, 2H), 2.56-2.48 (m, 1H), 2.42 (d, J=1.9 Hz, 3H), 2.35 (s, 3H), 2.16-2.08 (m, 2H), 1.76-1.74 (m, 1H), 0.40 (dd, J=1.6, 6.5 Hz, 2H), 0.27-0.23 (m, 2H).

Example 32: N-(8-Fluoro-2-methyl-imidazo[1,2-a]pyridin-6-yl)-5-(6-pyrrolidin-1-yl-3-azabicyclo[3.1.0]hexan-3-yl)pyrazine-2-carboxamide

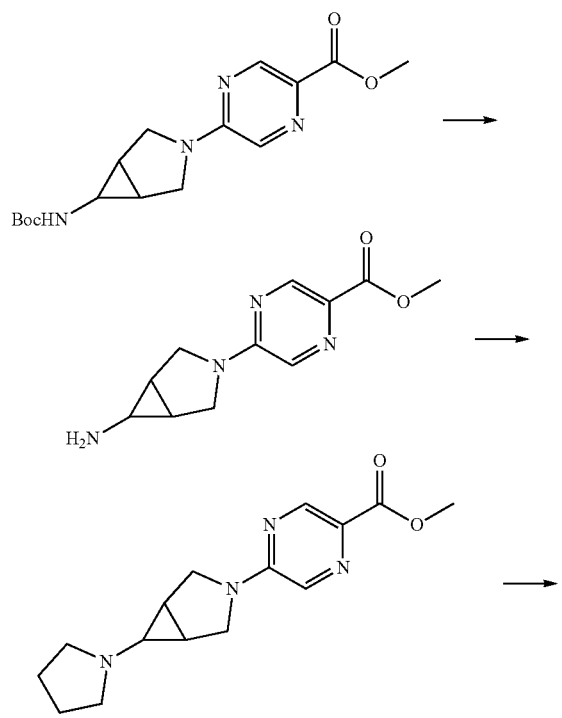

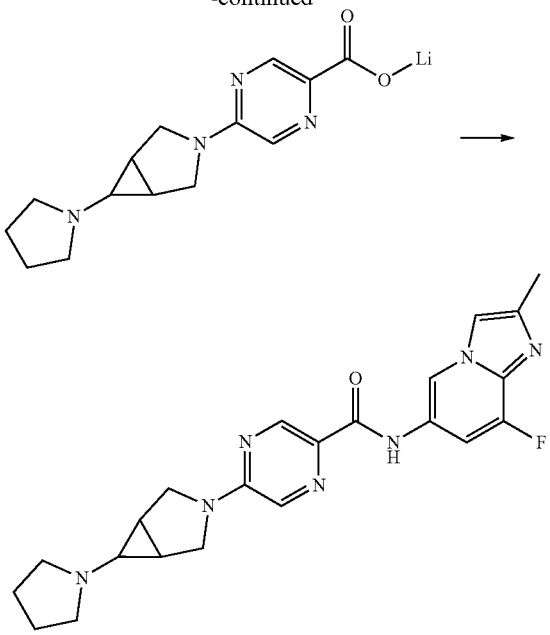

Methyl 5-[6-(tert-butoxycarbonylamino)-3-azabicyclo[3.1.0]hexan-3-yl]pyrazine-2-carboxylate (457 mg, 1.37 mmol, 1.00 eq), methyl alcohol (5 mL), and 4 M hydrogen chloride in dioxane (5.0 mL, 20.0 mmol, 14.6 eq) were combined and stirred at room temperature for 2 h. Reaction mixture was concentrated in vacuo to give methyl 5-(6-amino-3-azabicyclo[3.1.0]hexan-3-yl)pyrazine-2-carboxylate; hydrochloride, which was used directly in next step. LCMS (ES+) 235 (M+H)+.

Methyl 5-(6-amino-3-azabicyclo[3.1.0]hexan-3-yl)pyrazine-2-carboxylate; hydrochloride (1.36 mmol, 1.00 eq), 1,4-dibromobutane (0.16 mL, 1.36 mmol, 1.00 eq), acetonitrile (30 mL), and triethylamine (2 mL) were combined and reaction was hot block heated to 80° C. over a weekend. The reaction was cooled to room temperature. diluted with EtOAc, filtered to remove potassium salts, and concentrated in vacuo. Crude product was purified by prep HPLC to give methyl 5-(6-pyrrolidin-1-yl-3-azabicyclo[3.1.0]hexan-3-yl)pyrazine-2-carboxylate, which was used directly in next step. LCMS (ES+) 289 (M+H)+.

Methyl 5-(6-pyrrolidin-1-yl-3-azabicyclo[3.1.0]hexan-3-yl)pyrazine-2-carboxylate (49 mg, 0.170 mmol, 1.00 eq), lithium hydroxide monohydrate (7.8 mg, 0.187 mmol, 1.10 eq), methyl alcohol (5 mL), and water (0.5000 mL) were combined in a sealed tube and hot block heated to 50° C. over a weekend. The reaction was cooled to room temperature, concentrated in vacuo, and dried in a vac oven overnight to give [5-(6-pyrrolidin-1-yl-3-azabicyclo[3.1.0]hexan-3-yl)pyrazine-2-carbonyl]oxylithium, which was used directly in the next step. LCMS (ES+) 275 (M+H)+ as acid.

[5-(6-Pyrrolidin-1-yl-3-azabicyclo[3.1.0]hexan-3-yl)pyrazine-2-carbonyl]oxylithium (48 mg, 0.170 mmol, 1.00 eq), 8-fluoro-2-methyl-imidazo[1,2-a]pyridin-6-amine (28 mg, 0.170 mmol, 1.00 eq), HBTU (64 mg, 0.170 mmol, 1.00 eq), N,N-dimethylformamide (2 mL), and triethylamine (0.024 mL, 0.170 mmol, 1.00 eq) were combined and stirred at room temperature for 2 h. Reaction mixture was purified by prep HPLC to give the title compound. LCMS (ES+) 422.2 (M+H)+, RT 1.86 min (Analytical method AcHSSC18). ¹H NMR (400 MHz, DMSO-d₆) d 10.43 (s, 1H), 9.19 (d, J=1.6 Hz, 1H), 8.74 (d, J=1.1 Hz, 1H), 7.96 (d, J=1.3 Hz, 1H), 7.89 (d, J=2.8 Hz, 1H), 7.57 (dd, J=1.5, 13.3 Hz, 1H), 3.80 (d, J=11.2 Hz, 2H), 3.60 (dd, J=2.2, 9.0 Hz, 2H), 2.60 (s, 5H), 2.35 (s, 3H), 1.84 (s, 2H), 1.68 (d, J=3.0 Hz, 4H). ¹⁹F NMR (376 MHz, DMSO-d₆) d −132.17 (dd, J=3.9 Hz, J=13.2 Hz).

Example 33: 5-(4-((cyclopropylamino)methyl)piperidin-1-yl)-N-(8-fluoro-2-methylimidazo[1,2-a]pyridin-6-yl)pyrazine-2-carboxamide

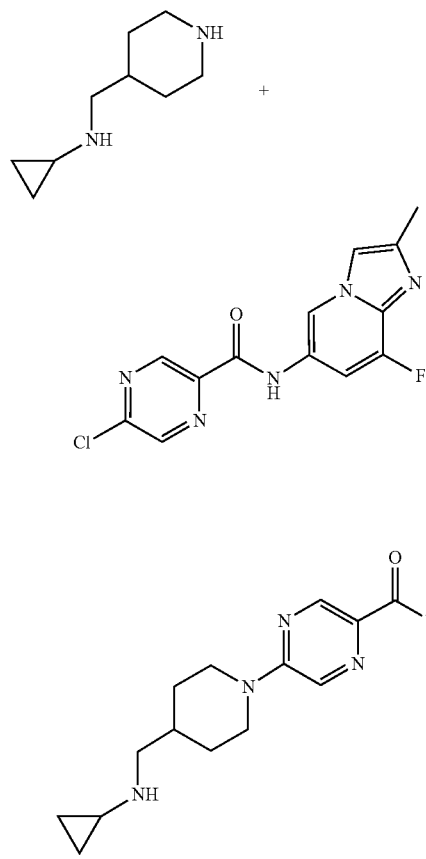

N-(4-piperidylmethyl)cyclopropanamine (50 mg, 0.327 mmol), 5-chloro-N-(8-fluoro-2-methyl-imidazo[1,2-a]pyridin-6-yl)pyrazine-2-carboxamide (100 mg, 0.327 mmol), and cesium carbonate (213 mg, 0.654 mmol, 2.00 eq) in N,N-dimethylformamide (1 mL) were stirred for 18 h at 100° C. The reaction mixture was diluted with DMSO and purified by prep-HPLC. This yielded 5-(4-((cyclopropylamino)methyl)piperidin-1-yl)-N-(8-fluoro-2-methylimidazo[1,2-a]pyridin-6-yl)pyrazine-2-carboxamide. LCMS (ES+) 424.2 (M+H)+, RT 2.03 min (Analytical method AcHSSC18); ¹H NMR (400 MHz, DMSO-d₆) 10.41 (1H, s), 9.17 (1H, d, J=1.6 Hz), 8.71 (1H, d, J=1.3 Hz), 8.31 (1H, d, J=1.4 Hz), 7.88 (1H, dd, J=0.6, 3.1 Hz), 7.55 (1H, dd, J=1.6, 13.1 Hz), 4.55-4.47 (2H, m), 3.04-2.95 (2H, m), 2.48-2.46 (2H, m), 2.34-2.33 (4H, m), 2.08-2.01 (1H, m), 1.83-1.71 (3H, m), 1.18-1.07 (2H, m), 0.37-0.32 (2H, m), 0.21-0.16 (2H, m); ¹⁹F NMR (376 MHz, DMSO-d₆) d −132.19 (dd, J=12.5, 2.6 Hz).

Example 34: 5-(6-(ethylamino)-3-azabicyclo[3.1.0]hexan-3-yl)-N-(8-methoxy-2-methylimidazo[1,2-a]pyrazin-6-yl)pyrazine-2-carboxamide

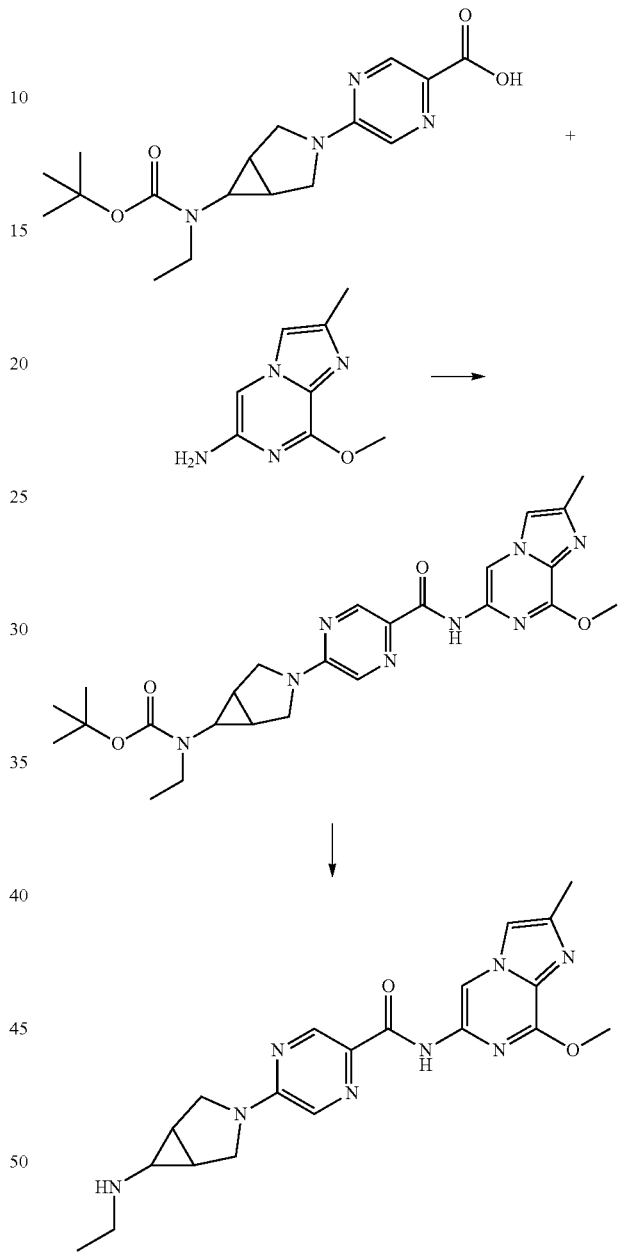

5-[6-[tert-Butoxycarbonyl(ethyl)amino]-3-azabicyclo[3.1.0]hexan-3-yl]pyrazine-2-carboxylic acid (102 mg, 0.293 mmol, 1.00 eq), 8-methoxy-2-methyl-imidazo[1,2-a]pyrazin-6-amine (52 mg, 0.293 mmol, 1.00 eq), HBTU (111 mg, 0.293 mmol, 1.00 eq), N,N-dimethylformamide (2 mL), and triethylamine (0.54 mL, 3.85 mmol, 13.2 eq) were combined and stirred at room temperature for 3 h. The mixture was then cooled to room temperature and purified by prep HPLC to afford tert-butyl ethyl(3-(5-((8-methoxy-2-methylimidazo[1,2-a]pyrazin-6-yl)carbamoyl)pyrazin-2-yl)-3-azabicyclo[3.1.0]hexan-6-yl)carbamate. LCMS (ES+) 509.2 (M+H)+, RT 4.45 min (Analytical method AcHSSC18). $^1$H NMR (400 MHz, DMSO-d$_6$) 9.52 (1H, s), 8.91 (1H, s), 8.76 (1H, d, J=1.5 Hz), 8.06 (1H, d, J=1.3 Hz), 7.95 (1H, d, J=0.9 Hz), 4.07 (3H, s), 3.87 (2H, d, J=11.4 Hz), 3.70-3.66 (2H, m), 3.28-3.22 (2H, m), 2.36 (3H, s), 2.28-2.25 (1H, m), 2.09 (2H, bs), 1.45 (9H, s), 1.09-1.04 (3H, m).

tert-Butyl N-ethyl-N-[3-[5-[(8-methoxy-2-methyl-imidazo[1,2-a]pyrazin-6-yl)carbamoyl]pyrazin-2-yl]-3-azabicyclo[3.1.0]hexan-6-yl]carbamate (21 mg, 0.0422 mmol, 1.00 eq), methyl alcohol (2 mL), and 4 M hydrogen chloride in dioxane (2.0 mL, 8.00 mmol, 190 eq) were combined and stirred at room temperature for 90 minutes. The mixture was concentrated in vacuo and purified by prep HPLC followed by SFC to give 5-(6-(ethylamino)-3-azabicyclo[3.1.0]hexan-3-yl)-N-(8-methoxy-2-methylimidazo[1,2-a]pyrazin-6-yl)pyrazine-2-carboxamide. LCMS (ES+) 409.2 (M+H)+, RT 2.06 min (Analytical method AcHSSC18). $^1$H NMR (400 MHz, DMSO-d$_6$) 9.51 (1H, s), 8.90 (1H, s), 8.74 (1H, d, J=1.4 Hz), 8.01 (1H, d, J=1.6 Hz), 7.95 (1H, d, J=0.8 Hz), 4.07 (3H, s), 3.77 (2H, d, J=11.7 Hz), 3.63-3.59 (2H, m), 2.63-2.60 (2H, m), 2.35 (3H, s), 2.19 (1H, bs), 1.91-1.88 (1H, m), 1.73 (2H, bs), 1.02 (3H, t, J=6.7 Hz).

Example 35 and Example 36: 5-((1S)-1-amino-3-azabicyclo[3.1.0]hexan-3-yl)-N-(8-fluoro-2-methyl-imidazo[1,2-a]pyridin-6-yl)pyrazine-2-carboxamide and 5-((1R)-1-amino-3-azabicyclo[3.1.0]hexan-3-yl)-N-(8-fluoro-2-methylimidazo[1,2-a]pyridin-6-yl)pyrazine-2-carboxamide

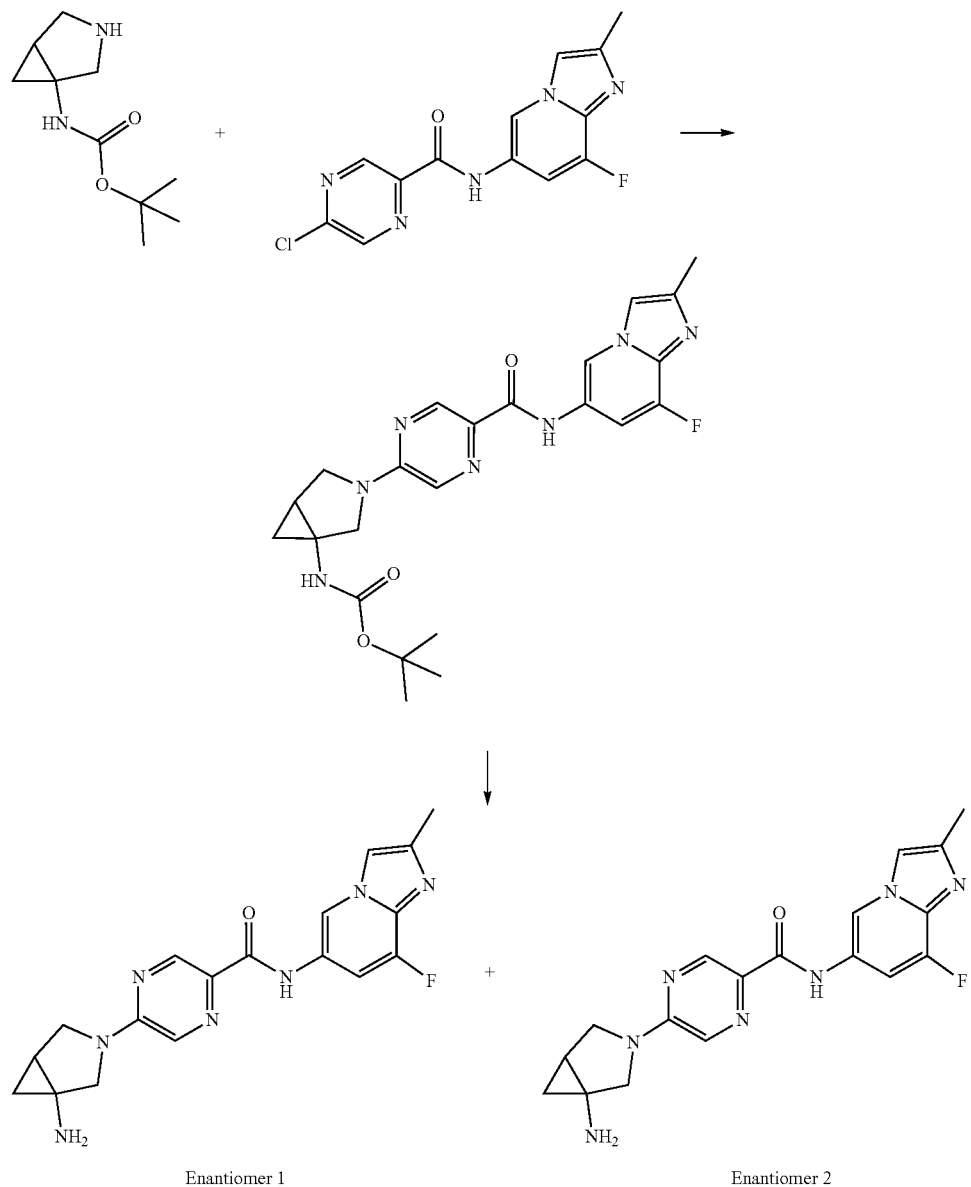

Cesium carbonate (394 mg, 1.21 mmol, 1.50 eq), 5-chloro-N-(8-fluoro-2-methyl-imidazo[1,2-a]pyridin-6-yl)pyrazine-2-carboxamide (247 mg, 0.807 mmol, 1.00 eq), tert-butyl N-(3-azabicyclo[3.1.0]hexan-1-yl)carbamate (160 mg, 0.807 mmol, 1.00 eq), and N,N-dimethylformamide (4 mL) were combined in a sealed tube and hot block heated to 100° C. for 90 minutes. The mixture was then cooled to room temperature, the cesium salts were filtered off, and the residue was purified by prep HPLC to afford tert-butyl N-(3-(5-((8-fluoro-2-methylimidazo[1,2-a]pyridin-6-yl)carbamoyl)pyrazin-2-yl)-3-azabicyclo[3.1.0]hexan-1-yl)carbamate. LCMS (ES+) 419.2 (M+H)+, RT 1.81 min (Analytical method AcHSSC18). $^1$H NMR (400 MHz, DMSO-$d_6$) 10.47 (1H, s), 9.19 (1H, d, J=1.7 Hz), 8.75 (1H, d, J=1.3 Hz), 8.00 (1H, d, J=1.0 Hz), 7.90 (1H, dd, J=1.0, 3.0 Hz), 7.62-7.55 (2H, m), 3.98 (1H, d, J=10.8 Hz), 3.80-3.72 (2H, m), 3.58-3.55 (1H, m), 2.35 (3H, s), 1.42 (9H, s), 1.13-1.08 (1H, m), 0.90-0.88 (1H, m), 0.73-0.70 (1H, m).

tert-Butyl N-[3-[5-[(8-fluoro-2-methyl-imidazo[1,2-a]pyridin-6-yl)carbamoyl]pyrazin-2-yl]-3-azabicyclo[3.1.0]hexan-1-yl]carbamate (199 mg, 0.426 mmol, 1.00 eq), methyl alcohol (2 mL), and 4 M hydrogen chloride in dioxane (2.0 mL, 8.00 mmol, 18.8 eq) were combined and stirred at room temperature for 24 h. The mixture was concentrated in vacuo and purified by prep HPLC followed by SFC to give the two compounds: Enantiomer 2, LCMS (ES+) 368.2 (M+H)+, RT 2.92 min (Analytical method AcHSSC18 BicarbBEHC18) $^1$H NMR (400 MHz, DMSO-$d_6$) d 10.45 (s, 1H), 9.19 (d, J=1.4 Hz, 1H), 8.76 (d, J=1.4 Hz, 1H), 7.99 (d, J=1.4 Hz, 1H), 7.91-7.90 (m, 1H), 7.56 (dd, J=1.5, 13.6 Hz, 1H), 4.04 (d, J=11.5 Hz, 1H), 3.78-3.71 (m, 2H), 3.57 (d, J=10.1 Hz, 1H), 2.35 (s, 3H), 1.81 (bs, 1H), 1.18-1.14 (m, 1H), 0.68-0.65 (m, 1H), NH2 not observed; and Enantiomer 1, LCMS (ES+) 368.2 (M+H)+, RT 2.93 min (Analytical method AcHSSC18 BicarbBEHC18) $^1$H NMR (400 MHz, DMSO-$d_6$) 10.45 (1H, s), 9.19 (1H, d, J=1.6 Hz), 8.75 (1H, d, J=1.6 Hz), 7.99 (1H, d, J=1.5 Hz), 7.91-7.89 (1H, m), 7.57 (1H, dd, J=1.8, 13.2 Hz), 4.02 (1H, d, J=10.6 Hz), 3.77-3.70 (2H, m), 3.55 (1H, d, J=10.6 Hz), 2.35 (3H, s), 1.74 (1H, s), 1.15-1.10 (1H, m), 0.64-0.61 (1H, m), NH2 not observed.

Example 37: 5-[6-(Cyclopropylamino)-3-azabicyclo[3.1.0]hexan-3-yl]-N-(8-fluoro-2-methyl-imidazo[1,2-a]pyridin-6-yl)pyrazine-2-carboxamide 5-(6-Amino-3-azabicyclo[3.1.0]hexan-3-yl)-N-(8-fluoro-2-methyl-imidazo[1,2-a]pyridin-6-yl)pyrazine-2-carboxamide (220 mg, 0.600 mmol, 1.00 eq), (1-ethoxycyclopropoxy)trimethylsilane (0.097 mL, 0.480 mmol, 0.800 eq), sodium cyanoborohydride (57 mg, 0.900 mmol, 1.50 eq), methyl alcohol (15 mL), and acetic acid (0.2000 mL) were combined and hot block heated to 50° C. overnight. The reaction mixture was cooled to room temperature, concentrated in vacuo and purified by prep HPLC and SFC purification to give the title compound. LCMS (ES+) 408.2 (M+H)+, RT 1.87 min (Analytical method AcHSSC18). $^1$H NMR (400 MHz, DMSO-$d_6$) d 10.41 (s, 1H), 9.18 (d, J=1.5 Hz, 1H), 8.72 (d, J=1.1 Hz, 1H), 7.94 (d, J=1.3 Hz, 1H), 7.88 (d, J=2.6 Hz, 1H), 7.55 (dd, J=1.7, 13.1 Hz, 1H), 3.78 (d, J=11.2 Hz, 2H), 3.59 (dd, J=2.0, 9.0 Hz, 2H), 2.67 (dd, J=1.8, 3.6 Hz, 1H), 2.33 (s, 3H), 2.16-2.10 (m, 1H), 1.96 (dd, J=2.3, 2.3 Hz, 1H), 1.72 (s, 2H), 0.38-0.33 (m, 2H), 0.25-0.21 (m, 2H). $^{19}$F NMR (376 MHz, DMSO-$d_6$) d −132.17 (dd, J=2.8 Hz, J=13.5 Hz).

Method Q: Formaldehyde Reductive Amination

Amine (1 eq), formaldehyde (37% solution, 50 eq), methanol (1 mL), and sodium triacetoxyborohydride (2 eq) were combined and the resulting mixture was stirred at rt for 16 h. The mixture was partitioned between DCM and saturated sodium bicarbonate, dried and evaporated. The crude material was purified by achiral SFC or prep HPLC.

Example 38 and Example 39: (S*)-5-(3-(dimethylamino)-2-oxopyrrolidin-1-yl)-N-(8-fluoro-2-methyl-imidazo[1,2-a]pyridin-6-yl)pyrazine-2-carboxamide and (R*)-5-(3-(dimethylamino)-2-oxopyrrolidin-1-yl)-N-(8-fluoro-2-methylimidazo[1,2-a]pyridin-6-yl)pyrazine-2-carboxamide

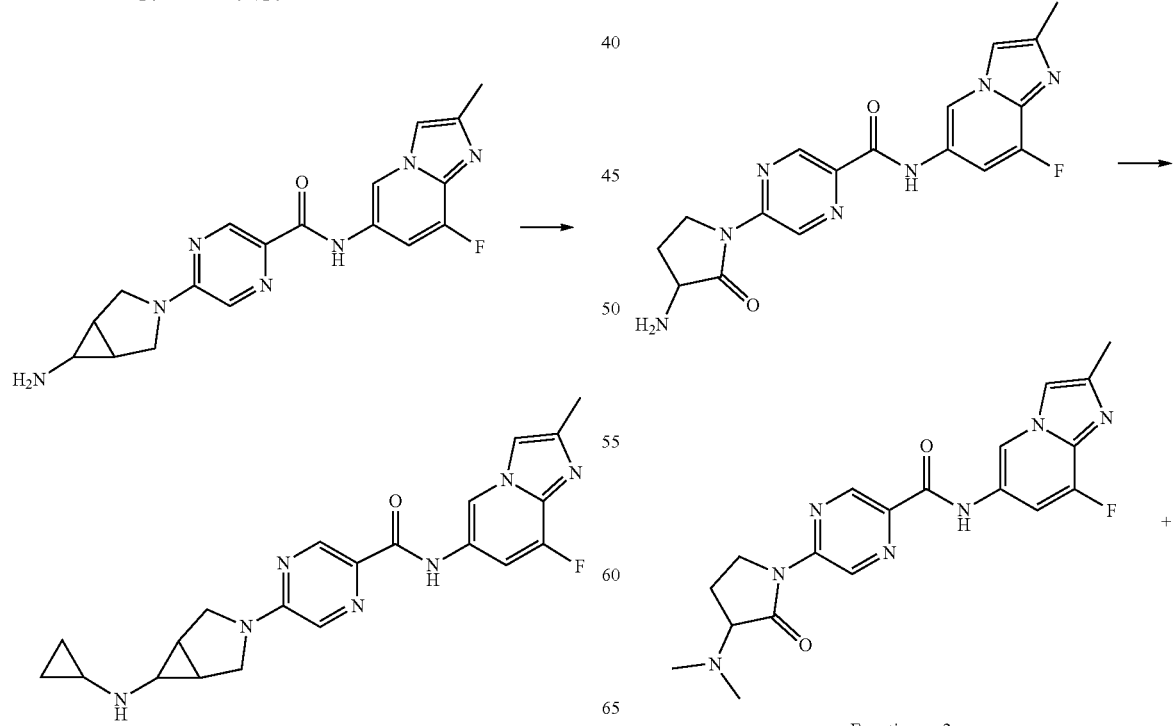

Enantiomer 2

-continued

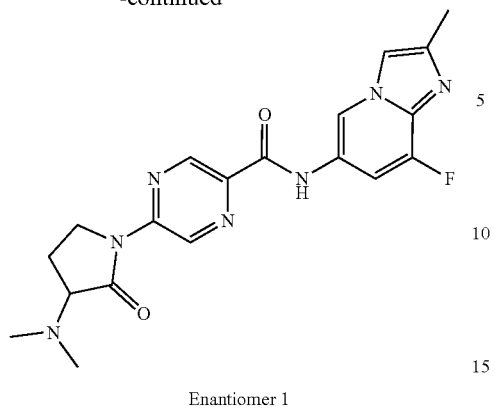

Enantiomer 1

Following Method Q (Formaldehyde reductive amination) from previously reported 5-(3-amino-2-oxopyrrolidin-1-yl)-N-(8-fluoro-2-methylimidazo[1,2-a]pyridin-6-yl)pyrazine-2-carboxamide (100 mg, 0.27 mmol), and purified by chiral SFC gave Enantiomer 2, LCMS (ES+) 398.2 (M+H)+, RT 1.72 min (Analytical method AcHSSC18). RT 2.01 min (SFC1, LUX CELLULOSE-3+0.1% DEAISO 30% ACN/IPA SOL4). $^1$H NMR (400 MHz, DMSO-$d_6$) d 10.91 (s, 1H), 9.72 (d, J=1.5 Hz, 1H), 9.23 (d, J=1.6 Hz, 1H), 9.13 (d, J=1.4 Hz, 1H), 7.94 (d, J=2.8 Hz, 1H), 7.59 (dd, J=1.6, 13.0 Hz, 1H), 4.12-4.06 (m, 1H), 3.83-3.74 (m, 2H), 2.38 (d, J=11.7 Hz, 9H), 2.30-2.22 (m, 1H), 2.16-2.04 (m, 1H). $^{19}$F NMR (400 MHz, DMSO-$d_6$) d −131.85 (dd, J=2.7, 12.3 Hz); and Enantiomer 1, LCMS (ES+) 398.2 (M+H)+, RT 1.72 min (Analytical method AcHSSC18). RT 4.69 min (SFC1, LUX CELLULOSE-3+0.1% DEAISO 30% ACN/IPA SOL4). $^1$H NMR (400 MHz, DMSO-$d_6$) d 10.91 (s, 1H), 9.72 (d, J=1.5 Hz, 1H), 9.23 (d, J=1.6 Hz, 1H), 9.13 (d, J=1.5 Hz, 1H), 7.94 (d, J=2.8 Hz, 1H), 7.59 (dd, J=1.9, 13.0 Hz, 1H), 4.12-4.06 (m, 1H), 3.83-3.75 (m, 2H), 2.39 (s, 6H), 2.36 (d, J=0.7 Hz, 3H), 2.31-2.23 (m, 1H), 2.16-2.04 (m, 1H). $^{19}$F NMR (400 MHz, DMSO-$d_6$) d −131.85 (dd, J=2.7, 12.3 Hz).

Example 40 and Example 41: (R*)-5-(4-((cyclopropylamino)methyl)-2-oxopyrrolidin-1-yl)-N-(8-fluoro-2-methylimidazo[1,2-a]pyridin-6-yl)pyrazine-2-carboxamide and (S*)-5-(4-((cyclopropylamino)methyl)-2-oxopyrrolidin-1-yl)-N-(8-fluoro-2-methylimidazo[1,2-a]pyridin-6-yl)pyrazine-2-carboxamide

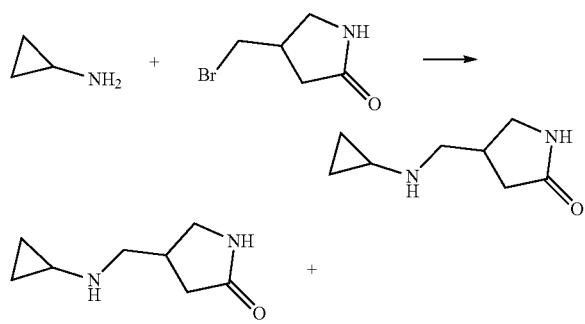

-continued

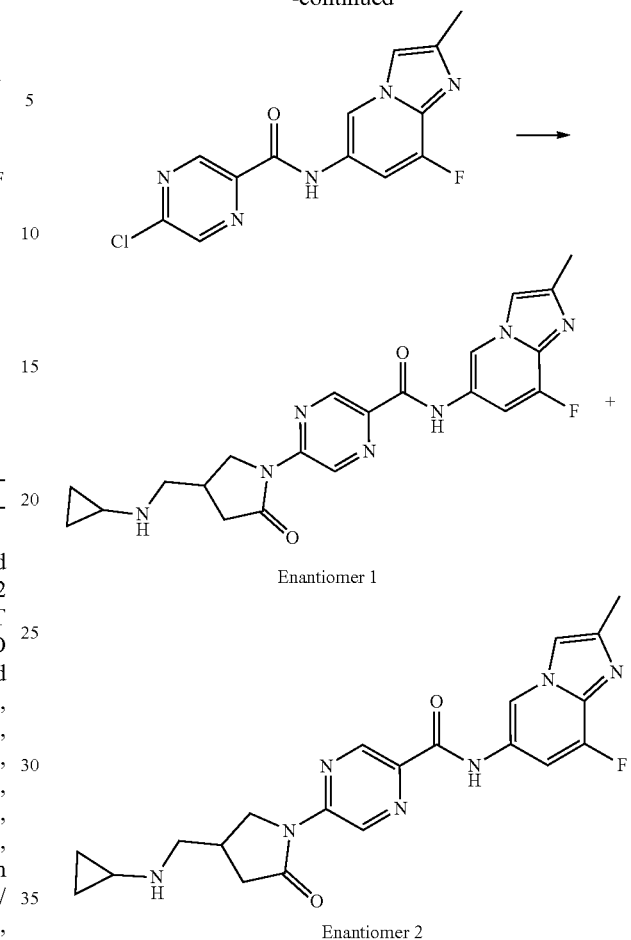

Enantiomer 1

Enantiomer 2

A mixture of 4-(bromomethyl)pyrrolidin-2-one (500 mg, 2.81 mmol, 1 eq), cyclopropylamine (0.29 mL, 4.21 mmol, 1.5 eq), potassium carbonate (776 mg, 5.62 mmol, 2 eq), and 4-(dimethylamino)pyridine (69 mg, 0.562 mmol, 0.2 eq) in acetonitrile (14.04 mL) were placed in an Ace pressure tube and heated to 100° C. A blast shield was placed around the set up and the mixture was left stirring overnight. The reaction mixture was cooled to RT, solvent was evaporated in vacuo and the residue was purified by chromatography (silica gel, gradient elution ethyl acetate+7 N $NH_3$ in MeOH 1:0 to 84:16). $^1$H NMR (400 MHz, $CDCl_3$) d, 5.87-5.86 (brs, 1H), 3.50 (dd, J=8.7, 8.7 Hz, 1H), 3.13 (dd, J=5.7, 9.7 Hz, 1H), 2.82-2.61 (m, 3H), 2.45 (dd, J=8.8, 16.9 Hz, 1H), 2.14-2.01 (m, 2H), 0.48-0.41 (m, 2H), 0.33-0.28 (m, 2H).

To a solution of 5-chloro-N-(8-fluoro-2-methyl-imidazo[1,2-a]pyridin-6-yl)pyrazine-2-carboxamide (99 mg, 0.324 mmol, 1 eq) and 4-[(cyclopropylamino)methyl]pyrrolidin-2-one (50 mg, 0.324 mmol, 1 eq) in 1,4-dioxane (2.14 mL) was added cesium carbonate (158 mg, 0.486 mmol, 1.5 eq) and the mixture was degassed under $N_2$ sparging for 20 min. Xantphos (19 mg, 0.0324 mmol, 0.1 eq) and tris(dibenzylideneacetone)dipalladium(0) (7.4 mg, 8.11 mol, 0.025 eq) was added and the mixture heated to 100° C. under inert atmosphere for 24 h. The reaction mixture was cooled down and concentrated in vacuo. The residue was purified by chromatography (silica gel, gradient elution ethyl acetate/isopropanol 1:0 to 80:20 slow gradient over 15 column volumes then isocratic) prior to chiral SFC separation to yield Enantiomer 1, LCMS (ES+) 424.2 (M+H)+, RT 1.83 min (Analytical method AcHSSC18) $^1$H NMR (400 MHz, DMSO-d$_6$) d 10.89 (s, 1H), 9.69 (d, J=1.4 Hz, 1H), 9.24 (d, J=1.5 Hz, 1H), 9.12 (d, J=1.5 Hz, 2H), 7.95 (d, J=2.8 Hz, 1H), 7.60 (dd, J=1.8, 12.7 Hz, 1H), 4.14 (dd, J=7.7, 11.1 Hz, 1H), 3.78 (dd, J=5.6, 11.2 Hz, 1H), 2.84-2.63 (m, 4H), 2.38 (s, 3H), 2.13-2.07 (m, 1H), 0.42-0.38 (m, 2H), 0.26-0.21 (m, 2H); $^{19}$F NMR (376 MHz, DMSO-d$_6$) d −131.86 (dd, J=2.4, 12.2 Hz, 1F); and Enantiomer 2, LCMS (ES+) 424.2 (M+H)+, RT 1.84 min (Analytical method AcHSSC18) $^1$H NMR (400 MHz, DMSO-d$_6$) d 10.89 (s, 1H), 9.69 (d, J=1.4 Hz, 1H), 9.24 (d, J=1.5 Hz, 1H), 9.12 (d, J=1.5 Hz, 2H), 7.95 (d, J=2.8 Hz, 1H), 7.60 (dd, J=1.8, 12.7 Hz, 1H), 4.14 (dd, J=7.7, 11.1 Hz, 1H), 3.78 (dd, J=5.6, 11.2 Hz, 1H), 2.84-2.63 (m, 4H), 2.38 (s, 3H), 2.13-2.07 (m, 1H), 0.42-0.38 (m, 2H), 0.26-0.21 (m, 2H); $^{19}$F NMR (376 MHz, DMSO-d$_6$) d −131.86 (dd, J=2.4, 12.2 Hz, 1F).

Example 42: 5-(3-Amino-3-methyl-pyrrolidin-1-yl)-N-(8-fluoro-2-methyl-imidazo[1,2-a]pyridin-6-yl)pyrazine-2-carboxamide, racemic

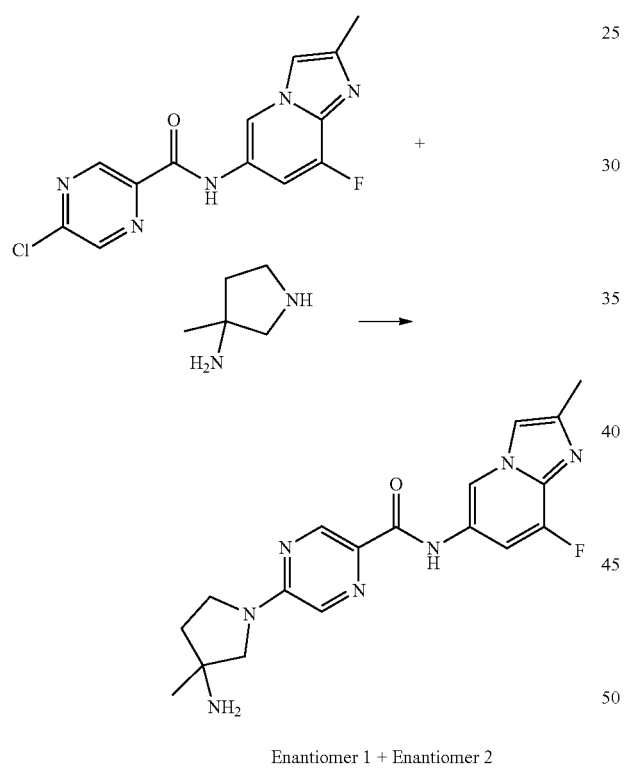

3-Methylpyrrolidin-3-amine; dihydrochloride (121 mg, 0.699 mmol, 1.00 eq), 5-chloro-N-(8-fluoro-2-methyl-imidazo[1,2-a]pyridin-6-yl)pyrazine-2-carboxamide (214 mg, 0.699 mmol, 1.00 eq), cesium carbonate (456 mg, 1.40 mmol, 2.00 eq), and N,N-dimethylformamide (5 mL) were combined in a sealed tube and hot block heated to 80° C. overnight. The reaction was cooled to room temperature, filtered to remove cesium salts, and purified by prep HPLC to give the racemic title compound. LCMS (ES+) 370.519 (M+H)+, RT 1.72 min (Analytical method AcHSSC18). $^1$H NMR (400 MHz, DMSO-d$_6$) d 10.42 (s, 1H), 9.20 (d, J=1.5 Hz, 1H), 8.74 (s, 1H), 7.94 (s, 1H), 7.90 (d, J=2.8 Hz, 1H), 7.57 (dd, J=1.7, 13.1 Hz, 1H), 3.75-3.61 (m, 2H), 3.42-3.37 (m, 2H), 2.35 (s, 3H), 1.88-1.88 (m, 4H), 1.30 (s, 3H). $^{19}$F NMR (400 MHz, DMSO-d$_6$) d −132.18 (dd, J=2.6 Hz, J=13.5 Hz).

Example 43 and Example 44: (R)-5-(3-(cyclopropylamino)-2-oxopyrrolidin-1-yl)-N-(8-fluoro-2-methylimidazo[1,2-a]pyridin-6-yl)pyrazine-2-carboxamide and (S)-5-(3-(cyclopropylamino)-2-oxopyrrolidin-1-yl)-N-(8-fluoro-2-methylimidazo[1,2-a]pyridin-6-yl)pyrazine-2-carboxamide

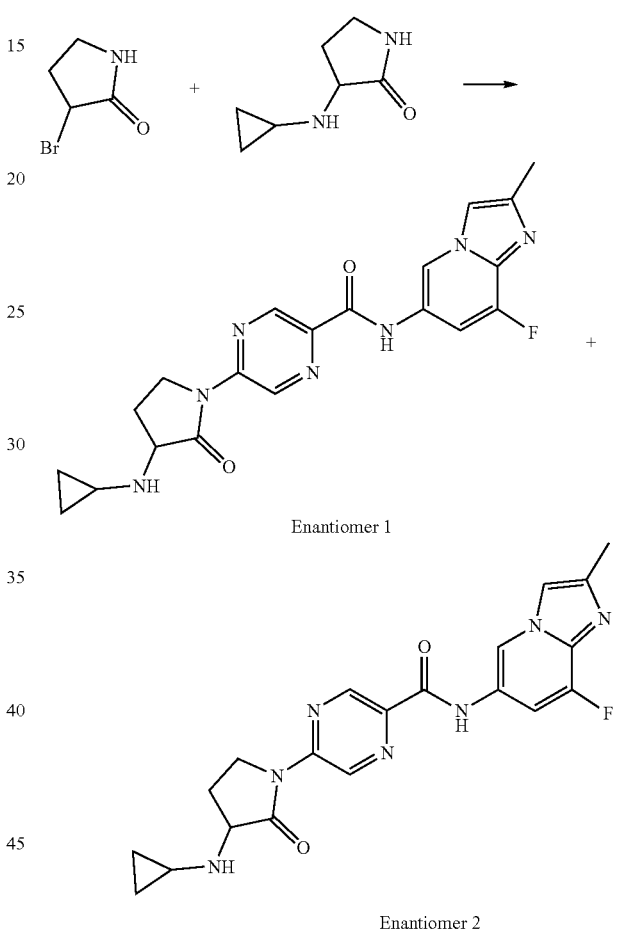

3-Bromopyrrolidin-2-one (250 mg, 1.52 mmol, 1.00 eq), cyclopropylamine (0.13 mL, 1.83 mmol, 1.20 eq), triethylamine (0.64 mL, 4.57 mmol, 3.00 eq), and 4-(dimethylamino)pyridine (37 mg, 0.305 mmol, 0.200 eq) were combined in acetonitrile (7.62 mL) and sealed and heated to 100° C. for 18 h. The cooled reaction mixture was concentrated in vacuo and loaded in DCM and eluted with ethyl acetate 100% to ammonia in methanol (7 N) 2.5%. The product was isolated, (contaminated with DMAP 20% by HNMR) and used with no further purification.

To a solution of 5-chloro-N-(8-fluoro-2-methyl-imidazo[1,2-a]pyridin-6-yl)pyrazine-2-carboxamide (473 mg, 1.55 mmol, 1.00 eq) and tert-butyl 3-oxo-1,2,3a,4,6,6a-hexahydropyrrolo[3,4-c]pyrrole-5-carboxylate (350 mg, 1.55 mmol, 1.00 eq) in 1,4-dioxane (5.16 mL) was added cesium carbonate (756 mg, 2.32 mmol, 1.50 eq) and the mixture was deoxygenated under N$_2$ sparging for 20 min. Xantphos (90 mg, 0.155 mmol, 0.100 eq) and tris(dibenzylideneacetone)dipalladium(0) (35 mg, 0.0387 mmol, 0.0250 eq) were added and the mixture heated to 100° C. under inert atmosphere for 24 h. The cooled reaction mixture was concentrated (and combined with an identical reaction on 60 mg scale of 3-(cyclopropylamino)pyrrolidin-2-one) then diluted with DCM/acetone and eluted over 12 g silica gel column using ethyl acetate/isopropyl alcohol (0-5%). The racemic product was isolated, which was further purified by SFC YMC Amylose-C 10×250 mm, 5 um 55/45 ACN/IPA (0.1% DEA)/$CO_2$, 15 ml/min, 120 bar, 40° C., DAD 270 nm, to give the products: Enantiomer 1, 97.3% Rt=1.86, ee, 100%, Rt=5.41. LCMS (ES+) 410.2 (M+H)+, RT 1.85 min (Analytical method AcHSSC18) $^1$H NMR (400 MHz, DMSO-$d_6$) d 10.90 (s, 1H), 9.72 (d, J=1.4 Hz, 1H), 9.24 (d, J=1.6 Hz, 1H), 9.13 (d, J=1.4 Hz, 1H), 8.33-8.19 (m, 1H), 7.94 (d, J=2.8 Hz, 1H), 7.59 (dd, J=1.6, 13.0 Hz, 1H), 4.14-4.09 (m, 1H), 3.86-3.78 (m, 2H), 2.99-2.90 (m, 2H), 2.36 (s, 3H), 2.00-1.92 (m, 1H), 0.47-0.44 (m, 2H), 0.36-0.30 (m, 2H); and Enantiomer 2, 95.23% Rt=1.86, ee, 98.3%, Rt=13.15. LCMS (ES+) 410.2 (M+H)+, RT 1.85 min (Analytical method AcHSSC18) $^1$H NMR (400 MHz, DMSO-$d_6$) d 10.90 (s, 1H), 9.72 (d, J=1.4 Hz, 1H), 9.24 (d, J=1.6 Hz, 1H), 9.13 (d, J=1.4 Hz, 1H), 8.33-8.19 (m, 1H), 7.94 (d, J=2.8 Hz, 1H), 7.59 (dd, J=1.6, 13.0 Hz, 1H), 4.14-4.09 (m, 1H), 3.86-3.78 (m, 2H), 2.99-2.90 (m, 2H), 2.36 (s, 3H), 2.00-1.92 (m, 1H), 0.47-0.44 (m, 2H), 0.36-0.30 (m, 2H).

Example 45: 5-(3-((3-(2-(dimethylamino)-2-oxoethoxy)azetidin-1-yl)methyl)azetidin-1-yl)-N-(8-fluoro-2-methylimidazo[1,2-a]pyridin-6-yl)pyrazine-2-carboxamide

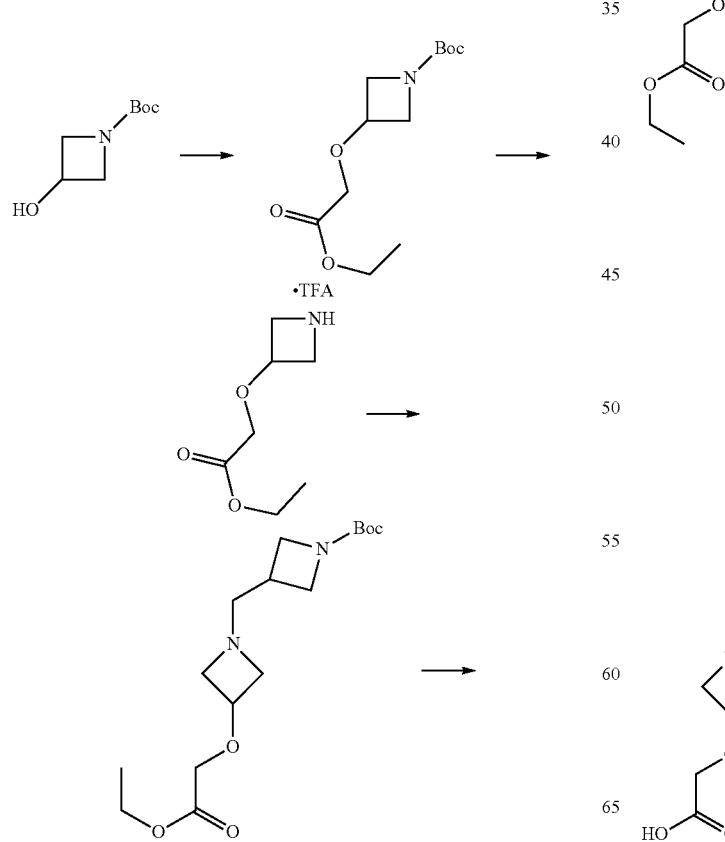

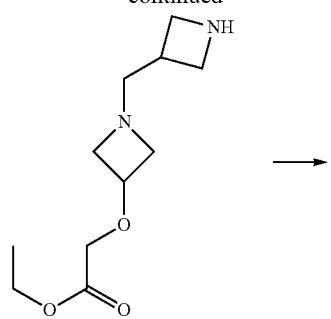

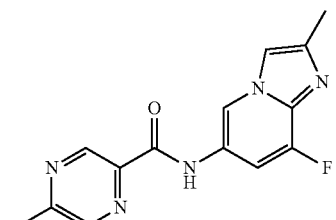

-continued

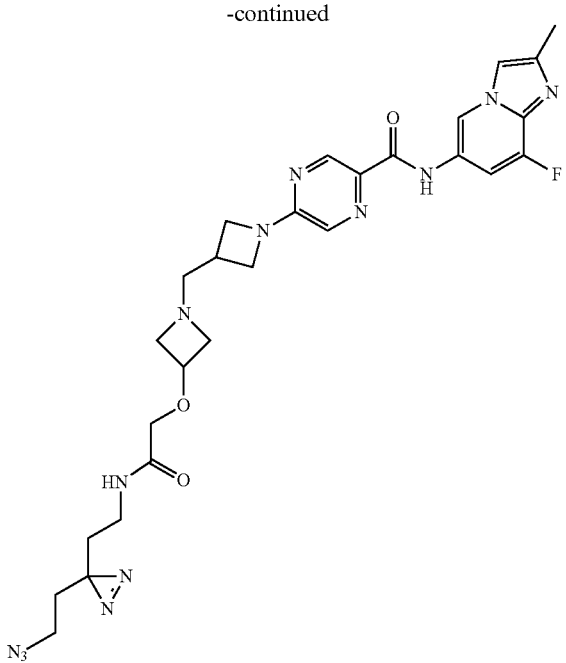

Ethyl bromoacetate (1.9 mL, 17.3 mmol, 1 eq) and sodium hydride (60%, 0.83 g, 20.8 mmol, 1.2 eq) were combined in tetrahydrofuran (40 mL). This was followed by the addition of a solution of 1-Boc-3-hydroxyazetidine (3.00 g, 17.3 mmol, 1 eq) in tetrahydrofuran (10 mL) dropwise with stirring in 2 min. The resulting solution was stirred for 2 h at room temperature. The reaction was then quenched by the addition of water (20 mL). The resulting solution was diluted with water (20 mL). The resulting solution was extracted with ethyl acetate (3×40 mL) and the organic layers combined. The resulting mixture was washed with saturated aqueous sodium chloride (3×40 mL). The mixture was dried over anhydrous magnesium sulfate and concentrated under vacuum. Purification by flash silica chromatography (80 g Interchim cartridge, 20% EtOAc in c-hex to 100% EtOAc) gave tert-butyl 3-(2-ethoxy-2-oxo-ethoxy) azetidine-1-carboxylate. $^1$H NMR (400 MHz, CDCl$_3$) $\delta$ 4.37-4.31 (m, 1H), 4.23 (q, J=7.2 Hz, 2H), 4.09 (dd, J=6.7, 10.2 Hz, 2H), 4.04 (s, 2H), 3.92 (dd, J=4.4, 10.1 Hz, 2H), 1.44 (s, 9H), 1.29 (t, J=7.2 Hz, 3H).

tert-Butyl 3-(2-ethoxy-2-oxo-ethoxy)azetidine-1-carboxylate (500 mg, 1.93 mmol, 1 eq) and trifluoroacetic acid (0.74 mL, 9.64 mmol, 5 eq) were combined in dichloromethane (20 mL) and stirred at r.t. for 17 h. The reaction mixture was concentrated to dryness to give ethyl 2-(azetidin-3-yloxy)acetate. $^1$H NMR (400 MHz, CDCl$_3$) $\delta$ 8.80 (s, 1H), 8.33 (s, 1H), 4.58-4.50 (m, 1H), 4.41-4.31 (m, 2H), 4.29-4.19 (m, 4H), 4.14 (s, 2H), 1.30-1.26 (m, 3H).

tert-Butyl 3-formylazetidine-1-carboxylate (339 mg, 1.83 mmol, 1 eq), sodium triacetoxyborohydride (776 mg, 3.66 mmol, 2 eq), and ethyl 2-(azetidin-3-yloxy)acetate; 2,2,2-trifluoroacetic acid (500 mg, 1.83 mmol, 1 eq) were combined in dichloromethane (20 mL) and stirred at r.t. overnight. The reaction mixture was quenched with saturated NaHCO$_3$ (aq) (50 mL) and the organics were separated and washed with water and brine. The organics were dried over magnesium sulfate, filtered and concentrated to dryness, before passing through an SCX cartridge (10 g) eluting with DCM:MeOH:7 M methanolic ammonia (10:10:1). The collected fraction was concentrated to dryness to give tert-butyl 3-[[3-(2-ethoxy-2-oxo-ethoxy)azetidin-1-yl]methyl]azetidine-1-carboxylate. $^1$H NMR (400 MHz, CDCl$_3$) $\delta$ 4.24-4.16 (m, 3H), 4.01 (s, 2H), 3.97 (t, J=8.1 Hz, 2H), 3.71-3.55 (m, 4H), 3.03-2.98 (m, 2H), 2.68-2.65 (m, 2H), 2.56-2.44 (m, 1H), 1.43 (s, 9H), 1.29 (t, J=6.4 Hz, 3H).

Trifluoroacetic acid (3 mL, 39 mmol, 39 eq) and tert-butyl 3-[[3-(2-ethoxy-2-oxo-ethoxy)azetidin-1-yl]methyl]azetidine-1-carboxylate (330 mg, 1 mmol, 1 eq) were combined in dichloromethane (20 mL) and stirred at r.t. for 72 h. The reaction mixture was concentrated to dryness and passed through an SCX cartridge (5 g) eluting with DCM:MeOH: 7M methanolic ammonia (9:9:1). The eluted fraction was concentrated to dryness to give ethyl 2-[1-(azetidin-3-ylmethyl)azetidin-3-yl]oxyacetate. $^1$H NMR (400 MHz, CDCl$_3$) $\delta$ 4.24-4.00 (m, 6H), 3.75-3.56 (m, 4H), 3.39 (t, J=7.3 Hz, 1H), 3.06-2.89 (m, 2H), 2.71-2.61 (m, 3H), 1.31-1.24 (m, 3H), NH not observed.

Ethyl 2-[1-(azetidin-3-ylmethyl)azetidin-3-yl]oxyacetate (130 mg, 0.569 mmol, 1 eq), 5-chloro-N-(8-fluoro-2-methyl-imidazo[1,2-a]pyridin-6-yl)pyrazine-2-carboxamide (174 mg, 0.569 mmol, 1 eq), and triethylamine (0.16 mL, 1.14 mmol, 2 eq) were combined in acetonitrile (1 mL) and stirred at 55° C. for 6 days. The reaction mixture was concentrated to dryness, partitioned between DCM and water and the organics collected by phase separator. The organics were concentrated to dryness and purified by flash silica chromatography (5% MeOH in DCM [+1% 7M methanolic ammonia]) to give ethyl 2-[1-[[1-[5-[(8-fluoro-2-methyl-imidazo[1,2-a]pyridin-6-yl)carbamoyl]pyrazin-2-yl]azetidin-3-yl]methyl]azetidin-3-yl]oxyacetate. LCMS (ES+) 498.3 (M+H)+. $^1$H NMR (400 MHz, CDCl$_3$) $\delta$ 9.25-9.20 (m, 1H), 9.06 (t, J=1.8 Hz, 1H), 8.89-8.86 (m, 1H), 7.59-7.58 (m, 1H), 7.43-7.41 (m, 1H), 6.85-6.79 (m, 1H), 4.30-4.19 (m, 5H), 4.03 (s, 2H), 3.92-3.85 (m, 2H), 3.74-3.64 (m, 2H), 3.10-3.01 (m, 2H), 2.91-2.82 (m, 1H), 2.80 (d, J=7.3 Hz, 2H), 2.47 (s, 3H), 1.29 (t, J=8.2 Hz, 3H).

Ethyl 2-[1-[[1-[5-[(8-fluoro-2-methyl-imidazo[1,2-a]pyridin-6-yl)carbamoyl]pyrazin-2-yl]azetidin-3-yl]methyl]azetidin-3-yl]oxyacetate (40 mg, 0.0804 mmol, 1 eq) and 2 M aqueous sodium hydroxide (0.40 mL, 0.804 mmol, 10 eq) were combined in tetrahydrofuran (1 mL) and methyl alcohol (1 mL) and stirred at 50° C. for 17 h. The reaction mixture was concentrated to dryness and purified by preparative-HPLC to give 2-[1-[[1-[5-[(8-fluoro-2-methyl-imidazo[1,2-a]pyridin-6-yl)carbamoyl]pyrazin-2-yl]azetidin-3-yl]methyl]azetidin-3-yl]oxyacetic acid. LCMS (ES+) 470.3 (M+H)+.

To a solution of 2-[1-[[1-[5-[(8-fluoro-2-methyl-imidazo[1,2-a]pyridin-6-yl)carbamoyl]pyrazin-2-yl]azetidin-3-yl]methyl]azetidin-3-yl]oxyacetic acid (7.4 mg, 0.0158 mmol, 1 eq) in tetrahydrofuran (1 mL) were added N-(3-dimethylaminopropyl)-N'-ethylcarbodiimide (0.0028 mL, 0.0158 mmol, 1 eq), 1-hydroxybenzotriazole (2.1 mg, 0.0158 mmol, 1 eq), N,N-diisopropylethylamine (0.0055 mL, 0.0315 mmol, 2 eq), and 2-[3-(2-azidoethyl)diazirin-3-yl]ethanamine (2.4 mg, 0.0158 mmol, 1 eq) in THF (1 mL) in the dark. The mixture was stirred at r.t. for 5 days before additional 2-[3-(2-azidoethyl)diazirin-3-yl]ethanamine (2.4 mg, 0.0158 mmol, 1 eq) was added and stirred at r.t. for 2 days. Reaction stalled at 33%. The reaction mixture was concentrated to dryness and purified by preparative-HPLC to give 5-[3-[[3-[2-[2-[3-(2-azidoethyl)diazirin-3-yl]ethylamino]-2-oxo-ethoxy]azetidin-1-yl]methyl]azetidin-1-yl]-N-(8-fluoro-2-methyl-imidazo[1,2-a]pyridin-6-yl)pyrazine-2-carboxamide. LCMS (ES+) 606.2 (M+H)+, RT 2.38 min (Analytical method AcHSSC18). $^1$H NMR (400 MHz, CD$_3$CN) $\delta$ 9.46 (s, 1H), 9.07 (d, J=2.3 Hz, 1H), 8.77 (d, J=1.8 Hz, 1H), 7.74 (d, J=1.5 Hz, 1H), 7.64 (d, J=3.3 Hz, 1H), 7.18 (dd, J=1.4, 12.5 Hz, 1H), 6.93 (s, 1H), 4.25 (t, J=8.8 Hz, 2H), 4.22-4.16 (m, 1H), 3.87 (dd, J=5.5, 9.6 Hz, 2H), 3.83 (s, 2H), 3.61-3.56 (m, 2H), 3.22 (t, J=6.5 Hz, 2H), 3.14 (dd, J=6.9, 13.2 Hz, 2H), 3.05-3.00 (m, 2H), 2.89-2.79 (m, 1H), 2.76 (d, J=6.8 Hz, 2H), 2.41 (s, 3H), 1.71 (t, J=6.7 Hz, 2H), 1.65 (t, J=6.9 Hz, 2H).

Example 46: 5-(4-(((Cyclopropylamino)methyl)-1H-pyrazol-1-yl)-N-(8-fluoro-2-methylimidazo[1,2-a]pyridin-6-yl)pyrazine-2-carboxamide

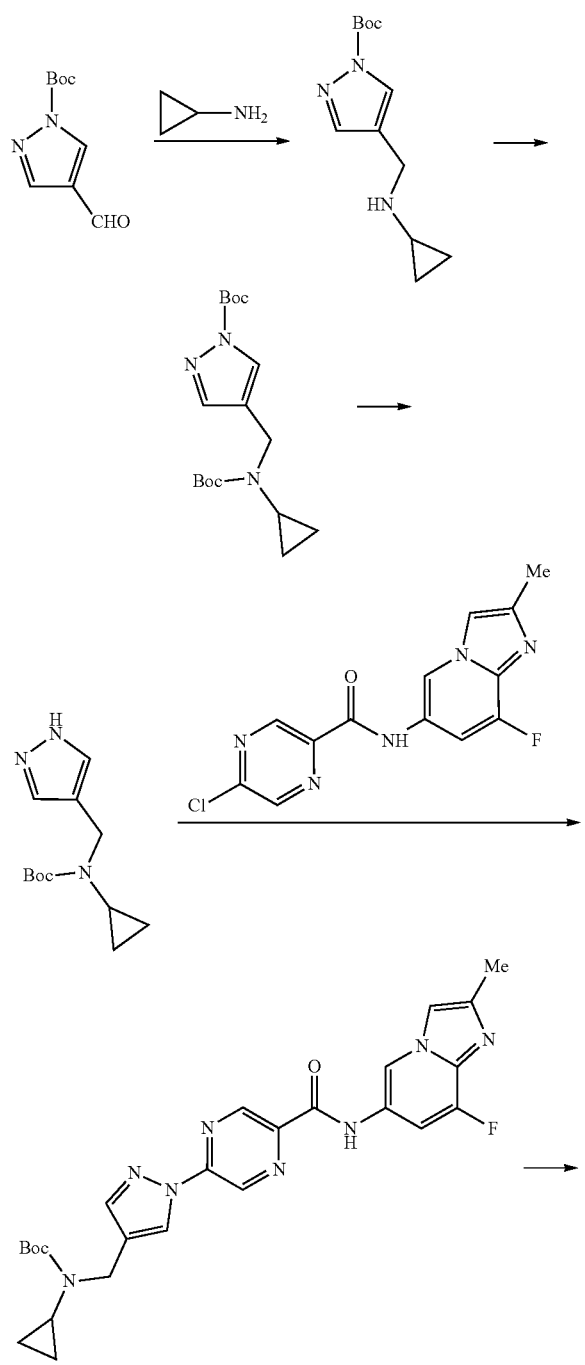

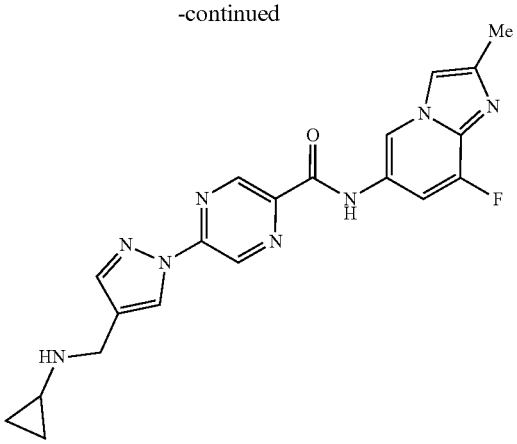

To a mixture of tert-butyl 4-formyl-1H-pyrazole-1-carboxylate (2.00 g, 10.2 mmol) and cyclopropanamine (1.75 g, 30.6 mmol) in dichloromethane (100 mL) at room temperature was added sodium triacetoxyborohydride (6.48 g, 30.6 mmol). The mixture was stirred at room temperature for 18 h. After this time, aqueous sodium bicarbonate (10% in water, 10 mL) was added, and the mixture was concentrated under reduced pressure. The residue obtained was purified by chromatography (silica gel; ethyl acetate to methanol; gradient elution) to afford impure tert-butyl 4-((cyclopropylamino)methyl)-1H-pyrazole-1-carboxylate, which was used in the next step without further purification.

To a mixture of tert-butyl 4-((cyclopropylamino)methyl)-1H-pyrazole-1-carboxylate (3.40 g, 14.3 mmol) and triethylamine (2.90 g, 28.7 mmol) in dichloromethane (100 mL) was added di-tert-butyl dicarbonate (3.75 g, 17.2 mmol) at room temperature. The mixture was stirred for 18 h. After this time, the solvent was removed under reduced pressure, and the residue obtained was purified by chromatography (silica gel; hexanes to ethyl acetate; gradient elution) to afford impure tert-butyl 4-(((tert-butoxycarbonyl)(cyclopropyl)amino)methyl)-1H-pyrazole-1-carboxylate, which was used in the next step without further purification.

To tert-butyl 4-(((tert-butoxycarbonyl)(cyclopropyl)amino)methyl)-1H-pyrazole-1-carboxylate (4.82 g, 14.3 mmol) in methanol (100 mL) at room temperature was added potassium carbonate (5.92 g, 42.9 mmol), and the mixture was stirred at room temperature for 18 h. After this time, the volatiles were removed under reduced pressure, and the residue obtained was purified by chromatography (silica gel; ethyl acetate to methanol; gradient elution) to afford tert-butyl ((1H-pyrazol-4-yl)methyl)-(cyclopropyl)carbamate, $^1$H NMR (500 MHz, DMSO-$d_6$) δ 12.65 (br s, 1H), 7.80-7.10 (br m, 2H), 4.18 (s, 2H), 2.40-2.25 (m, 1H), 1.40 (s, 9H), 0.70-0.60 (m, 2H), 0.60-0.50 (m, 2H).

To a mixture of tert-butyl ((1H-pyrazol-4-yl)methyl)(cyclopropyl)carbamate (0.0466 g, 0.196 mmol) and 5-chloro-N-(8-fluoro-2-methylimidazo[1,2-a]pyridin-6-yl)pyrazine-2-carboxamide (0.0400 g, 0.131 mmol) in acetonitrile (10 mL) at room temperature was added potassium carbonate (0.0362 g, 0.262 mmol). The mixture was heated at 82° C. for 48 h. After this time, the volatiles were removed under reduced pressure, and the residue obtained was purified by chromatography (silica gel; hexanes to ethyl acetate; gradient elution) to afford tert-butyl cyclo-propyl((1-(5-((8-fluoro-2-methylimidazo[1,2-a]pyridin-6-yl)carbamoyl)pyrazin-2-yl)-1H-pyrazol-4-yl)methyl)carbamate, $^1$H NMR (500 MHz, CDCl$_3$) δ 9.42 (s, 1H), 9.26 (d, J=1.4 Hz, 1H), 9.22 (d, J=1.3 Hz, 1H), 9.08 (d, J=1.6 Hz, 1H), 8.49 (d, J=0.5 Hz, 1H), 7.82 (s, 1H), 7.45 (dd, J=2.9, 0.6 Hz, 1H), 6.90 (dd, J=10.8, 1.7 Hz, 1H), 4.37 (s, 2H), 2.55-2.40 (m, 1H), 2.48 (d, J=0.6 Hz, 3H), 1.49 (s, 9H), 0.83-0.75 (m, 2H), 0.72-0.65 (m, 2H); MS (ESI) m/z: $[M+H]^+$ Calcd for $C_{25}H_{28}FN_8O_3$ 507.2; Found 507.5.

To a solution of tert-butyl cyclopropyl((1-(5-((8-fluoro-2-methylimidazo[1,2-a]pyridin-6-yl)-carbamoyl)pyrazin-2-yl)-1H-pyrazol-4-yl)methyl)carbamate (0.070 g, 1.4 mmol) in dichloromethane (3 mL) was added trifluoroacetic acid (1 mL), and the mixture was stirred at room temperature for 1 h. After this time, the volatiles were removed under reduced pressure, and the residue obtained was treated with sodium bicarbonate (10%, 1 mL). The mixture was concentrated under reduced pressure and purified by chromatography (silica gel; ethyl acetate to methanol; gradient elution). The impure product was repurified by prep HPLC on an XBridge Prep C18 OBD column (5 µm, 250×19 mm), eluted according to Method 4. Isolated product was converted to the free base by eluting with methanol on an MP-carbonate (5 g) column, and then purified again by prep HPLC on an XBridge Prep C18 OBD column (5 µm, 250×19 mm), eluted according to Method 5 to afford 5-(4-((cyclopropylamino)methyl)-1H-pyrazol-1-yl)-N-(8-fluoro-2-methylimidazo[1,2-a]pyridin-6-yl)-pyrazine-2-carboxamide, mp 194-196° C.; $^1$H NMR (500 MHz, DMSO-$d_6$) δ 10.96 (s, 1H), 9.25 (s, 1H), 9.22 (s, 1H), 9.13 (s, 1H), 8.58 (s, 1H), 8.00-7.85 (m, 2H), 7.58 (d, J=12.8 Hz, 1H), 3.71 (s, 2H), 2.34 (s, 3H), 2.15-2.00 (m, 1H), 0.42-0.32 (m, 2H), 0.32-0.20 (m, 2H); $^{19}$F NMR (471 MHz, DMSO-$d_6$) δ −131.79; MS (ESI) m/z: $[M+H]^+$ Calcd for $C_{20}H_{20}FN_8O$ 407.2; Found 407.4; UHPLC: Method 2, $t_R$=2.22 min, >99% (AUC) at 254 and 215 nm; UHPLC-MS: Method 3, $t_R$=1.16 min, >99% (AUC), MS (ESI) m/z: $[M+H]^+$ Calcd for $C_{20}H_{20}FN_8O$ 407.2; Found 407.5.

Method 4

| Time (min) | Flow (mL/min) | % A | % B |
|---|---|---|---|
| 0.0 | 5 | 95.0 | 5.0 |
| 0.5 | 5 | 95.0 | 5.0 |
| 1.0 | 20 | 95.0 | 5.0 |
| 4.0 | 20 | 95.0 | 5.0 |
| 44.0 | 20 | 0.0 | 100 |

A = Water with 0.2% v/v formic acid
B = Acetonitrile

Method 5

| Time (min) | Flow (mL/min) | % A | % B |
|---|---|---|---|
| 0.0 | 5 | 100 | 0.0 |
| 0.5 | 5 | 100 | 0.0 |
| 1.0 | 20 | 100 | 0.0 |
| 4.0 | 20 | 100 | 0.0 |
| 44.0 | 20 | 0.0 | 100 |

A = Water with 0.2% v/v formic acid
B = Acetonitrile

Other compounds described herein were prepared according to methods as described herein.

Biological Assay Example

Time-resolved FRET assay: Q48-Huntingtin and total-Huntington detection Detection of endogenous HTT protein in cell lysates was performed using a protocol adapted from Weiss et al. See Weiss A et al. (2009). Single-step detection of mutant huntingtin in animal and human tissues: a bioassay for Huntington's disease. Anal. Biochem. 395(1): 8-15.

The multiplex assay was performed in human embryonic stem cells (GEN020 hESCs with mutant 48 Q repeat allele) which have been derived by Genea Biocells from human blastocysts of HD donors. Bradley C K et al. (2011). Derivation of Huntington's disease-affected human embryonic stem cell lines, Stem Cells Dev. 2011 March; 20(3): 495-502. Cells were plated into 384-well collagen coated plates (10,000 cells per well) and left to adhere for 24 hours, test compounds were then added for 48 hours (37° C., 5% $CO_2$), cells were then lysed, and the lysate was transferred to a black 384-well assay plate.

The assay plate included a combination of HTRF labelled monoclonal antibodies added to recognize discreet areas of the HTT protein, the Tb "donor" antibody (2B7-Tb: 0.2 ng/well) recognizes a sequence at the N-terminus of the protein, an Alexa488 "acceptor 1" antibody (MW1-Alexa488: 30 ng/well) recognizes an area in the polyQ region, whereas a d2 "acceptor 2" antibody (MAB2166-d2: 6 ng/well) recognizes a sequence beyond the polyQ region. These detection reagents were incubated with the cell lysate at room temperature for 4-6 hours before having their fluorescence quantified at 615 nm (donor) and 535 nm and 665 nm (acceptor 1 and 2 respectively). The donor/acceptor ratio between these signals indicated the relative quantities of mHTT and tHTT.

Results for various compounds described herein are provided in the Tables below. tHTT activity in this assay is categorized as 10-20 µM (−); 1-10 µM (+); 0.5-1 µM (++); 0.1-0.5 µM (+++); <0.1 µM (++++).

| Ex. | HTT Lowering Activity (HTRF) (µM) |
|---|---|
| 1 | ++++ |
| 2 | ++ |
| 3 | +++ |
| 4 | ++++ |
| 5 | +++ |
| 6 | ++ |
| 7 | +++ |
| 8 | ++++ |
| 9 | +++ |
| 10 | +++ |
| 11 | +++ |
| 12 | +++ |
| 13 | +++ |
| 14 | +++ |
| 15 | ++++ |
| 16 | ++ |
| 17 | +++ |
| 18 | +++ |
| 19 | +++ |
| 20 | +++ |
| 21 | +++ |
| 22 | +++ |
| 23 | ++++ |
| 24 | ++++ |
| 25 | +++ |
| 26 | ++++ |
| 27 | +++ |
| 28 | +++ |
| 29 | ++++ |
| 30 | ++++ |
| 31 | ++++ |
| 32 | ++ |
| 34 | +++ |
| 35 | ++ |
| 36 | +++ |
| 37 | +++ |

| Ex. | HTT Lowering Activity (HTRF) (μM) |
|-----|-----------------------------------|
| 38  | ++                                |
| 39  | ++                                |
| 40  | +++                               |
| 41  | ++                                |
| 42  | +++                               |
| 43  | +++                               |
| 44  | +++                               |
| 45  | ++                                |
| 46  | ++                                |

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising," "including," "containing," etc. shall be read expansively and without limitation.

Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

All publications, patent applications, patents, and other references mentioned herein are expressly incorporated by reference in their entirety, to the same extent as if each were incorporated by reference individually. In case of conflict, the present specification, including definitions, will control.

What is claimed is:
1. A compound of Formula I:

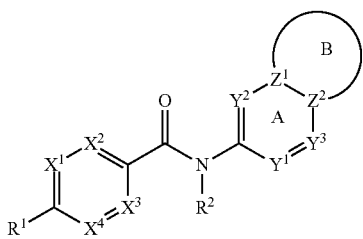

or an isotopically enriched analog, pharmaceutically acceptable salt, tautomer, stereoisomer, or a mixture of stereoisomers thereof, wherein:

$X^1$, $X^2$, $X^3$, and $X^4$ are $CR^4$ or N, wherein at least two but no more than three of $X^1$, $X^2$, $X^3$, and $X^4$ are N;
  each $R^4$ is independently hydrogen, halo, hydroxy, $C_{1-6}$alkyl, $C_{1-6}$haloalkyl, or $C_{1-6}$alkoxy;
$Y^1$ is $CR^5$;
  $R^5$ is $C_{1-6}$alkoxy substituted with $C_{2-6}$alkynyl, aryl, $C_{1-6}$alkoxy, heteroaryl, heterocyclyl, or cyano;
$Y^2$ is absent, $CR^6$, or N;
  $R^6$ is hydrogen, cyano, halo, hydroxy, $C_{1-6}$alkyl, $C_{1-6}$haloalkyl, $C_{1-6}$alkylthio, $C_{1-6}$alkoxy, $C_{1-6}$haloalkoxy, heterocyclyl, —$NH_2$, —$NHR^{17}$, or —$N(R^{17})_2$, and optionally substituted on an available nitrogen atom with $C_{1-6}$alkyl or $C_{1-6}$haloalkyl; and $Y^3$ is $CR^3$ or N;
  $R^3$ is hydrogen, cyano, halo, hydroxy, $C_{1-6}$alkyl, $C_{1-6}$haloalkyl, $C_{1-6}$alkylthio, $C_{1-6}$alkoxy, $C_{1-6}$haloalkoxy, heterocyclyl, —$NH_2$, —$NHR^{17}$, or —$N(R^{17})_2$, and optionally substituted on an available nitrogen atom with $C_{1-6}$alkyl or $C_{1-6}$haloalkyl;
  each $R^{17}$ is independently $C_{1-4}$alkyl, or two $R^{17}$ join, with any intervening atoms, to form a 3- to 6-membered heterocyclyl;
each of $Z^1$ and $Z^2$ is C or N;
Ring A and Ring B together form a 9- or 10-membered bicyclic heteroaryl containing 1 to 3 ring nitrogen atoms;
  Ring B contains 1 to 3 heteroatoms independently selected from N, O, and S, and is optionally substituted on available carbon atom(s) with 1 to 3 substituents independently selected from halo, hydroxy, $C_{1-6}$alkyl, $C_{1-6}$haloalkyl, $C_{1-6}$alkoxy, and $C_{1-6}$haloalkoxy, and optionally substituted on an available nitrogen atom with $C_{1-6}$alkyl or $C_{1-6}$haloalkyl;
$R^1$ is -$L^1$-$R^{11}$, wherein $L^1$ is —O—, —S—, —S(O)—, —$S(O)_2$—, —$N(R^{12})$—, —$C_{1-3}$alkylene-, —O—$C_{1-3}$alkylene-, —$N(R^{12})$—$C_{1-3}$alkylene-, or absent, and $R^{11}$ is $C_{2-6}$alkynyl, $C_{3-10}$cycloalkyl, $C_{6-10}$aryl, heteroaryl, or heterocyclyl, wherein $R^{11}$ is optionally substituted with 1 to 4 $R^{13}$ groups;
  $R^{12}$ is hydrogen or $C_{1-6}$alkyl;
  each $R^{13}$ is independently selected from halo, cyano, hydroxy, $C_{1-6}$alkyl optionally substituted with $R^{16}$, $C_{1-6}$haloalkyl, $C_{1-6}$hydroxyalkyl, $C_{3-10}$cycloalkyl optionally substituted with $R^{16}$, $C_{3-10}$cycloalkyl-$C_{1-6}$alkyl optionally substituted with $R^{16}$, $C_{6-10}$aryl optionally substituted with $R^{16}$, $C_{6-10}$aryl-$C_{1-6}$alkyl optionally substituted with $R^{16}$, heteroaryl optionally substituted with $R^{16}$, heteroaryl-$C_{1-6}$alkyl optionally substituted with $R^{16}$, heterocyclyl optionally substituted with $R^{16}$, heterocyclyl-$C_{1-6}$alkyl optionally substituted with $R^{16}$, $OR^{14}$, —$NH_2$, —$NHR^{14}$, —$N(R^{14})_2$, —$C_{1-6}$alkylene-$NH_2$, —$C_{1-6}$alkylene-$NHR^{14}$, —$C_{1-6}$alkylene-$N(R^{14})_2$, —$C(O)R^{15}$, —$C(O)OR^{15}$, —$C(O)NHR^{15}$, —$C(O)N(C_{1-4}$alkyl)$R^{15}$, —$S(O)_2R^{15}$, —$S(O)R^{15}$, —$NHC(O)R^{15}$, —$N(C_{1-4}$alkyl$)C(O)R^{15}$, —$NHS(O)R^{15}$, —$N(C_{1-4}$alkyl$)S(O)R^{15}$, —$NHS(O)_2R^{15}$, and —$N(C_{1-4}$alkyl$)S(O)_2R^{15}$,
  each $R^{14}$ is independently selected from $C_{1-6}$alkyl, $C_{3-10}$cycloalkyl, $C_{6-10}$aryl, heteroaryl, and heterocyclyl; and each $R^{14}$ is optionally substituted with one to six halo, $C_{1-3}$alkyl, $C_{1-3}$alkoxy, $C_{3-10}$cycloalkyl, or —$NHSO_2$-aryl-$N(CH_3)_2$;
  each $R^{15}$ is independently hydrogen, —OH, $C_{1-6}$alkyl, $C_{1-6}$haloalkyl, $C_{3-10}$cycloalkyl, $C_{6-10}$aryl, heteroaryl, or heterocyclyl;
  each $R^{16}$ is independently halo, cyano, hydroxy, —$NH_2$, —$NHR^{21}$, —$N(R^{21})_2$, $C_{1-6}$alkyl, $C_{1-6}$haloalkyl, $OR^{21}$, or $C_{3-10}$cycloalkyl;
    each $R^{21}$ is independently selected from $C_{1-6}$alkyl, $C_{3-10}$cycloalkyl, $C_{6-10}$aryl, heteroaryl, heterocyclyl, and —$CH_2C(O)NHR^{22}$; and each $R^{21}$ is optionally substituted with one to six halo or $C_{1-3}$alkoxy and $R^{22}$ is $C_{1-6}$alkyl substituted with heterocyclyl and $N_3$; and
$R^2$ is hydrogen or $C_{1-6}$alkyl.

2. The compound of claim 1, of Formula Ia, Formula Ib, or Formula Ic:

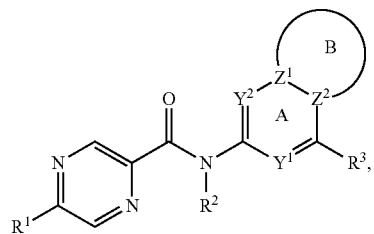

Ia

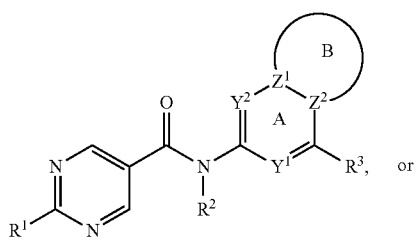

Ib

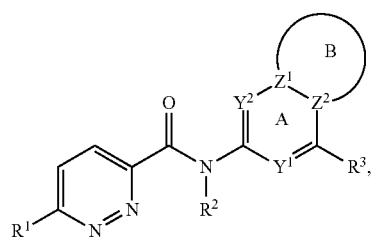

Ic or an isotopically enriched analog, pharmaceutically acceptable salt, tautomer, stereoisomer, or a mixture of stereoisomers thereof.

3. The compound of claim 1, of Formula IIa:

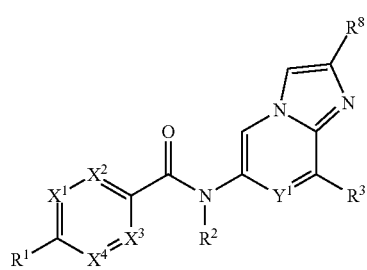

IIa or an isotopically enriched analog, pharmaceutically acceptable salt, tautomer, stereoisomer, or a mixture of stereoisomers thereof, wherein $R^8$ is hydrogen, halo, hydroxy, $C_{1-6}$alkyl, $C_{1-6}$haloalkyl, $C_{1-6}$alkoxy, or $C_{1-6}$haloalkoxy.

4. The compound of claim 1, of Formula IIb:

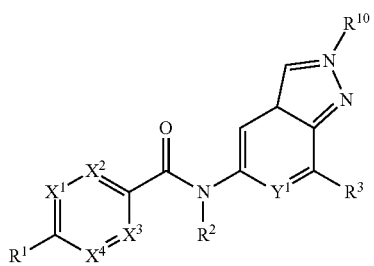

IIb or an isotopically enriched analog, pharmaceutically acceptable salt, tautomer, stereoisomer, or a mixture of stereoisomers thereof, wherein $R^{10}$ is hydrogen, $C_{1-6}$alkyl, or $C_{1-6}$haloalkyl.

5. The compound of claim 1, of Formula IIIa, Formula IIIb, or Formula IIIc:

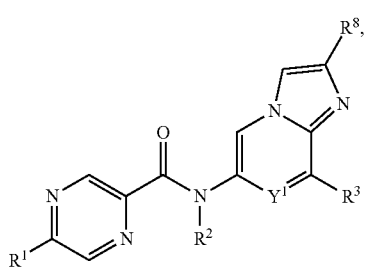

IIIa

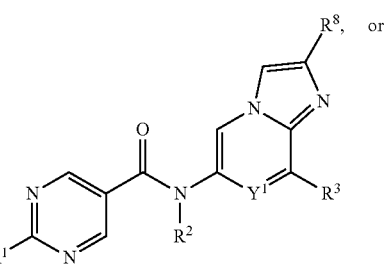

IIIb

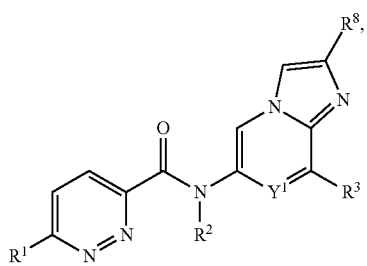

IIIc or an isotopically enriched analog, pharmaceutically acceptable salt, tautomer, stereoisomer, or a mixture of stereoisomers thereof, wherein $R^8$ is hydrogen, halo, hydroxy, $C_{1-6}$alkyl, $C_{1-6}$haloalkyl, $C_{1-6}$alkoxy, or $C_{1-6}$haloalkoxy.

6. The compound of claim 1, wherein $R^{11}$ is heterocyclyl optionally substituted with 1 to 4 groups independently selected from halo, $C_{1-6}$alkyl, $C_{1-6}$haloalkyl, $C_{3-10}$cycloalkyl, heteroaryl, heterocyclyl, heterocyclyl-$C_{1-6}$alkyl, —$NH_2$, —$NHR^{14}$, —$N(R^{14})_2$, —$C_{1-6}$alkylene-$NH_2$, —$C_{1-6}$alkylene-$NHR^{14}$, —$C_{1-6}$alkylene-$N(R^{14})_2$, and —$C(O)OR^{15}$; wherein each $R^{14}$ is independently selected from $C_{1-6}$alkyl, $C_{3-10}$cycloalkyl, and heterocyclyl, and each $R^{14}$ is optionally substituted with one to three halo; and wherein $R^{15}$ is $C_{1-6}$alkyl.

7. The compound of claim 1, wherein $R^{11}$ is

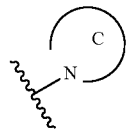

wherein Ring C is a 3- to 10-membered heterocyclyl containing 0, 1 or 2 additional ring nitrogen atoms optionally substituted with 1 to 4 $R^{13}$ groups.

8. The compound of claim 7, wherein Ring C is a 5- to 10-membered spirobicyclic heterocyclyl containing one additional ring nitrogen atom optionally substituted with 1 to 4 $R^{13}$ groups.

9. The compound of claim 1, wherein $R^3$ is halo.

10. The compound of claim 1, wherein $R^3$ is hydrogen.

11. The compound of claim 1, wherein each $R^4$ is hydrogen.

12. The compound of claim 1, wherein $R^2$ is hydrogen.

13. The compound of claim 1, wherein $L^1$ is absent.

14. The compound of claim 1, wherein $Y^2$ is $CR^6$.

15. The compound of claim 1, wherein $Y^3$ is $CR^3$.

16. A compound selected from:

1

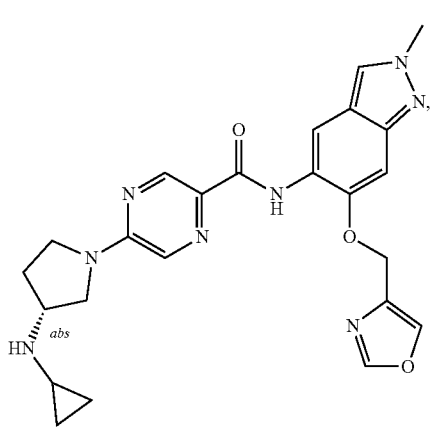

2

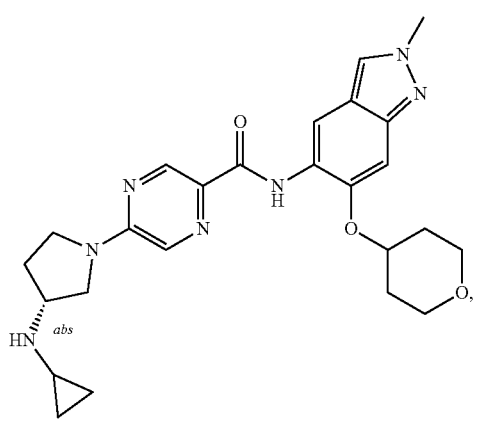

3

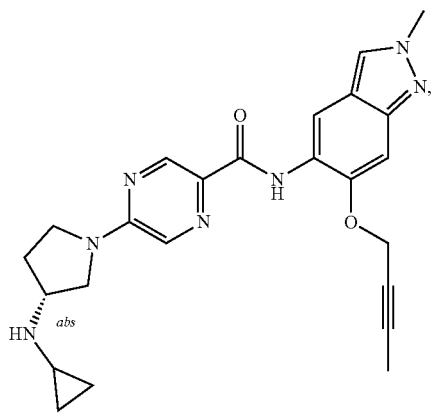

4

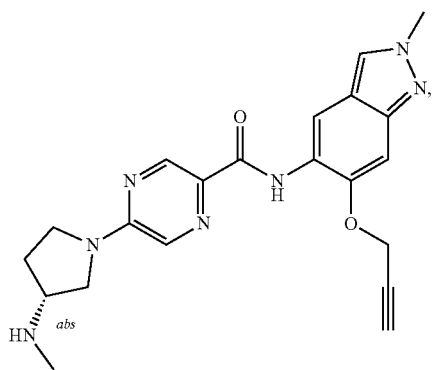

5

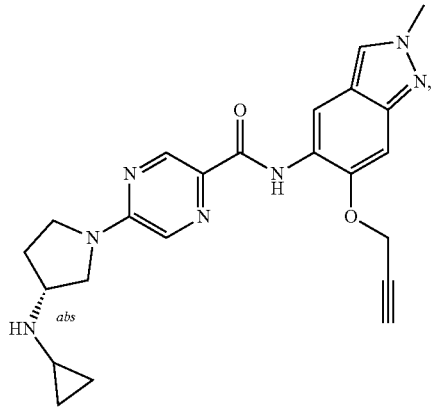

6

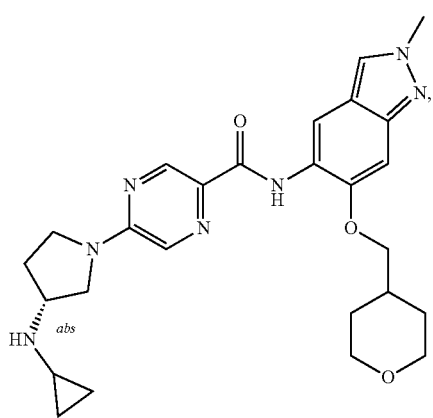

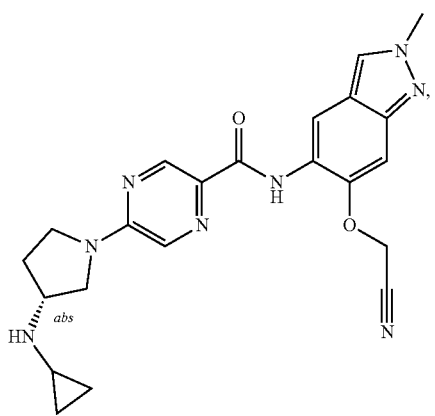

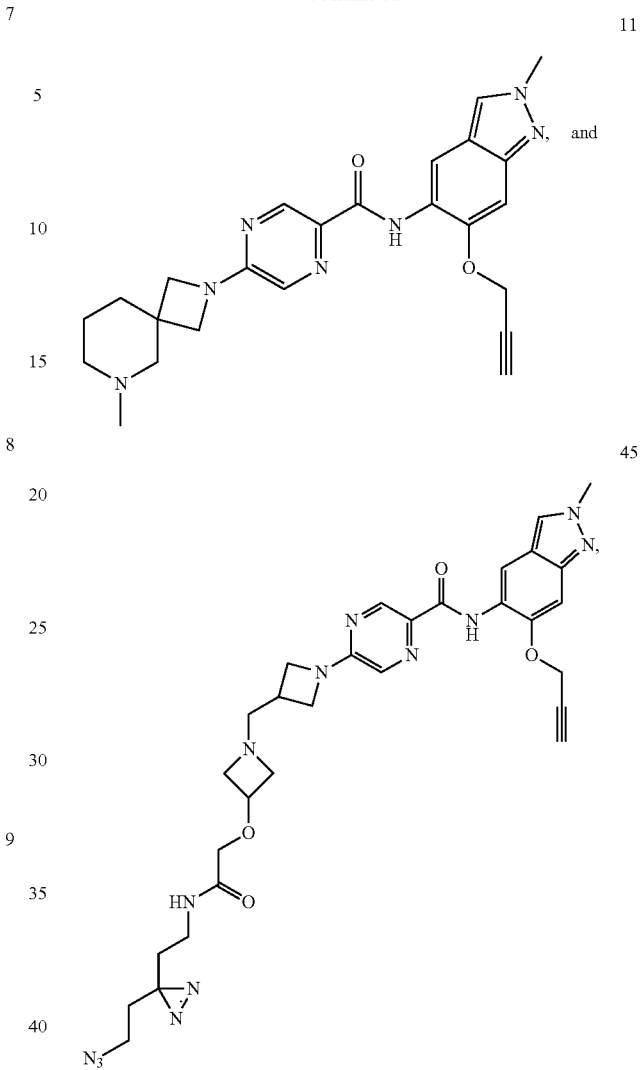

or an isotopically enriched analog, pharmaceutically acceptable salt, tautomer, stereoisomer, or a mixture of stereoisomers thereof.

17. A pharmaceutical composition comprising the compound of claim 1, or an isotopically enriched analog, pharmaceutically acceptable salt, tautomer, stereoisomer, or a mixture of stereoisomers thereof, and a pharmaceutically acceptable excipient.

18. A method for treating Huntington's disease in a patient in need thereof, comprising administering to the patient a therapeutically effective amount of the compound of claim 1.

19. A method for treating Huntington's disease in a patient in need thereof, comprising administering to the patient a therapeutically effective amount of the compound of claim 1 in combination with a second active agent.

* * * * *